(12) United States Patent
Hotchkiss et al.

(10) Patent No.: US 8,354,259 B2
(45) Date of Patent: Jan. 15, 2013

(54) METHOD AND SYSTEM FOR LACTOSE-FREE OR LACTOSE-REDUCED MILK AND ASSOCIATED PRODUCTS, PRODUCTION THEREOF, AND ASSOCIATED PROCESSES

(75) Inventors: Joseph H. Hotchkiss, Ithaca, NY (US); Joey N. Talbert, Ithaca, NY (US)

(73) Assignee: Cornell University, Ithaca, NY (US)

( * ) Notice: Subject to any disclaimer, the term of this patent is extended or adjusted under 35 U.S.C. 154(b) by 368 days.

(21) Appl. No.: 12/665,519

(22) PCT Filed: Jun. 18, 2008

(86) PCT No.: PCT/US2008/067376
§ 371 (c)(1),
(2), (4) Date: Mar. 19, 2010

(87) PCT Pub. No.: WO2008/157624
PCT Pub. Date: Dec. 24, 2008

(65) Prior Publication Data
US 2010/0196985 A1    Aug. 5, 2010

Related U.S. Application Data

(60) Provisional application No. 60/944,594, filed on Jun. 18, 2007.

(51) Int. Cl.
*C12N 11/08* (2006.01)
*C12N 9/96* (2006.01)
*C12N 9/38* (2006.01)

(52) U.S. Cl. ......... 435/177; 435/180; 435/188; 435/207

(58) Field of Classification Search .................. None
See application file for complete search history.

(56) References Cited

U.S. PATENT DOCUMENTS

| 6,312,727 | B1 | 11/2001 | Schacht et al. |
| 6,927,051 | B1 | 8/2005 | Wang et al. |
| 2004/0254419 | A1 | 12/2004 | Wang et al. |
| 2006/0040280 | A1* | 2/2006 | Lee et al. ........................ 435/6 |
| 2007/0111289 | A1 | 5/2007 | Yang et al. |

FOREIGN PATENT DOCUMENTS

WO    2006024115 A1    3/2006

OTHER PUBLICATIONS

Rejikumar et al. International Journal of Food Chemistry (2001) 36, 91-98.*
Krajewska, Barbara (2004) Enzyme and Microbial Technology 35, 126-139.*
Krajewska, Barbara; Application of Chitin- and Chitosan-Based Materials for Enzyme Immobilizations: A Review; Enzyme and Microbial Technology; vol. 35, Issues 2-3, Aug. 5, 2004, pp. 126-139, Abstract only.
Goddard et al.; Covalent Attachment of Lactase to Low Density Polyethylene Films; Department of Food Science; Cornell University; Jun. 21, 2006.

* cited by examiner

*Primary Examiner* — Nashaat Nashed
(74) *Attorney, Agent, or Firm* — William Greener; Frederick JM Price; Bond, Schoeneck & King, PLLC

(57) ABSTRACT

A system and method capable of hydrolyzing lactose, where the system includes a support formed from a functionalized hydrophobic polymer that is covalently linked to a hydrophilic molecule covalently that is, in turn, covalently linked to an enzyme such as lactose. The method includes the steps of functionalizing a hydrophobic polymer support, covalently linking a hydrophilic molecule to said functionalized polymer support, and covalently linking an enzyme such as lactase to said hydrophilic molecule. The system and method generally relate to the field of food science and engineering and, more particularly to dairy-based food products and their production including solutions to problems associated with lactose intolerance such as product processing methods and products produced by these methods.

34 Claims, 40 Drawing Sheets

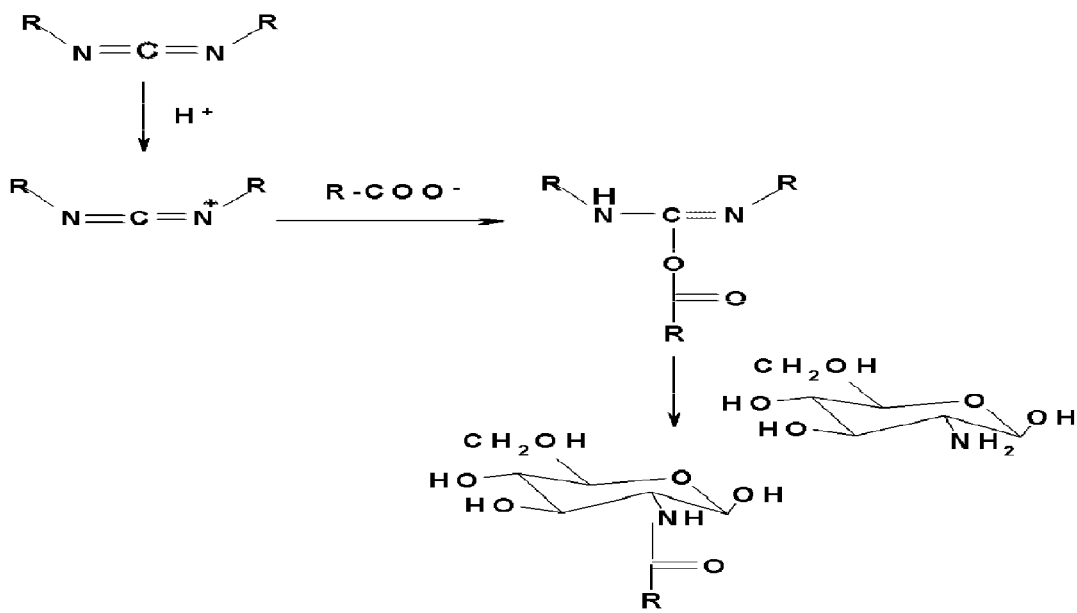

Figure 12

MKLLSVAAVALLAAQAAGASIKHRLNGFTILEHPDPAKRDLLQDIVTWDDKSLFINGERIMLFSGE
VHPFRLPVPSLWLDIFHKIRALGFNCVSFYIDWALLEGKPGDYRAEGIFALEPFFDAAKEAGIYLIA
RPGSYDNAEVSGGGFPGWLQRVNGTLRSSDEPFLKATDNYIANAAAAVAKAQITNGGPVILYQPE
NEYSGGCGVKYTDADYMQYVMDQAEKADIVVPFSNDASPSGHNAPGSGTGAVDIYGHDSYPL
GFDCANPNVWPEGKLPDNFKTLRLEQSPSAPYSLLEPQAGAFDPWGGPGFEKCYALVNHEFSRVF
YRNDLSFGVSTFNLYMTFGGTMWGNLGHPGGYTSYDYGSPTIETRNVTREKYSDIKLLANFVKAS
PSYLTATPPNLTTGVYTDTSDLAVTPLIGDSPGSFVVRHTDYSSQESTSYELKLPTSAGNLTIPQLE
GTLSLNGKDSKIHVVDYNVSGTNIEYSTAEVFTWKKFDGNKVLVLYGGPKEHHELAIANKSNVTIE
GSDSGIVSTRKGSSVIIGWDVSSTRRIVQVGDLRVFLLGKNSAYNYWVPELPTEGTSPGFSTSKTTA
SSEVKAGYLLRGAHLDGADLHLTADFNATTPIEVIGAPTGAKNLFVNGEKASHTVDKNGIWSSEV
KYAAPEIKLPGLKDLDWKYLDTLPEEKSSYDDSAWVSADLPKTKNTHEPLDTPTSLYSSDYGFHTG
YLJYRGHFVANGKESEFLIRTQGCSAFGSSVWLNETYLGSWTGADYTMDGNSTYKLSQLESGNYE
VITVVIDNLQLDENWTVGEETMKNPRGILSYKLSGQDASAITWKLTGNLGGEDYQDKVRGPLNEG
GLYAERGGTHQPQPPSDSWESGSPLEGLSKPGIGFYTAQFDLDLPKRAEGPSSTS

Figure 13

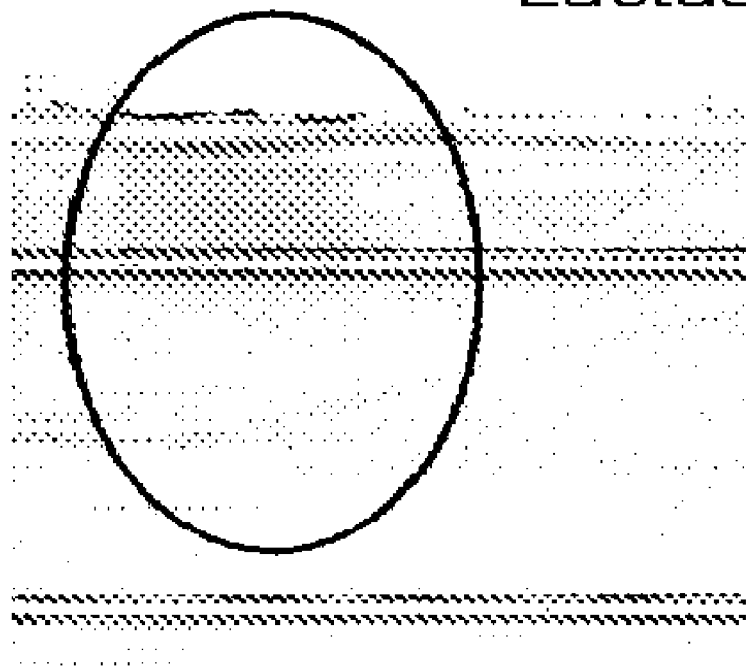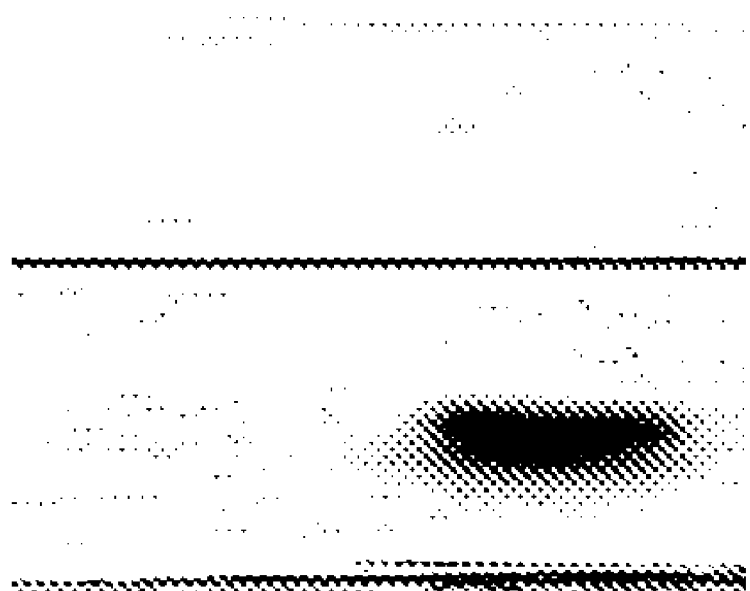
Figure 14

|         | %C   | %O  |
|---------|------|-----|
| PE      | 99.6 | 0.4 |
| PE-COOH | 94.4 | 5.6 |

SEQUENCE LISTING

```
<160> NUMBER OF SEQ ID NOS: 1

<210> SEQ ID NO 1
<211> LENGTH: 911
<212> TYPE: PRT
<213> ORGANISM: Aspergillus oryzae

<400> SEQUENCE: 1

Met Lys Leu Leu Ser Val Ala Ala Val Ala Leu Leu Ala Ala Gln Ala
1               5                   10                  15

Ala Gly Ala Ser Ile Lys His Arg Leu Asn Gly Phe Thr Ile Leu Glu
            20                  25                  30

His Pro Asp Pro Ala Lys Arg Asp Leu Leu Gln Asp Ile Val Thr Trp
        35                  40                  45

Asp Asp Lys Ser Leu Phe Ile Asn Gly Glu Arg Ile Met Leu Phe Ser
    50                  55                  60
```

-continued

```
Gly Glu Val His Pro Phe Arg Leu Pro Val Pro Ser Leu Trp Leu Asp
 65                  70                  75                  80

Ile Phe His Lys Ile Arg Ala Leu Gly Phe Asn Cys Val Ser Phe Tyr
                 85                  90                  95

Ile Asp Trp Ala Leu Leu Glu Gly Lys Pro Gly Asp Tyr Arg Ala Glu
            100                 105                 110

Gly Ile Phe Ala Leu Glu Pro Phe Phe Asp Ala Ala Lys Glu Ala Gly
        115                 120                 125

Ile Tyr Leu Ile Ala Arg Pro Gly Ser Tyr Ile Asn Ala Glu Val Ser
    130                 135                 140

Gly Gly Gly Phe Pro Gly Trp Leu Gln Arg Val Asn Gly Thr Leu Arg
145                 150                 155                 160

Ser Ser Asp Glu Pro Phe Leu Lys Ala Thr Asp Asn Tyr Ile Ala Asn
                165                 170                 175

Ala Ala Ala Ala Val Ala Lys Ala Gln Ile Thr Asn Gly Gly Pro Val
            180                 185                 190

Ile Leu Tyr Gln Pro Glu Asn Glu Tyr Ser Gly Gly Cys Cys Gly Val
        195                 200                 205

Lys Tyr Thr Asp Ala Asp Tyr Met Gln Tyr Val Met Asp Gln Ala Arg
    210                 215                 220

Lys Ala Asp Ile Val Val Pro Phe Ile Ser Asn Asp Ala Ser Pro Ser
225                 230                 235                 240

Gly His Asn Ala Pro Gly Ser Gly Thr Gly Ala Val Asp Ile Tyr Gly
                245                 250                 255

His Asp Ser Tyr Pro Leu Gly Phe Asp Cys Ala Asn Pro Ser Val Trp
            260                 265                 270

Pro Glu Gly Lys Leu Pro Asp Asn Phe Arg Thr Leu His Leu Glu Gln
        275                 280                 285

Ser Pro Ser Ala Pro Tyr Ser Leu Leu Glu Phe Gln Ala Gly Ala Phe
    290                 295                 300

Asp Pro Trp Gly Gly Pro Gly Phe Glu Lys Cys Tyr Ala Leu Val Asn
305                 310                 315                 320

His Glu Phe Ser Arg Val Phe Tyr Arg Asn Asp Leu Ser Phe Gly Val
                325                 330                 335

Ser Thr Phe Asn Leu Tyr Met Thr Phe Gly Gly Thr Asn Trp Gly Asn
            340                 345                 350

Leu Gly His Pro Gly Gly Tyr Thr Ser Tyr Asp Tyr Gly Ser Pro Ile
        355                 360                 365

Thr Glu Thr Arg Asn Val Thr Arg Glu Lys Tyr Ser Asp Ile Lys Leu
    370                 375                 380

Leu Ala Asn Phe Val Lys Ala Ser Pro Ser Tyr Leu Thr Ala Thr Pro
385                 390                 395                 400

Arg Asn Leu Thr Thr Gly Val Tyr Thr Asp Thr Ser Asp Leu Ala Val
                405                 410                 415

Thr Pro Leu Ile Gly Asp Ser Pro Gly Ser Phe Phe Val Val Arg His
            420                 425                 430

Thr Asp Tyr Ser Ser Gln Glu Ser Thr Ser Tyr Lys Leu Lys Leu Pro
        435                 440                 445

Thr Ser Ala Gly Asn Leu Thr Ile Pro Gln Leu Glu Gly Thr Leu Ser
    450                 455                 460

Leu Asn Gly Arg Asp Ser Lys Ile His Val Val Asp Tyr Asn Val Ser
465                 470                 475                 480

Gly Thr Asn Ile Ile Tyr Ser Thr Ala Glu Val Phe Thr Trp Lys Lys
                485                 490                 495
```

```
Phe Asp Gly Asn Lys Val Leu Val Leu Tyr Gly Gly Pro Lys Glu His
            500                 505                 510

His Glu Leu Ala Ile Ala Ser Lys Ser Asn Val Thr Ile Ile Glu Gly
        515                 520                 525

Ser Asp Ser Gly Ile Val Ser Thr Arg Lys Gly Ser Ser Val Ile Ile
    530                 535                 540

Gly Trp Asp Val Ser Ser Thr Arg Arg Ile Val Gln Val Gly Asp Leu
545                 550                 555                 560

Arg Val Phe Leu Leu Gly Lys Asn Ser Ala Tyr Asn Tyr Trp Val Pro
                565                 570                 575

Glu Leu Pro Thr Glu Gly Thr Ser Pro Gly Phe Ser Thr Ser Lys Thr
            580                 585                 590

Thr Ala Ser Ser Ile Ile Val Lys Ala Gly Tyr Leu Leu Arg Gly Ala
        595                 600                 605

His Leu Asp Gly Ala Asp Leu His Leu Thr Ala Asp Phe Asn Ala Thr
    610                 615                 620

Thr Pro Ile Glu Val Ile Gly Ala Pro Thr Gly Ala Lys Asn Leu Phe
625                 630                 635                 640

Val Asn Gly Glu Lys Ala Ser His Thr Val Asp Lys Asn Gly Ile Trp
                645                 650                 655

Ser Ser Glu Val Lys Tyr Ala Ala Pro Glu Ile Lys Leu Pro Gly Leu
            660                 665                 670

Lys Asp Leu Asp Trp Lys Tyr Leu Asp Thr Leu Pro Glu Ile Lys Ser
        675                 680                 685

Ser Tyr Asp Asp Ser Ala Trp Val Ser Ala Asp Leu Pro Lys Thr Lys
    690                 695                 700

Asn Thr His Arg Pro Leu Asp Thr Pro Thr Ser Leu Tyr Ser Ser Asp
705                 710                 715                 720

Tyr Gly Phe His Thr Gly Tyr Leu Ile Tyr Arg Gly His Phe Val Ala
                725                 730                 735

Asn Gly Lys Glu Ser Glu Phe Leu Ile Arg Thr Gln Gly Gly Ser Ala
            740                 745                 750

Phe Gly Ser Ser Val Trp Leu Asn Glu Thr Tyr Leu Gly Ser Trp Thr
        755                 760                 765

Gly Ala Asp Tyr Thr Met Asp Gly Asn Ser Thr Tyr Lys Leu Ser Gln
    770                 775                 780

Leu Glu Ser Gly Asn Tyr His Val Ile Thr Val Val Ile Asp Asn Leu
785                 790                 795                 800

Gly Leu Asp Glu Asn Trp Thr Val Gly Glu Thr Met Lys Asn Pro
                805                 810                 815

Arg Gly Ile Leu Ser Tyr Lys Leu Ser Gly Gln Asp Ala Ser Ala Ile
            820                 825                 830

Thr Trp Lys Leu Thr Gly Asn Leu Gly Glu Asp Tyr Gln Asp Lys
        835                 840                 845

Val Arg Gly Pro Leu Asn Glu Gly Leu Tyr Ala Glu Arg Gln Gly
    850                 855                 860

Phe His Gln Pro Gln Pro Ser Asp Ser Trp Glu Ser Gly Ser Pro
865                 870                 875                 880

Leu Glu Gly Leu Ser Lys Pro Gly Ile Gly Phe Tyr Thr Ala Gln Phe
                885                 890                 895

Asp Leu Asp Leu Pro Lys Arg Ala Glu Gly Pro Ser Ser Thr Ser
            900                 905                 910
```

METHOD AND SYSTEM FOR LACTOSE-FREE OR LACTOSE-REDUCED MILK AND ASSOCIATED PRODUCTS, PRODUCTION THEREOF, AND ASSOCIATED PROCESSES

CROSS-REFERENCE TO RELATED APPLICATIONS

This application claims priority to U.S. Provisional Patent Application Ser. No. 60/944,594, filed Jun. 18, 2007, the entirety of which is hereby incorporated by reference herein.

BACKGROUND OF THE INVENTION

1. Field of the Invention

The present invention relates to the field of food science and engineering and, more particularly to dairy-based food products and their production including solutions to problems associated with lactose intolerance such as product processing methods and products produced by these methods.

2. Description of the Related Art

The nutritional problems associated with lactose, a disaccharide consisting of glucose and galactose, which in whole bovine milk constitutes 4.8 w/v % of the product, are well known. After weaning, humans may lose their ability to digest lactose due to a decrease in cellular production of the intestinal enzyme, lactase/β-galactosidase (β-D-galactoside galactohydrase, EC 3.2.1.23), which catalyzes the hydrolysis of the β(1-4) glycosidic bonds of lactose to obtain glucose and galactose monosaccharides at the brush border of the small intestine, allowing for uptake. The enzyme deficiency results in a variety of adverse health effects including gastrointestinal problems due to the inability of sugar to be hydrolyzed, and; consequently, absorbed. The undigested sugar then goes to the large intestine where it is fermented by microorganisms, producing acids and gas—resulting in flatulence, diarrhea, and cramping.

Estimates suggest that nearly 70% of the world's population is lactose intolerant, and that lactase deficiency corresponds to genetic populations originating from areas where milk and dairy are and were not staples in traditional diets, particularly affecting those of Asian and African decent. Likewise, those originating from areas with a history of milk consumption have adapted accordingly. Ethnically, the breakdown of lactose intolerance in the United States is: Caucasian-15%, Hispanic-53%, African-American-80%, and Asian-90%. There is, also, evidence that lactose intolerance increases with aging and loss of cellular production of the enzyme. In the United States, intolerance varies, with about one-third of the U.S. population having problems with lactose consumption. Lactose intolerance can result in the avoidance of dairy products, which account for over half of the daily calcium intake in the U.S. Insufficient calcium intake, in return, results in corresponding health issues, including osteoporosis. Current strategies for treating lactose maldigestion include lactase supplements, lactose-reduced dairy products, and avoidance of dairy products. Adverse nutritional and physical effects, as well as economic potential, have prompted research and opportunity in the utilization of lactose-reducing methods for the improvement and modification of milk and other dairy products.

Lactose, in food products can be reduced both prior to and after consumption of dairy. Methods of reduction include chemical hydrolysis, ultrafiltration, and utilization of external sources of the enzyme, β-galactosidase (lactase). In fluid milk products, the goal of lactose reduction is to hydrolyze the sugar between 70-100%. Less than 100% reduction is targeted because lactose has low sweetness relative to its monomers—glucose and galactose; which have a sweetness approximately 80% that of sucrose. The enhanced sweetness associated with hydrolysis is often unappealing to consumers, who have shown to significantly detect differences in sweetness at 80% lactose reduction. Chemical methods, which rely on acid hydrolysis of the sugar prior to consumption, are not useful in food products because of whole-food changes in sensory and nutritional loss that occur with the treatment. Ultrafiltration, as a processing step, has yet to find a market, because of energy and capital inputs, and the difficulty in separating lactose from similar sized molecules (i.e., vitamins). In the food industry, applications employing lactase to reduce lactose have been most successful.

Lactases are produced by microbial and in mammalian organisms, and are commercially available from yeast, mold, and bacterial sources. The common sources of commercially viable lactases are *Kluyveromyces lactis, Candida pseudotropicalis, Aspergillus niger*, and *Aspergillus oryae*. Mahoney makes the distinction that all lactases are β-galactosidases, while not all β-galactosidases are lactases because some plant cells and mammalian organs possess β-galactosidases that have little or no enzymatic activity on lactose. For food applications the diversity is reduced due to regulatory restrictions, being limited, as a direct food additive, to *Kluyveromyces lactis* and *Candida pseudotropicalis*, as well as *Aspergillus oryae* and *niger*, which have GRAS approval. Lactases have been used to produce reduced lactose milk, improve the properties of ice cream in regards to crystallization, whipping, and viscosity properties, and for yoghurt to improve gelation, body, texture, and taste.

Lactase activity is affected by pH, temperatures, purity, and interaction with chemicals, which effects the application of the enzyme. Optimal pH and temperature varies with the source, modification, and method of preparation. Fungal lactases have an optimum pH range from 2.5-5.0, and yeast lactases range from 6.0-7.0. Yeast lactases are suited for fluid milk applications (pH 6.6-6.8), while fungal lactase are utilized in fermented diary products and for whey processing. The optimum temperature for fungal lactase is between 50-55° C., while yeast lactases range from 30-40° C., and are rapidly denatured over 40° C. Stability of lactase is affected by not only pH and temperature, but also interactions with other components, including divalent cations, lactose, and proteins found in milk. Mahoney and Wilder found that the half life of lactase from *K. marxianus* in milk was 20 times greater than in milk salts and 50 times greater than in phosphate buffer, presumably due to enhancement of hydrophobic interactions. Lactase purity is an important, though often overlooked, property of enzyme applications. Commercial sources of lactase have proteases present from incomplete purification of whole cell extracts that may degrade the product when in direct contact for a period of time. For milk applications, the presence of proteases can result in the production of undesirable texture and flavor changes. This factor is of special consideration for ultra high temperature (UHT) processed milk, which is processed to be stored for an extended time, and often have problems associated with proteases from sources other than lactase, and must be considered prior to application.

Applications that employ lactase to reduce lactose are useful for both fluid milk and whey processing. Lactose from whey, a byproduct of cheese manufacturing, can be hydrolyzed by the enzyme to produce sugars for use as prebiotics and sweeteners. Processing of whey with lactase provides not only nutritional advantages but also waste management improvements. Sweet whey, derived from the manufacturing of cheeses with rennet and acid whey, from manufacturing using acid coagulation, has, in the past been treated as a waste product. Whey components, particularly proteins, have found niche markets as nutritional supplements, edible films, and dried whey powder for emulsification and protein solubility in food applications. Whey powder, whey protein concentrate, and whey isolate, as ingredients for food applications, contain lactose. Reduction of lactose in these products provides not only advantages for lactose intolerant consumers, but also enhancements in food texture and consumer acceptability when using the ingredients because of the higher solubility of glucose and galactose compared to lactose and the decrease in lactose crystallization. The protein from whey can be removed by filtration making it even more suited for lactase activity. The permeate, which contains primarily lactose, vitamins and minerals, can be used for prebiotics, as syrup for utilized as a sweetener with increased solubility, or for animal feed. In a similar manner, permeate from skim milk is produced when microorganisms (and because of size similarities, proteins) are removed from the milk by ultra and microfiltration. The resulting permeate, which has a substantially reduced microbial load, is similar to that of sweet whey permeate. After processing, the fractionated portions can be added back to form a product with a lower bacterial count. Processing in this form may allow for the use of lactase, with minimal interferences from microorganisms, fat, and protein, to be used in the production of a lactose-reduced fluid milk product. Other applications of lactase to reduce lactose for consumption include: tablets that are taken prior to ingesting dairy, processing of fluid milk with lactase by the consumer, addition of the enzyme prior to or after pasteurization, and use of immobilized enzyme reactor.

Dosage forms, in which the enzyme is entrapped in a capsule and taken orally prior to the consumption of milk, can be used directly by the consumer. Doses must be taken in an appropriate time period to allow the enzyme to reach the intestine prior to consumption of dairy. Lactases added to milk are developed from yeast; however, those taken orally are from fungal sources to better accommodate the acidic conditions of the stomach. This method is, particularly, useful to consumers who eat-out and may ingest lactose. Lactose reduction by the consumer can, also, be achieved by the addition of a lactase tablets that is treated overnight at refrigeration temperatures.

The addition of lactase in milk prior to purchase by the consumer has been developed to provide convenience and decreased cost for the consumer while meeting a market demand and increasing profits for the producer. Lactase has been added prior or after pasteurization because of the susceptibility of yeast lactases to denaturation at processing temperatures used for batch, high temperature short time (HTST) and ultra high temperature (UHT) pasteurization, which occur at temperatures of 135° C. and higher. The addition of lactase prior to pasteurization has the advantage of producing a reduced lactose milk that can be processed, after reduction is completed, in a continuous manner that is identical to non-reduced milk. The disadvantages of this concept include an increase in holding time of the raw milk and vulnerability of the enzyme to proteases associated with the microbial load of the raw milk as well as ensuring completion of lactose reduction within the maximum 72 hour holding period in the plant.

Lactase addition after pasteurization is advantageous due to an increase in efficacy of the enzyme from a reduction in the microbial load and more time available for reaction. The disadvantage of this application is that a holding time at the enzyme's optimum temperature (30-35° C. for *K. lactis*) or lower is required after pasteurization to achieve the desired level of lactose reduction, after which the product goes through a second heat treatment to inactive biological contaminants that accompany commercial treatments of lactase and to stop lactose reduction if the desired level has been achieved. An alternative approach to the addition of lactase after pasteurization has been to inject a very small amount of yeast lactase through a sterile, 0.22 μm filter into UHT sterilized, packaged milk. The UHT product can be stored at room temperature, achieving complete hydrolysis in 7 to 10 days.

Lactase-Based Bioactive Systems
Immobilized Lactase for Industrial Reactors

Immobilized enzyme reactors have been utilized by the food industry to reduce the cost of enzymes during processing by binding the enzyme to an insoluble support. The advantages of immobilization include reuse, stability enhancement, and separation from the product. The enzyme may be conjugated to surface of the support by covalent bonding, ionic attachment, or hydrophobic interactions. The enzyme may, also, be incorporated into a polymer backbone during polymerization or physically entrapped in the bulk of a material. Lactase and whole cells contain lactase have been immobilized to a variety of supports by adsorption, entrapment, and covalent conjugation (see Table 1 and Table 2, infra). Though immobilized enzyme systems have many advantages, they are limited in practice by enzyme leakage, fouling, cost, enzyme activity, carrier stability, and microbial growth. Fouling can occur in both filtration membranes and in porous beads by constituents such as proteins found in milk, which limits the accessibility of substrate to the enzyme. For fluid milk, which has neutral pH, microbial growth is encouraged on immobilized supports. Sanitation of enzyme carriers is necessary to provide consumer safety, but is difficult and may lead to loss of enzymatic activity. For immobilized lactase, cleaning methods have been developed for immobilized *A. oryzae* (SEQ ID NO: 1) lactase using substituted diethylenetriamines.

TABLE 1

Immobilization of lactase

| SUPPORT | TYPE OF LACTASE | METHOD OF IMMOBILIZATION | |
|---|---|---|---|
| Phenol-formaldehyde resin | *A. niger* | Adsorption/glutaraldehyde | 70% hydrolysis of lactose |
| Porous alumina | *A. niger* | Adsorption/glutaraldehyde | 70-80% hydrolysis |
| Phenol-formaldehyde resin | *A. niger* | Adsorption/glutaraldehyde | 25 mg/g; 220 U/g |
| Egg shell | *Lactobacillus bulgaricus* | Adsorption/glutaraldehyde | 25% maximum activity |
| Phenol-formaldehyde resin | *B. circulans* | Adsorption/glutaraldehyde | 225 U/g (wet) |
| Phenol-formaldehyde resin | *A. niger* | Adsorption/glutaraldehyde | 250 mg/g; 4000 U/g |
| Egg white powder | *E. coli* | Adsorption/glutaraldehyde | 50% hydrolysis in 8 hrs |
| Feather protein | *A. niger* | Adsorption/glutaraldehyde | 100 mg/g; 300 U/g protein |
| DEAE cellulose | *Scopulariopsis* | Adsorption/glutaraldehyde | 1-2 U/g resin |
| Phenol-formaldehyde resin | *A. niger* | Adsorption/glutaraldehyde | 70-75% hydrolysis |
| Polyacrylamide | *K. lactis* | Hydrophobic bond | 70 U/g |
| Brushite | *E. coli* | Adsorption | N/A |

TABLE 1-continued

Immobilization of lactase

| SUPPORT | TYPE OF LACTASE | METHOD OF IMMOBILIZATION | |
|---|---|---|---|
| Tritylagarose | E. coli | Hydrophobic bond | 75-90% relative activity |
| Nylon-acrylonitrile | E. coli | Covalent-CMC or carbodiimide | 236.5 U/mg; Poor stability |
| Amino-carbonilated cellulose | K. fragilis/E. coli | Covalent-diazo/glutaraldehyde | 3 U/g; 93 U/g |
| Cellulose | E. coli | Covalent-benzo-quinone/oxirane | 109 mg/g, 4130 U/g; 40 mg/g, 1780 U/g |
| Oxirane acrylic | E. coli | Covalent | 40 mg/g, 1300 U/g of carrier |
| Sepharose | A. oryzae (SEQ ID NO: 1) | Covalent | 63.9 U/mg |
| Oxirane polyacrylamide | K. lactis/K. fragilis | Covalent-oxirane | poor results |
| Mn-Zn ferrite particles | A. niger | Covalent-silanization/glutaraldhyde | 1 U/g; 16 U/g |
| Plexiglass-like material | A. oryzae (SEQ ID NO:1) | Covalent | 80% hydrolysis |
| Ion exchange resin | A. oryzae (SEQ ID NO: 1) (purified) | Covalent-glutaraldehyde | 1000 U/g; 80% conversion |
| Cellulose triacetate | K. lactis | Entrapment | 30 mg/g; 22 U/g |
| PVOH | K. lactis | Entrapment | 100% hydrolysis in 200 min |
| Polyacrylamide | Lactobacillus bulgaricus | Entrapment | Maximum 31% activity |
| Collagen | A. niger | Entrapment | 1680 U/g |
| Hollow fibre membrane | K. fragilis | Entrapment | 40% hydrolysis |
| Hollow fibre membrane | K. lactis | Entrapment | 10 mg/930 cm square |

TABLE 2

Covalent immobilization of lactase

| SUPPORT | TYPE OF LACTASE | METHOD OF IMMOBILIZATION | NOTES |
|---|---|---|---|
| Phenol-formaldehyde resin | A. niger | Adsorption/glutaraldehyde | 70% hydrolysis of lactose |
| Porous alumina | A. niger | Adsorption/glutaraldehyde | 70-80% hydrolysis |
| Phenol-formaldehyde resin | A. niger | Adsorption/glutaraldehyde | 25 mg/g; 220 U/g |
| Egg shell | Lactobacillus bulgaricus | Adsorption/glutaraldehyde | 25% maximum activity |
| Phenol-formaldehyde resin | B. circulans | Adsorption/glutaraldehyde | 225 U/g (wet) |
| Phenol-formaldehyde resin | A. niger | Adsorption/glutaraldehyde | 250 mg/g; 4000 U/g |
| Egg white powder | E. coli | Adsorption/glutaraldehyde | 50% hydrolysis in 8 hrs |
| Feather protein | A. niger | Adsorption/glutaraldehyde | 100 mg/g; 300 U/g protein |
| DEAE cellulose | Scopulariopsis | Adsorption/glutaraldehyde | 1-2 U/g resin |
| Phenol-formaldehyde resin | A. niger | Adsorption/glutaraldehyde | 70-75% hydrolysis |
| Polyacrylamide | K. lactis | Hydrophobic bond | 70 U/g |
| Brushite | E. coli | Adsorption | N/A |
| Tritylagarose | E. coli | Hydrophobic bond | 75-90% relative activity |
| Nylon-acrylonitrile | E. coli | Covalent-CMC or carbodiimide | 236.5 U/mg; Poor stability |
| Amino-carbonilated cellulose | K. fragilis/E. coli | Covalent-diazo/glutaraldehyde | 3 U/g; 93 U/g |
| Cellulose | E. coli | Covalent-benzoquinone/oxirane | 109 mg/g, 4130 U/g; 40 mg/g, 1780 U/g |
| Oxirane acrylic | E. coli | Covalent | 40 mg/g, 1300 U/g of carrier |
| Sepharose | A. oryzae | Covalent | 63.9 U/mg |
| Oxirane polyacrylamide | K. lactis/K. fragilis | Covalent-oxirane | poor results |
| Mn—Zn ferrite particles | A. niger | Covalent-silanization/glutaraldehyde | 1 U/g; 16 U/g |
| Plexiglass-like material | A. oryzae | Covalent | 80% hydrolysis |
| Ion exchange resin | A. oryzae (purified) | Covalent-glutaraldehyde | 1000 U/g; 80% conversion |
| Cellulose triacetate | K. lactis | Entrapment | 30 mg/g; 22 U/g |
| PVOH | K. lactis | Entrapment | 100% hydrolysis in 200 min |
| Polyacrylamide | Lactobacillus bulgaricus | Entrapment | Maximum 31% activity |
| Collagen | A. niger | Entrapment | 1680 U/g |
| Hollow fibre membrane | K. fragilis | Entrapment | 40% hydrolysis |
| Hollow fibre membrane | K. lactis | Entrapment | 10 mg/930 cm square |

| SUPPORT | NATURE OF SUPPORT | TYPE OF LACTASE | RETAINED IMMOBILIZED ACTVITY | AMOUNT IMMOBILIZED | NOTES |
|---|---|---|---|---|---|
| Eupergit C | Copolymer of methacrylamide, N,N'-methylen-bis(acrylamide) and a monomer carrying oxirane groups; Macroporous, ~150 um | A. oryzae (SEQ ID NO: 1) | 30% activity | | |

TABLE 2-continued

Covalent immobilization of lactase

| Support | Chemistry | Organism | Activity | Loading | Notes |
|---|---|---|---|---|---|
| Eupergit C-250L | Copolymer of methacrylamide, N,N'-methylen-bis(acrylamide) and a monomer carrying oxirane groups; Macroporous, ~250 um, higher oxirane content | B. circulans | 90% activity | 33 mg/g | increase ionic concentration, increased loading and activity (upto 1M); neutral and basic coupling pH needed; 10-24 hr coupling time; immobilized on Euperit C with higher loading and lower activity |
| Eupergit C-glutaraldehye; Eupergit C-epoxy boronate | Copolymer of methacrylamide, N,N'-methylen-bis(acrylamide) and a monomer carrying oxirane groups; Macroporous, ~150 um | K. lactis | 70-75% | 0.2 mg/g | linked by carbohydrate area decreased product inhibition; >20 hrs immobilization time |
| Sepabeads | Macroporous; polymethacrylate with oxirane | A. oryzae (SEQ ID NO: 1) | no activity | | |
| Sepabeads-Amino-Epoxy | Macroporous; polymethacrylate with oxirane | A. oryzae (SEQ ID NO: 1) | 3500 U/g | Unclear (28-40 mg/g) | >20 hrs reaction time for complete immobilization |
| Graphite | Graphite modified using anhydrous methanol to introduce carboxyl groups | K. lactis | 8800 X decrease in activity | 0.63-1.30 mg/cm square | |
| Cotton | Tosylated | A. oryzae (SEQ ID NO: 1) | 55% | 50 mg/g | |
| Cotton fibers using PEI aggregates | Glutaraldehyde cross-linked | A. oryzae (SEQ ID NO: 1) | In slurry, high activity; After centrifugation, low activity; Immobilized activity is unclear | 250 mg/g | Cotton was immersed in PEI, then enzyme added which aggregated the protein, all was crosslinked |
| Chitosan | Glutaraldehyde cross-linked | A. oryzae (SEQ ID NO: 1) | ~100% | unclear (0.1 mg/g) | |
| Chitosan | Glutaraldehyde cross-linked | K. fragilis | 11-40% | 17-20 mg/g | K. fragilis is notoriously unstable |
| PVOH-formaldehyde | tosy sulfony chloride, cyanuric chloride, benzoquinone | A. oryzae (SEQ ID NO: 1) | 26-100% | | |
| Salicylic acid, resorcin, formaldehyde | tosy-sulfonyl chloride, cyanuric chloride, benzoquinone | A. oryzae (SEQ ID NO: 1) | 14-28% | | |
| Phenol-formaldehyde resin (plexiglass) Porous silica | glutaraldehyde | A. niger | 200 umol/min/g of support; 40% | 5 mg/g | |
| PVC/silica | PEI/glutaraldehdye | A. oryzae (SEQ ID NO: 1) | 90% | 1.9 mg/cm2 | ribbed increases SA; rolled over like a capet around a poll |
| Nylon | Glycidyl methacrylate (diazotisation) glutaraldehyde | A. oryzae (SEQ ID NO: 1) | 48-62% Vmax | | |
| Cellulose | Epichlorohydrin | K. fragilis | 80% | Unclear | epoxy residues have a slow reaction, and it has been suggested by others (Mateo) that adsorption prior to covalent modification helps |
| Sepharose 4B | Agarose; 1-Cyano-4-(dimethylamino)-pyridinium tetrafluoroborate | K. lactis | 77-112% | 1-5.4 mg/ml packed support | cyanating protein sulfhydryl groups; also works on amino |
| Controlled Porous Glass | 3-aminopropyltriethoxysilane activated with glutaraldehyde | K. fragilis | 90% | Unclear | lactase cultured in lab |
| Siliva/alumina | aminopropyltriethoxysilane activated with glutaraldehyde | K. fragilis | 50% | | |
| CPC/silica | aminopropyltriethoxysilane activated with glutaraldehyde | K. lactis | 8-34% | 12.6-23 mg/ml packed support | |
| Gelatin | glutaraldehyde or chromium (III) acetate | E. Coli | 22-25% | | |

TABLE 2-continued

Covalent immobilization of lactase

| DEAE Cellulose | glutaraldehyde | *Scopulariopsis* | 6x more activity that dulolite | | |
|---|---|---|---|---|---|
| Cellulose beads | Benzoquinone | *E. Coli* | 23-83% | 13-109 mg/g | high load reduced activity but increased stability. MW of *E. Coli* lactase = 540,000 |
| Nylon/acryllmide | glutaraldehyde and azide | *E. Coli* | 156 U/g | assumed 2 mg/g based on activity | suggested poor surface grafting |
| Silica•Alumina | Diisocyante | *A. niger* | 100 fold decrease | | |

Enzyme leakage and loss of activity over time has been demonstrated for entrapment and adsorption-based systems due to continuous processing. Covalent modification of the enzyme to or within a support has been explored as an approach to overcome the problem of enzyme leakage (see Table 2, supra). Different supports and methods of immobilization are developed so as to maintain/enhance enzyme activity, increase enzyme loading, lower the cost of immobilization, and optimize compatibility with a reactor design. The carrier (and support chemistry) must, also, be nontoxic, approved for food use, and, for covalent immobilization, have functional groups available for bioconjugation. For lactase immobilization, compromises are made to minimize or maximize these factors, and though some systems have been developed for industry, application to dairy processing has been allusive.

The nature of the support on enzyme activity is difficult to determine in part because of lack of free enzyme controls for comparison. Hydrophobic supports have been suggested to reduce the activity of the enzyme because of hydrophobic adsorption and complimentary unfoulding of the enzyme at the surface. Hydrophilic natural carriers including agarose, cellulose, dextran, alginate, gelatin, and collagen have been used with high activity retention. Hydrophilic carriers, though useful at the lab scale, are often not suited for industrial processing because of low mechanical rigidity (deformation), biodegradation, and swelling in aqueous solutions—leading to complications associated with pressure drops. Inorganic carriers including silica and glass have, also, shown promise with respect to activity retention. These supports have been used for industrial processes, but are limited by cost and pH stability.

Active Packaging

The growing trend in consumer demand for fresh, minimally processed, natural convenient foods with fewer additives along with changes in retail and distribution practices, has presented challenges to the food-packaging industry. In response to these trends and due the inherent limitation of traditional packaging systems to meet those demands has resulted in the development of active packaging applications. Active packaging involves interactions between a food, packaging material and the internal gaseous atmosphere. The goal of these systems is to, through the entrapment, absorption, or covalent linking of functional compounds to or within packaging materials, increase the quality and/or safety of the product after packaging. Such packaging changes the condition of the packaged food to extend shelf-life, or improve food safety or sensory attributes, while maintaining the quality of the packaged food. In this context, the polymer no longer has just passive properties as dictated by the chemical and physical structure, but also an active component that has been deliberately designed to serve a specific function in the food system Enzymes that have been incorporated for active packaging include lysozyme, glucose oxidase, and nariginase. Lysozyme, an antimicrobial enzyme that is able to hydrolyze the β(1-4) linkages between N-acetylmuramic acid and N-acetylglucosamine, aiding in the break down of the cell wall of gram positive bacteria, has been immobilized on poly(vinyl alcohol) beads, nylon 6,6 pellets, and in cellulose triacetate films. Though all polymers demonstrated activity, the cellulose triacetate films showed the greatest efficiency, retaining 60% of their activity after 20 uses, and were showed to be inhibitory and bactericidal against *Micrococcus lysodeikticus*. Naringinase, which hydrolyzes the bitter compound naringin to naringenin and prunin, has been immobilized in cellulose acetate and cellulose triacetate polymers. The films showed a decrease in $K_m$ value, indicating an increase in the substrate affinity of the enzyme entrapped films. The films had an activity efficiency of up to 23% compared to the free enzyme at 7° C. Glucose oxidase, which converts glucose, oxygen, and water, to a glucono-delta-lactone and hydrogen peroxide, has been used in sachets and to perform as an oxygen scavenger. A difficulty with this system is that glucose must be available to serve as a reactant for the enzyme to perform as an oxygen scavenger, thus limiting its application thus far.

Lactose-reducing, heat sealable, packaging films have been by developed by lactase entrapment in ethylene(vinyl acetate) and covalently bound to poly(ethylene) with reduced activity upon immobilization. The enzyme has been attached to oxidized polyethylene films using a PEG intermediate and PEI-bound layer. Though the PEG-intermediate did not demonstrate activity, the PEI intermediate did retain measurable activity. A PEG-modified and native lactase has been entrapped in ethylene(vinyl acetate) films with both enzymes exhibiting a significant increase in $K_m$ and decrease in $V_{max}$, but with detectable enzymatic activity. PharmaCal, Ltd has reported the use of an active packaging system using incorporated lactase that could reduce lactose 30-70% in 24-36 hours.

Loss of Enzyme Activity on Surfaces

The organization on an enzyme is that of a primary structure of covalently linked amino acids that form, along the sequence, globular, helical, and sheet folds based on hydrogen bonding (secondary structure). A tertiary structure is formed by the interactions of secondary structures—forming salt bridges, maximizing hydrophobic interactions, and satisfying requirements with the solvent. These interactions, also, form the basis of the catalytic cleft of the protein for enzymatic activity. The tertiary structure gives the enzyme a core of hydrophobic amino acids (phenylalanine, tyrosine, etc.) since exposure of these residues to a native hydrophilic environment would be unfavorable and a surface composed of hydrophilic and acid or basic amino acids because of their ability to hydrogen bond, and contains a bound water layer at the surface. In some cases, a quaternary structure is formed by noncovalent interactions of multiple subunits of same or different sizes.

The complexity of enzymes, though optimal for biological substrate specificity, presents challenges in the development of industrial applications. Enzymes have evolved to function under the conditions of their natural environment, and activity and stability are, subsequently, a reflection of that environment. The pH, temperature, intracellular or extracellular nature of the enzyme, protein concentration, molecular composition of the environment, salt concentration, water activity, substrate concentration, cellular function, and structure hierarchy may all influence the robustness of the enzyme and how it performs. Removing an enzyme from its native environment for use in a designed system changes the dynamics of the molecular equilibrium between the native and unfolded state of the enzyme. This equilibrium can be thermodynamically represented in the Gibbs Free Energy Equation (Equation 1, below)

$$\Delta G = \Delta H - T\Delta S \qquad \text{Equation 1}$$

The equation can be expanded to include enthalpy ($\Delta H$) terms for protein interactions, solvent interactions, and interactions of the two, as well as entropy ($\Delta S$) terms for both the protein and the solvent (Equation 2, below)

$$\Delta G = \Delta H_{solvent/solvent} + \Delta H_{protein/protein} + \Delta H_{protein/solvent} - T\Delta S_{solvent} - T\Delta S_{protein} \qquad \text{Equation 2}$$

For enzymes at a surface, the equation can be expanded further to include the insoluble surface (Equation 3, below)

$$G = \Delta H_{solvent/solvent} + \Delta H_{protein/protein} + \Delta H_{surface/surface} + \Delta H_{protein/solvent} + \Delta H_{protein/surface} + H_{surface/solvent} - T\Delta S_{solvent} - T\Delta S_{protein} - T\Delta S_{surface} \qquad \text{Equation 3}$$

The enthalpy terms account for inter- and intra-molecular interactions that can be changed to influence the enzyme state, including: bond lengths, van der Waals interactions, torsion angle, electrostatic interactions, and hydrogen bonding. The entropy terms indicate the order of the system, with the system favoring more disorder. With respect to an enzyme, dominating entropy will yield multiple, diverse confirmations of an enzyme, which, though energetically favorable, will produce an unfolded and inactive enzyme. Thermodynamic terms must; therefore, be sufficiently satisfied and work in such as way as to prevent unfolding of the catalyst.

Protein interactions at surfaces are studied at the liquid/liquid, liquid/gas, and liquid/solid interface. Proteins, because of their amphiphilic nature, are used in the formation of foams at the liquid/gas interface by denaturing of the tertiary structure to expose hydrophobic residues to the gaseous $CO_2$ and liquid interface. Emulsions, similarly, incorporate proteins to stabilize solutions of oil and water constituents by reducing interfacial tensions and preventing coalescence by electrostatic repulsion. For immobilized enzymes, however, liquid/solid and solid/solid interactions are of importance, and enzyme activity can be lost or maintained due to the thermodynamic effects that occur at the surface interface between the enzyme and the carrier Amino acids that make-up the enzyme are capable of engaging in positive and negative electrostatic attraction and repulsion, disulfide bonding, and hydrophobic interactions—all of which may lower the free energy of the system when in contact with a surface. These groups, along with the hydrogen bonding of the bound water layer and the preferential hydration of a surface, impose restrictions on the nature of a solid interface in preventing loss of the native enzyme structure when the two are in contact.

Proteins with exposed hydrophobic groups have been shown to absorb tightly to hydrophobic surfaces due to lowering of the free energy in aqueous solution that occur from decreased exposed hydrophobic surface area when the two exposed groups come into contact. The hydrophobic interactions cause a dehydration of the protein surface, and the subsequent adsorption presents a shift in the tertiary or secondary structure of the protein. The molecule may then spread across the surface to further minimize the free energy. Both a small or large shift may cause a loss in enzymatic activity. Experiments seeking to characterize changes in enzyme secondary structure at the surface (compared to non-denaturing surfaces) have provided limited information since the shifts, though apparent, appear to be small compared to non-denaturing surface and random from enzyme to enzyme in regards to $\alpha$-helix and $\beta$-sheet perturbations Consequently, changes in the secondary and tertiary structure are difficult to distinguish. Hydrophobic denaturation has been attributed to loss of lactase activity when the enzyme is bound to a porous polymethacrylate resin with oxirane groups.

Electrostatic groups on the surface of a support may lead to attraction or repulsion of ionic amino acids on the enzyme surface. When an enzyme is in contact with the surface, minimization or maximizing those interactions can lead to distortion of the protein and a loss of enzymatic activity. Binding of proteins to charge supports has been shown to occur even when the net charge on the enzyme is the same as the support because of ionizable amino acid side chains. The activity of lactase bound to an anionic support has been shown to be lower than activity when bound to a cationic support, suggesting a negative charge may alter the conformation of the enzyme. Carriers with surface ionic groups can also promote a pH shift in the microenviroment of the immobilized enzyme, which may change optimum catalytic conditions. These extremes in pH can alter protonation state of amino acids causing changes in hydrogen donor/acceptor characteristics, loss or gain or electrostatic repulsions, and changes in salt bridges.

In some instances hydrophilic surfaces have been shown to reduce enzymatic activity to a greater extent than a hydrophobic surface. This phenomenon is attributed to competitive hydrogen bonding at the interface or breaking of necessary salt bridges. The unique structure and chemical properties of water influences the interactions of a surface of an enzyme through hydrogen bond and dipole interactions. The hydrophilic surface changes the enzyme by competing and, ultimately, stripping the water layer from the enzyme shell, which is important from an enthalpic standpoint in maintaining tertiary structure (a hydrophobic surface may also strip the water surface by promoting dehydration—reducing the driving force to retain a hydrophobic residue inside the core).

Changing the chemical/physical nature of a carrier or distance from the surface can influence enzymatic activity, by limiting surface/protein interactions. The addition of the hydrophilic molecules to the surface of a hydrophobic material prevents proteins from adhering by reducing inter and intra-molecular hydrophobic interactions. Hydrophilic molecules, monomers, and polymers have been used to increase the number of functional groups on a surface or to provide a more reactive intermediate. Polyethylenimine, chitosan, polyacrylic acid, heparin, polyalylamine, alginate, and collagen have been grafted, either covalently or ionically, to facilitate protein loading or biocompatibility. The addition of the hydrophilic molecules to the surface of a hydrophobic material prevents proteins from adhering by reducing inter and intra-molecular hydrophobic interactions. Many of these polymers are, also, polyionic under conjugation conditions, which promotes ionic interaction with a charged protein. Initial ionic adsorption coupled with a means of covalent binding has been shown to promote protein loading on a material. A layer-by-layer approach to immobilizing enzyme onto a support has been employed to increase the loading of the enzyme of the carrier or change interactions of proteins with the surface. By this method, a surface layer is formed on an activated support, most often using an ionic polymer. An opposite charged layer is then deposited on top forming a thin layer by ionic attraction and the process is repeated until a desired thickness is achieved. Enzymes may be added between layers or as a final layer on the surface. Polymer brushes have been formed from polymeric surface by using free radical grafting. Glycidyl methacrylate, for example, has been grafted to hollow fiber polyethylene membranes for protein separation technologies by irradiation-induced free radical formation.

When used in a nonaqueous environment, immobilized enzymes can denature by being contact with a hydrophobic liquid or gas surface. To minimize interactions between a solvent or gas bubble, a hydrophilic polymer can be grafted as a thin layer over the enzyme/carrier to create a stable hydrophilic nanoenvironment. Coating of an aldehyde-activated dextrose over glucose oxidase immobilized to a non-porous carrier inhibited inactivation due to gas bubbles. Penicillian acylase was made more stable against dioxane by immobilizing the enzyme through multipoint bonding, followed by creating a hydrophilic environment on the carrier as well as on the enzyme, directly. If dextran was attached to just the carrier or just enzyme, no stabilization occurred indicating the necessity for complete coverage.

Use of spacer molecules such as glutaraldehyde, ethylenediamine, hexamethylene diamine, or poly(ethylene glycol) has been shown to provide an increase in the activity compared to conjugation directly to the support. Increasing the chain length aids in retaining enzymatic activity and the amino groups on a surface aids in the retention of D-amino oxidase activity when conjugated to a support. Likewise, studies in computational protein modeling at interfacial surfaces suggest that a hydrophilic chain on a hydrophobic surface would be necessary to preserve activity of an immobilized enzyme. Trypsin was separated from carboxylic-functionalized fleece by bovine serum albumin (BSA), aldehyde dextran, amino dextran, and PEG-diamine, and direct binding. Use of the spacer molecules showed an increase in activity in all cases relative to direct covalent binding. BSA showed the highest activity retention followed by amino dextran, PEG-diamine, and aldehyde dextran. Though the authors contribute enhance activity to decreased interaction of the protein with the hydrophobic fleece, charge may also be a factor since the surface of the fleece is charged, the aldehyde dextran is activated by periodiate oxidation of the dextran, and the amine spacers carry positive charges. Lactase was separated from an activated nylon support by diamines of varying chain lengths. Increased chain length resulted in an increased activity that was attributed to separation of the protein the densely charged surface. Distance may, also, promote mobility of the biocatalyst to decrease rigidity and allow for better dynamic motion for interaction of the protein with substrate.

Grafting and tethering of polymer chains onto a solid surface is used for increasing the available surface area for protein immobilization, to block activated functional groups on the surface from interaction with a substrate or fluid, and to provide a suitable surface for protein attachment or rejection. The nature of the polymer interface can be changed by grafting a polymer to the surface. Grafting and tethering provides a means of retaining the key bulk properties of a material while changing the surface for biointeractions. The choice of polymer at the surface can alter the interfacial thermodynamics and microenvironment since the enzyme will be reacting with the grafted layer, providing a more suitable platform for enzyme immobilization. Chitosan and collagen, for example, have been used to change the interface of hollow fiber membranes and nanofibers for lipase immobilization.

Self assembled monolayers (SAMs) are thin films of biological or chemical molecules that form spontaneously on surfaces. SAMs differ from graft in that the coverage formed by SAMs is an organized coverage consisting of a true monolayer, which may or may not be covalently grafted. Surface/substrates that form SAMS are limited—examples including alkanethiols on metal surfaces (particularly gold) and alkanesilanes on silicon. Alkanethiols have been shown to form a self assembled monolayer on the surface of gold by oxidative addition/reductive elimination. Alkanesilanes, likewise, self assemble on silicon oxide or silica glass. With respect to enzymes on carriers, SAMs with, different pendant groups, have been used to elucidate the mechanism for loss of glucose oxidase activity when adsorbed to a surface.

Multipoint covalent bonding is an alternative to surface modification and has been used to enhance enzyme stability in porous carriers by, three-dimensionally, fixing the enzyme in place so as to restrict movement and denaturation associated with entropy. Several enzymes have shown increased stability when applying this method. The activity retention associated with this method, which typically incorporates, a porous agarose carrier containing glycoxal residues, may be as low as 10-15%, or a high as 100%. Proper geometric alignment for the enzyme and the carrier is a limitation for this approach, and may lead to deactivation of the enzyme.

Physical Effects

The quaternary structure of an enzyme develops when subunits associate in a noncovalent manner. The association/disassociation of the subunits is dynamic, which can be problematic when conjugating to a planar surface where all the subunits may not contact the surface to be immobilized. Multipoint bonding in porous support if often effective for dimmers, but greater subunit associations may require a post-immobilization stabilization using an activated polymeric molecule. The quaternary structure of alcohol oxidases, with 4-8 subunits, were stabilized by a two step immobilization process of 1) attaching the enzyme to a porous support and 2) conjugating aldehyde-dextran to the enzyme/support. Though activity was reduced to 20%, quaternary structure (as determined by protein loss from the support in the presence of SDS and mercaptoethanol and analysis of the supernatant by electrophoresis) was maintained. In the same study, polyethylenimine (PEI) was used as a grafted layer, showing no loss of quaternary structure 50% activity retention when adsorbed to the support. The enzyme; however, retained more activity on the base agarose support (80%) prior to quaternary structure stabilization approaches. Tetrameric L-asparaginase was coupled to agarose-glutaraldehyde supports followed by conjugation with aldehyde-dextran. Then enzyme lost 60% of the intrinsic activity, but could be subjected to boiling SDS without loss of protein—demonstrating retention of the quaternary structure. Catalase from bovine liver on agarose beads showed full retention of activity; however, after washing, enzyme activity decreased and was attributed to loss of enzyme subunits in the rinse. Modification with aldehyde-dextran after immobilization caused a 30% reduction in enzymatic activity, but no loss of protein. Effects of washing on residual activity after immobilization; however, was not evaluated.

Crosslinking enzymes in solution to form carrier-free oligomeric microstructures are used to increase enzyme activity per unit area, provide enhanced thermostability and solvent stability, and stabilize quaternary structure. Cross-linked enzyme crystals (CLECs) are formed by cross-linking the crystallized structure of an enzyme to "freeze" the structure in place. Cross-linked enzyme aggregates, in a similar fashion, are formed by forcing enzymes to aggregate, by addition of salt or organic solvent, and cross-linking the structure. Glutaraldehyde is often used as the crosslinking agent because of its wide reactivity. CLECs/CLEAs can be used alone as an insoluble enzymatic platform or conjugated to a carrier. The limitations of CLEC/CLEAs are the small size, conditions for cross-linking, diffusion limitations, and deformation under mechanical stress. CLECs/CLEAs have been prepared for a number of enzymes, often resulting in greater stability under denaturing conditions. Chloroperoxidase, subilisin, theromolysin, and lipase have been crosslinked as CLECs or CLEAs. CLEAs of lipase have been immobilized in polymeric membranes to prevent leaching from the membrane without having to activate the support for covalent attachment. The process was carried out by allowing the enzyme to enter the membrane and then transferring the membrane to a solution of glutaraldehyde. Catalase, which is unstable in solution because of disassociation of the quaternary structure, was modified with glutaraldehyde—producing a stable conjugate. Though not an ideal CLEA, lactase has been aggregated on the surface of cotton by adding a PEI layer to the cotton, and not removing the excess PEI. When lactase is added, followed by glutaraldehyde, the lactase complexes in the PEI, and an aggregate PEI-lactase is formed.

Site directed orientation of an enzyme on a support can be useful in preventing non-specific adsorption of the protein and alignment of the active site towards the surface, and is particularly beneficial for enzymes acting on large polymeric substrates. Protein engineering has been used to introduce a cysteine residue on the surface of opposite the catalytic site to enhance to activity of immobilized subtilisin by rational design. A point mutation is achieved by substituting the codon calling for a cysteine residue at the desired place in the gene sequence, and introducing the gene into an expression vector to produce the new protein. His-tagged enzymes are proteins that have genetically engineered by introducing a sequence calling for histidine residues (usually six) at the C- or N-terminus. The histidine sequence reacts specifically with divalent metal cations. By covalently attaching a metal chelating agent like Ni-nitriloacetic acid (NTA), and introducing $Ni^{++}$, a site-specific interaction will form between the chelating agent, nickel, and the histidine sequence. Polyhydroxyalkanoate was immobilized by this method to silicon for the production of aliphatic polyesters. Another example of site-specific immobilization is that of cutinase, a serine esterase, which forms a covalent bond with phosphonate inhibitors and is specific to this enzyme. Some enzymes are glycosylated and can be conjugated to a support specifically by the carbohydrate moiety. Lipase has been immobilized in this fashion by periodate oxidation of the carbohydrate chain for conjugation to Eupergit C supports. Taking advantage of the pKa difference in the N-terminus has been used to site-specifically attach proteins to PEG. General bioconjugation schemes, targeting the same amino acid group can, likewise, result in different retention in enzyme activity. This phenomenon may be due to the specificity of the bioconjugation reagent with the desired amino acid groups.

Reducing the size of the carrier to the nanoscale has shown to promote increased activity of an immobilized enzyme, due to either increased Brownian motion or a reduction in protein conformational changes upon immobilization The effect of particle size was demonstrated using α-Chymotrypsin attached to polystyrene particles of 100-1000 nm as well as thin films of polystyrene. Though the change was slight for the nanoparticles, $k_{cat}/K_m$ was 100 fold lower on the films, which the authors attributed to mobility effects of the catalyst Inhibition of enzyme conformational changes has, also, been attributed to the advantageous geometry of nanomaterials. Soybean peroxidase deactivation was measured after adsorption to single walled nanotubes (SWNTs) and graphite flakes. The deactivation kinetics of the enzyme was lower on the SWNTs and demonstrated to be independent of protein coverage, while the graphite flakes were dependent on protein coverage. It was concluded that denaturing lateral protein-protein interactions were decreased due to the size and curvature of the SWNTs.

The porosity of a carrier can effect apparent enzyme activity by increasing $K_m$ of an enzyme in a three dimensional medium. Diffusion limitations of the substrate can be effected by the microenvironment of the carrier/solvent, inaccessibility of substrate into the pores, or blockage of available enzyme. Likewise, the microenvironmental pH can effect how the substrate interacts with the carrier-bound enzyme. Trypsin showed a 2-unit pH shift for activity when immobilized in a carboxylic acid matrix.

Ordering of the protein on the surface can alter the activity of the conjugated enzymes. Crowding of protein on the surface of a support with increase loading has been shown to reduce the activity of the enzyme due spatial restrictions, limited active site accessibility, or denaturing of the protein. Polymethylmethacrylate (PMMA) with an irregular surface compose of it-PMMA or an order surface of alternating it- and st-PMMA (which forms regular helical structures) was used to study immobilization of lactase (E. coli). The PMMA with the ordered surface resulted in the retention of greater lactase activity. This result was attributed to enthalpic gains associated with polymer mobility, and weak/limited interactions between the enzyme and alternating surface that limited these enthalpic gains.

Carrier and Enzyme Modification
Surface Modification

Functionalization of materials by copolymerization, wet chemistry, and physical-chemical methods are employed to change the characteristics of a surface or develop a surface more suitable for bioconjugation. Introduction by copolymerization insert a monomer with an inert side chain to be polymerized with a polymer containing a functional group. Polystyrene microspheres have been successfully prepared using carboxylic acid, amine, and hydroxyl monomers. Wet chemistry techniques make use of chemical groups in the polymer side chain (i.e. hydroxyls, esters, amines, aldehydes, and carboxylic acids) or by introducing groups for an inert surface such as oxidation or nitrosylation. Physical techniques such as oxygen and nitrogen plasma oxidation, corona, and UV treatment have, also, been instrumental in modifying a polymer surface and are used in a number of industries including food applications. These methods have provided a means to conjugate bioactive compounds to polymeric supports.

Enzyme Modification

Biological methods of enzyme modification are focused on manipulation of the enzyme at the genetic level. Transformations in the gene and corresponding protein structure are either random (directed evolution) or intentional (rational design). Directed evolution relies on methods such as error-prone PCR and DNA shuffling. epPCR utilizes polymerase to introduce random mutations in a gene. DNA shuffling uses a number of homologous genes with desired characteristics. The genes are fragmented, denatured, and annealed in random fashion. For both epPCR and DNA shuffling, the new genes are introduced in an expression vector and the corresponding protein screened for a desired property. Directed evolution has produced a number of enzymes with enhanced specificity, activity, and thermostability. The method, though quick and powerful, requires large libraries of genes and multiple generations of protein producing microorganisms with no guarantee of enzyme improvement. Rational design is a technique where an intentional modification is introduced in the sequence of the gene to alter the protein. The practice aims to go from desired function to structure to sequence. Compared to directed evolution, rational design has fewer successes, attributed to the idea that knowledge of structure function of enzyme is still developing.

Chemistry-driven modifications are employed to change the surface interactions between the enzyme and the external environment, adjust enantioselectivity and/or specificity, prevent unwanted interactions, or explore structure/function relationships. Engineering in this category include the use of surfactants, reverse micelles, extraction, and covalent modification. Surfactants may be used by directly incorporating a lyophilized protein into a solvent containing surfactant and small amounts of water. The continuous solution is then centrifuged and the supernatant removed. This method has shown 25-72% solubility of enzymes in a number of solvents of varying polarity as well as protein aggregation of up to 100 molecules.

Reverse micelle containing enzyme are produced by dissolving an aqueous solution of enzyme in an organic solvent containing a surfactant. The self-assembled micelles encapsulate enzyme and can be separated by centrifugation. This method allows some water to be associated with the system, which may increase the unfolding of the enzyme. Protein extraction is a unique techniques that involves ion-pairing an enzyme with a small molecule, which can be paired with a surfactant molecule and extracted into an organic layer. The method has been used with up to 95% solubilization of an enzyme, and can be applied in crosslinking an enzyme during monomer polymerization.

Polymer conjugation may be used to make the enzyme surface more hydrophilic or hydrophobic to induce solubility or thermostability. This technique utilizes single polymer chains or small molecules to attach to the surface of the enzyme. The most commonly polymeric molecules for covalent modification are carbohydrates (i.e., cyclodextrans, pectin, chitosan, carboxymethylcellulose, and sucrose) and poly(ethylene glycol). A procedure of interest for that has been utilized for the enhancement of therapeutic proteins and peptides is PEGylation, which unlike many other modifications provides simple, clean, and specific attachment chemistry for protein derivatives with low toxicity. PEGylation involves the attachment of polyethylene glycol (PEG) to a functional group of a compound so as to induce a variety of alterations to the protein including decreased immunogenicity, increased half-life due to reduced proteolysis, increased thermostability, and alterations in the solubility properties, which allows the protein to be soluble in water, toluene, 1,1,1 trichloroehane and benzene, and insoluble in ethyl ether. Factors influencing these properties are the number of PEG molecules attached, the molecular weight and structure of PEG chains attached, the location of PEG sites on the protein, and the chemistry used.

The solubility of enzymes in organic solvents is enhanced upon attachment of PEG, and PEGylation nearly always increased solubility. An increase in benzene solubility of catalase is also accompanied with increasing degree of PEG-modification. There is indication that PEG-modified enzymes catalyze reactions in hydrophobic media and, in some cases, affinity for the substrate and velocities are increased in such, but there is little evidence to suggest whether this increase is due to stabilizing effects of PEG, solubilization that increases protein-substrate interaction, or a synergistic effect. The thermostability of effects of PEG on protein stabilization has been well documented, with a number of enzymes having demonstrated an increased thermostability after being modified with PEG. A detailed study on the thermostability of three enzymes after modification by glycosalation and by PEGylation showed that glycosylation increased hydrophilicity of the enzymes while PEG made the enzyme more hydrophobic. Under heat denaturing conditions, the glycosylated enzymes lost more activity over time compared to the native enzymes, but PEGylated enzymes showed an increased stability over time. These results were attributed to the ability of PEG to draw water from the system to be utilized by the shell, but also increasing interaction of water with hydrophobic clusters, preventing access to the enzyme surface. Other studies, however, have shown that an increase in enzyme thermostability upon modification with polysaccharides, though similar mechanisms for enzyme stability may be attributed to these modifications as well.

Small molecules have been used to study structure function relationships of enzymes and to alter the stability of the proteins. Molecules are often attached to thiol or ionic groups of the enzyme because of the reactivity; however, modifications of these groups may lead to inactivation of the enzyme. Chymotrypsin has been glycosylated to promote stable oligomeric structures of the enzyme. The enzyme, RNase A, has also been glycosylated with glucosamine to explore thermostability of the enzyme. Immobilized lipase has been aminated with EDC/ethylenediamine to change the selectivity of the enzyme. Though selectivity change, intrinsic activity was reduced by 70%. The amine and carboxylic acid groups of penicillin G acylase were converted to opposite charge by amination of the carboxylic acid groups with ethylenediamine or succinylation of the amine groups with succinic anhydride. The modifications were performed to increase loading of the enzyme on ion exchange resins without dramatic changes to enzyme activity.

BRIEF SUMMARY OF THE INVENTION

It is therefore a principal object and advantage of the present invention to retain a higher percentage and quality of lactase enzymatic activity by attaching lactase to a hydrophobic polymer support than is provided by currently available technology, and to provide methods associated therewith and products made from the disclosed methods.

It is a further object and advantage of the present invention to covalently conjugate enzymes such as lactase to hydrophobic polymer supports in a manner that retains enzymatic activity.

It is also an object of the present invention to develop methods for retaining/increasing intrinsic enzyme activity after attachment to hydrophobic polymer supports.

It is a further object and advantage of the present invention to determine the causes of lactase activity loss upon conjugation to a carboxylic acid-activated, hydrophobic carrier.

It is also an object and advantage of the present invention to apply the systems and methods of an embodiment of the present invention to the development of lactase-immobilized packaging films.

It is an additional object and advantage of the present invention to provide active packaging technologies that utilize surface modification and bioconjugation chemistries to develop materials to which bioactive compounds that may have use in food packaging could be covalently attached.

It is also an object and advantage of the present invention to provide an active packaging technology where lactase is covalently attached to the surface of a common food contact polymer, e.g., polyethylene, in which containing food lactose continues to be processed by lactase post-packaging.

It is a further object and advantage of the present invention to covalently attach lactase to a common food contact polymer where it is unlikely to migrate to the food contained in the active package, and thus is unlikely to be consumed.

In accordance with the foregoing objects and advantages, an embodiment of the present invention provides a method for retaining enzyme activity after attaching lactase to a hydrophobic polymer support. The method includes introducing a more compatible, natural polymer spacer between the enzyme and the support that serves as a "cushion" layer. The hydrophilic graft aids in the retention of enzyme activity and stability, while the hydrophobic core support provides mechanical strength, low cost, and durability. According to various aspects of an embodiment of the present invention, there are disclosed a system and a method pertaining to combining a hydrophobic support with a hydrophilic cushion attached to the enzyme.

In accordance with an embodiment of the present invention, a method is provided for covalently immobilizing lactase from *Aspergilus* oryzae, for example, onto a hydrophobic support via a grafted hydrophilic layer, after which, up to and including 70% of the enzymatic activity is retained under optimal conditions.

In accordance with an embodiment of the present invention, a method for the continuous production of lactose-free or lactose-reduced milk and associated products is provided. An embodiment of the present invention is also directed to lactose-free and/or lactose-reduced milk and/or a lactose-free and/or a lactose-reduced milk product.

In accordance with an embodiment of the present invention, a method directed to blocking of enzyme carboxyl for immobilization of the enzyme to charged supports is provided. A particular aspect of an embodiment of the present invention is directed to blocking of enzyme carboxyl groups of β-galactosidase (lactase) from *Aspergillus* Oryzae for immobilization to acrylic acid/polystyrene supports.

In accordance with an embodiment of the present invention, a hydrophobic core comprising a polystyrene/acrylic acid copolymer is provided. The hydrophobic core may have one or more of the following advantages: provides mechanical strength; resistant to excessive swelling and dissolution in an aqueous environment; simple to produce/material readily available; able to be manufactured into spheres of varying sizes; FDA approved; contains functional groups that can be used for further modification; and has a negative charge in weak acidic, neutral and basic solutions which increases grafting potential.

In accordance with an embodiment of the present invention, a hydrophilic layer of chitosan combined with a hydrophobic core is provided. The hydrophilic layer may have one or more of the following advantages: provides a natural hydrophilic "cushioning" for the enzyme to prevent denaturation at the surface of the hydrophobic core; inexpensive; FDA approved; multiple amine groups to serve as points of attachment to the support and the enzyme; antimicrobial properties when attached to a surface; positively charged under the conditions of conjugation to increase adsorption to the negatively charged core and allow for adsorption of the negatively charged enzyme (e.g., PI 4.5); and a low pKa (e.g., 6.5) enables the polymer to be neutral at the pH of fluid milk (6.8), preventing nonspecific ionic adsorption of milk components.

In accordance with an embodiment of the present invention, polymer films that can be used for in-package processing of food, and to which bioactive compounds such as enzymes can be covalently attached, are provided. In a preferred embodiment of the present invention, the polymer films comprise low density polyethylene films, wherein the low density polyethylene films are surface functionalized.

In accordance with an embodiment of the present invention, a method comprising covalently attaching β-galactosidase (lactase) to surface functionalized low density polyethylene films is provided. The method further comprises a two-step wet chemical functionalization which introduces primary amines to the film surface (e.g., 15.7 nmol/cm2 primary amines). Changes in film surface chemistry after each step in the process of attachment can be characterized by contact angle measurements, dye assays, X-ray photoelectron spectroscopy, and appropriate protein assays. The method further comprises using glutaraldehyde to covalently attach lactase to the surface (e.g., at a density of 6.0 µg protein per $cm^2$) via reductive amination.

In accordance with an embodiment of the present invention, a product comprising an enzyme covalently attached to inert polymer surfaces, adapted to retain significant activity, and thus can be adapted for non-migratory active packaging materials is provided. In a more preferred embodiment, a product comprising lactase covalently attached to functionalized polyethylene is provided which is adapted to withstand heat treatment in the presence of an ionic denaturant. The product can provide up to an including 74% enzyme retention, suggesting that migration of the enzyme into the food product would be unlikely. The resulting polyethylene can be adapted to provide an enzyme activity of about 0.020 lactase units (LU)/cm2 (approximately 4500 LU/g).

In accordance with an embodiment of the present invention, a method comprising covalently attaching the enzyme β-galactosidase (EC 3.2.1.23) (e.g., from *Aspergillus oryzae*) to a polystyrene/acrylic acid microspheres (1 µm in diameter) via a grafted chitosan linker is provided. The enzyme can retain, for example, 70% to 90% of the activity of the soluble enzyme under optimal conditions with a loading of about 60 mg of enzyme/g of support. A product comprising the enzyme, immobilized as described, is also part of an embodiment of the present invention, as well as the method of using the immobilized enzyme and the resultant lactose reduced and lactose free milk products.

In accordance with an embodiment of the present invention, a method of conjugating lactase (*A. oryzae*) (SEQ ID NO: 1)to polystyrene-co-acrylic acid microspheres via carbodiimide chemistry. It was recognized that this conjugation or immobilization could result in a decrease in enzymatic activity compared to the intrinsic specific activity. It was also recognized that increasing the density of surface carboxylic acid groups on the carrier yielded a further reduction in specific activity.

In accordance with a further embodiment of the present invention, a method comprising blocking of the carboxylic acid-bearing amino acids of lactase with glucosamine is provided, which produced no significant change in free enzyme activity, but yielded an increase in specific activity compared to the unblocked enzyme when conjugated to the microspheres. The method further comprises the modification of enzyme carboxylic acid groups, which also aided in the retention of specific activity when immobilized to oxidized to low density poly(ethylene) films.

In accordance with a further embodiment of the present invention, a method comprising changing the surface properties of polystyrene-co-acrylic acid microspheres by tethering chitosan (β-1-4-poly-D-glucosamine) is provided, which resulted in increased protein loading to the support with no significant change in specific activity compared to the free enzyme under optimum conditions. It was recognized that retention of lactase (A. oryzae) activity upon conjugation to carboxylic acid functionalized hydrophobic carriers is dependent on the interfacial influences associated with the density of carboxylic acid groups on the surface of the support. It was also recognized that, pursuant to a method of an embodiment of the present invention, altering interactions of the carrier-protein interface by modifying enzyme carboxylic acid groups or changing the surface characteristics of the carrier promotes structural stabilization and retention of lactase specific activity. These methods of an embodiment of the present invention can be applied to the development of a lactase-reducing food packaging film or an economically feasible polymer-based immobilized enzyme reactor system.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 10:
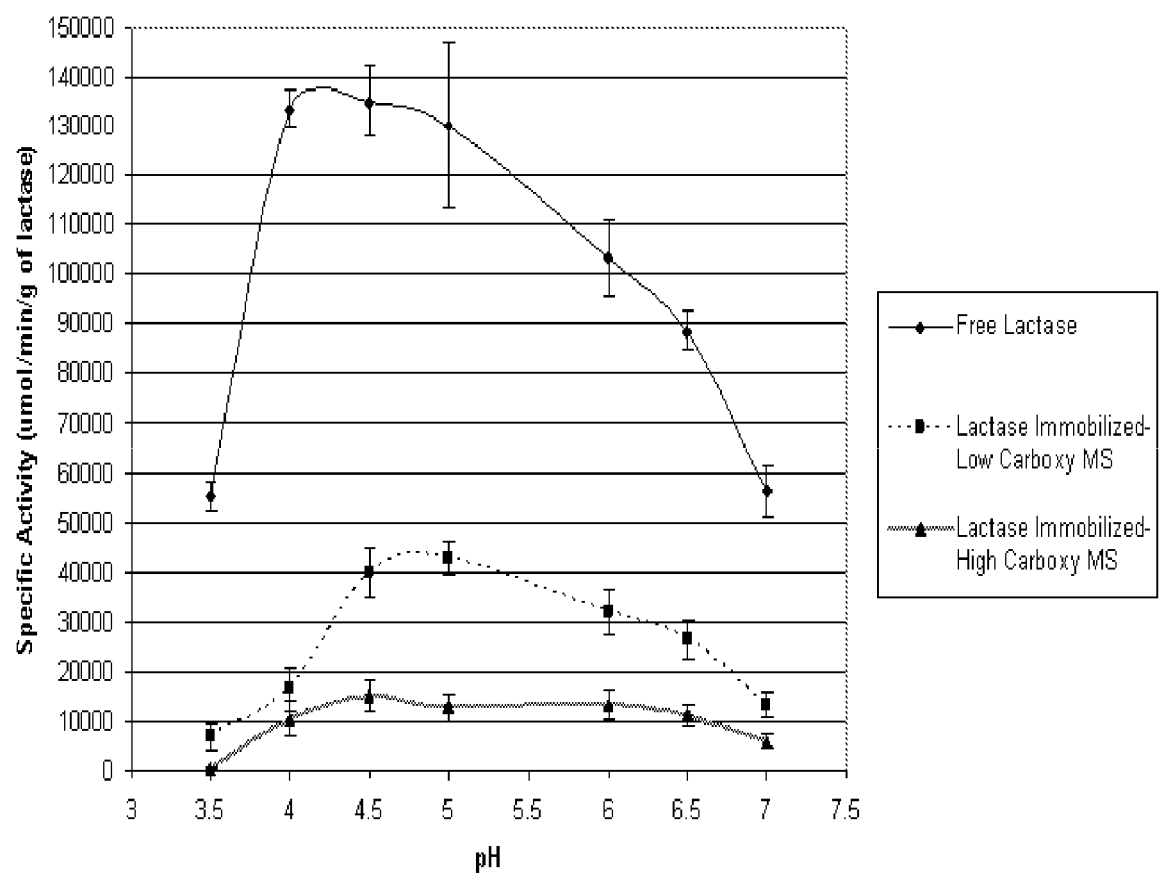

FIG. 10 is a graph showing the effect of pH on free lactase (*A. oryzae*) (SEQ ID NO: 1) and covalently immobilized lactase on low carboxylic acid polystyrene-co-acrylic acid microspheres (1.2 um; 87 Å2 between carboxylic groups) and high carboxylic acid polystyrene-co-acrylic acid microspheres (1.1 um; 6.2 Å2 between carboxylic groups) at 50° C. using ONPG as enzyme substrate. Values represent mean values±standard deviation (N=3).

Figure 11:
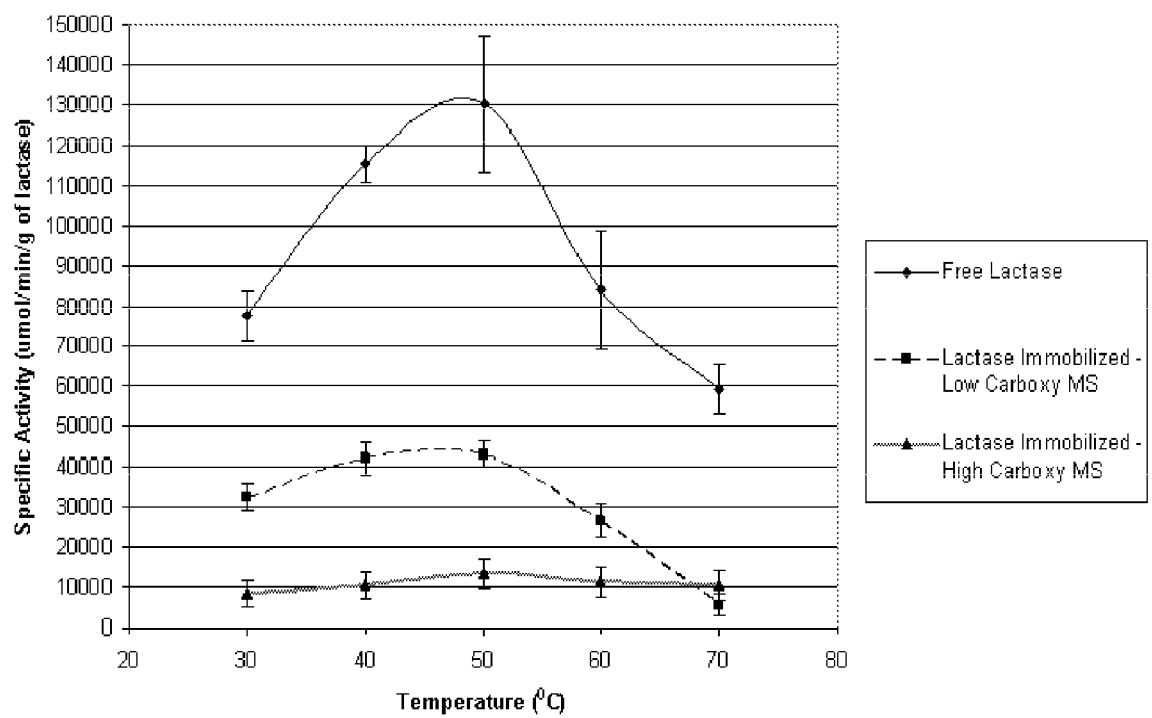

FIG. 11 is a graph showing the effect of temperature on free lactase (*A. oryzae*) (SEQ ID NO: 1) and covalently immobilized lactase on low carboxylic acid polystyrene-co-acrylic acid microspheres (1.2 um; 87 Å2 between carboxylic groups) and high carboxylic acid polystyrene-co-acrylic acid microspheres (1.1 um; 6.2 Å2 between carboxylic groups) at pH 5.0 (0.1M acetate buffer) using ONPG as enzyme substrate. Values represent mean values±standard deviation (N=3).

FIG. 12 is a schematic showing glucosamine blocking of lactase carboxylic groups in the presence of EDC, where R—COO$^-$ represents aspartic acid and glutamic acid residues of lactase.

FIG. 13 is an amino acid sequence for lactase (*A. oryzae*) (SEQ ID NO: 1) adapted from Berka, 1998. Acidic amino acids (aspartate and glutamate) are highlighted.

FIG. 14 is a gel electrophoresis showing isoelectric focusing gel of native and carboxylic acid-blocked lactase.

Figure 15:
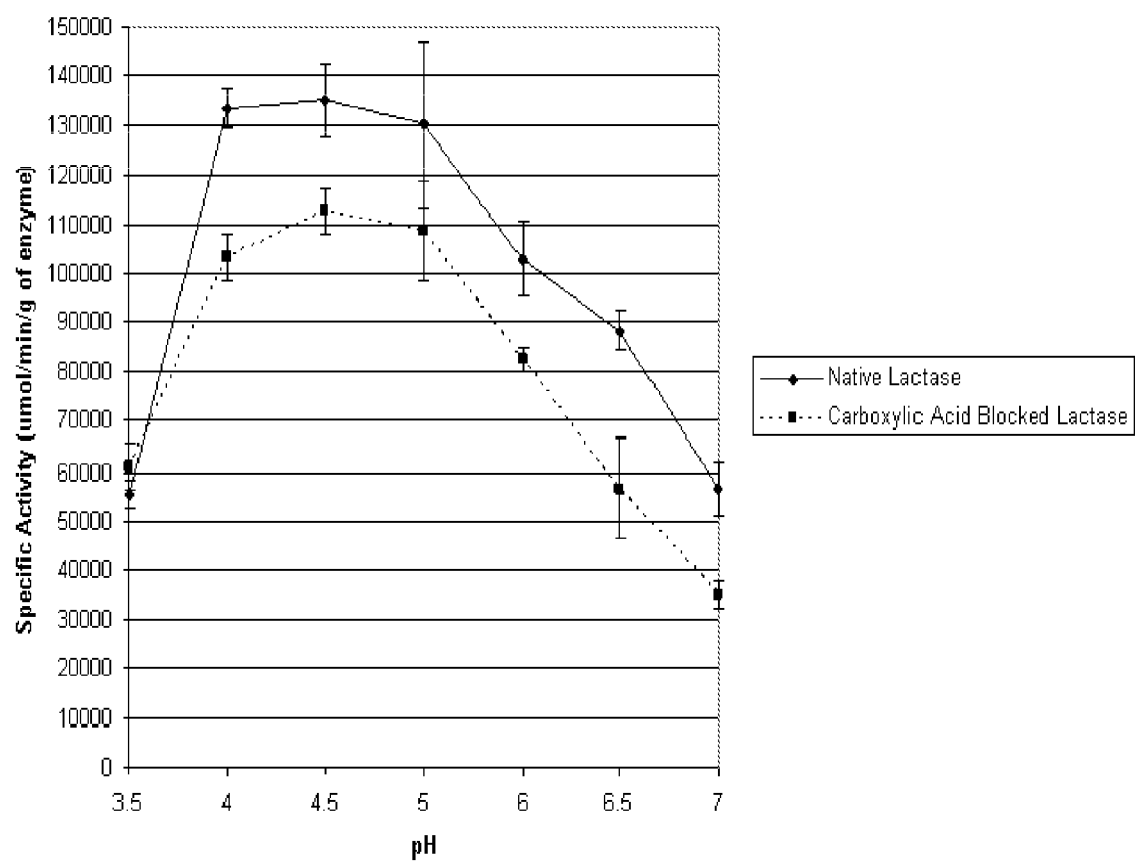

FIG. 15 is a chart showing the effect of pH on free native and carboxylic acid-blocked lactase (*A. oryzae*) (SEQ ID NO: 1) at 50° C. using ONPG as enzyme substrate. Values represent mean values±standard deviation (N=3).

Figure 16:
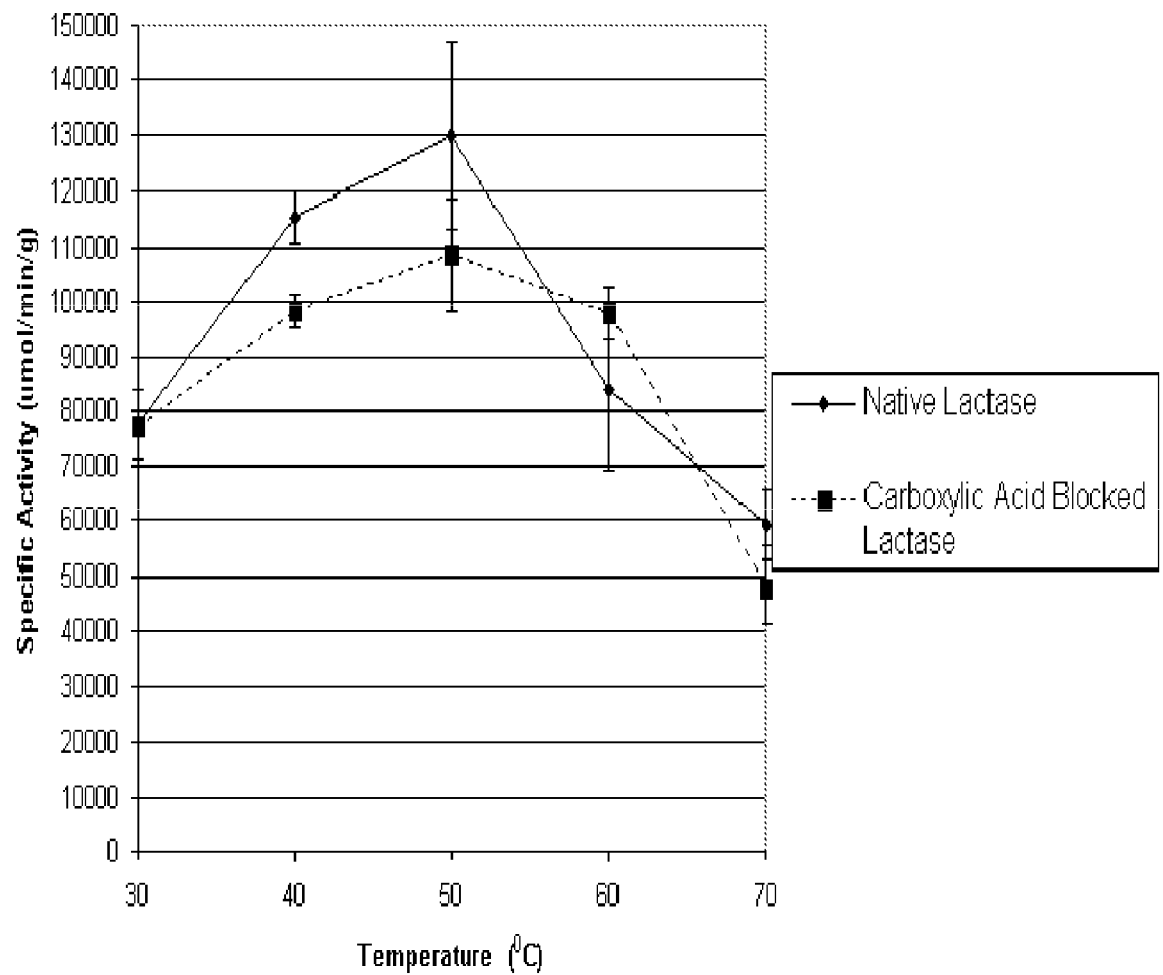

FIG. 16 is a chart showing the effect of temperature on free native lactase (*A. oryzae*) (SEQ ID NO: 1) and carboxylic acid blocked lactase at pH 5.0 (0.1M acetate buffer) using ONPG as enzyme substrate. Values represent mean values±standard deviation (N=3).

Figure 17:
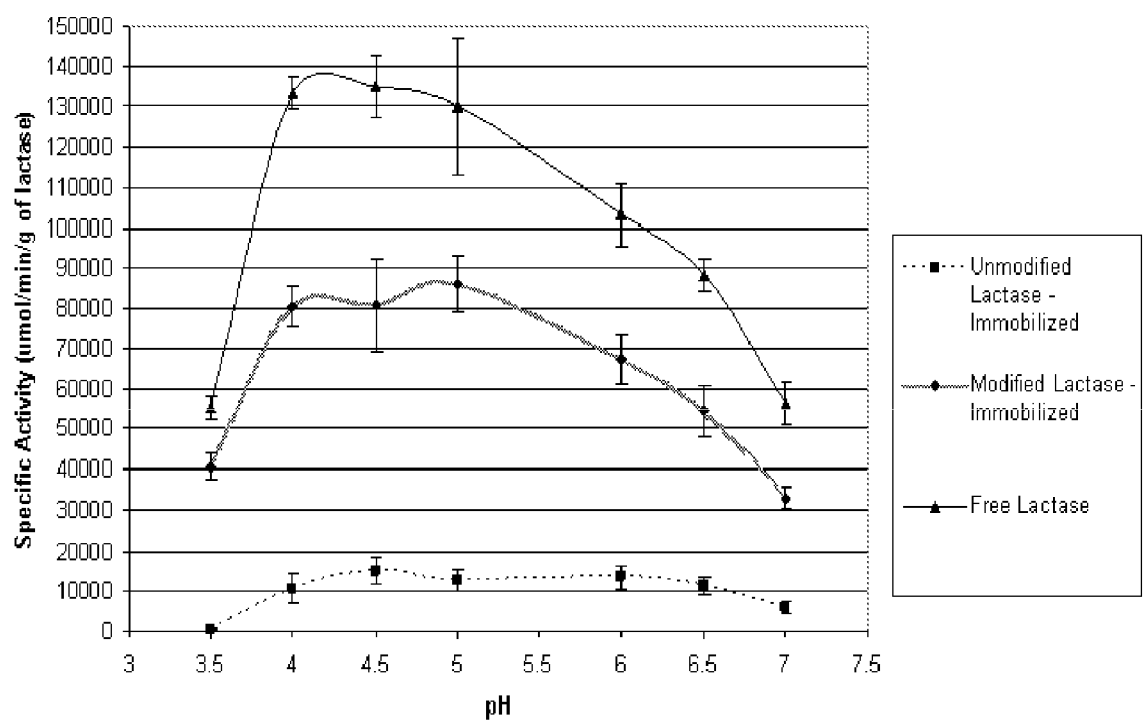

FIG. 17 is a chart showing the effect of pH on native lactase (*A. oryzae*) (SEQ ID NO: 1) and carboxylic acid-blocked lactase (modified with glucosamine), covalently immobilized on high carboxylic acid polystyrene-co-acrylic acid microspheres (1.1 um; 6.2 Å2 between carboxylic groups) at 50° C. using ONPG as enzyme substrate. Values represent mean values±standard deviation (N=3).

Figure 18:
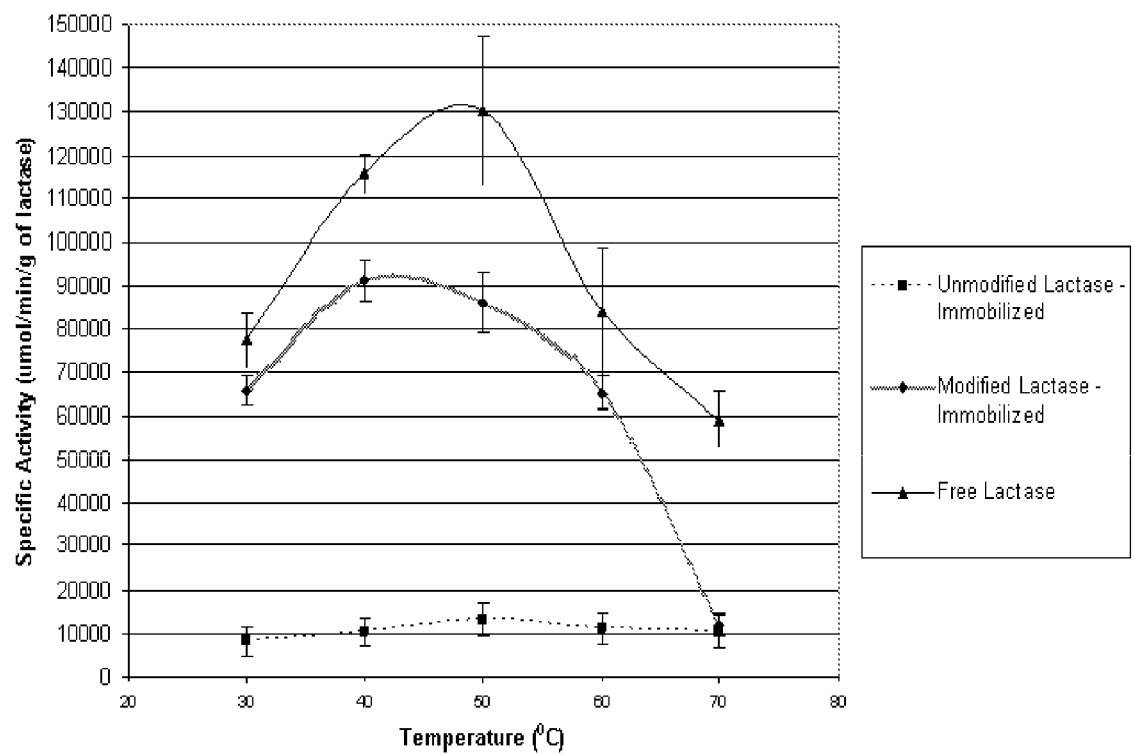

FIG. 18 is a chart showing the effect of temperature on native lactase (*A. oryzae*) (SEQ ID NO: 1) and carboxylic acid blocked lactase (modified with glucosamine), covalently immobilized on high carboxylic acid polystyrene-co-acrylic acid microspheres (1.1 um; 6.2 Å2 between carboxylic groups) at pH 5.0 (0.1M acetate buffer) using ONPG as enzyme substrate. Values represent mean values±standard deviation (N=3).

Figure 19:
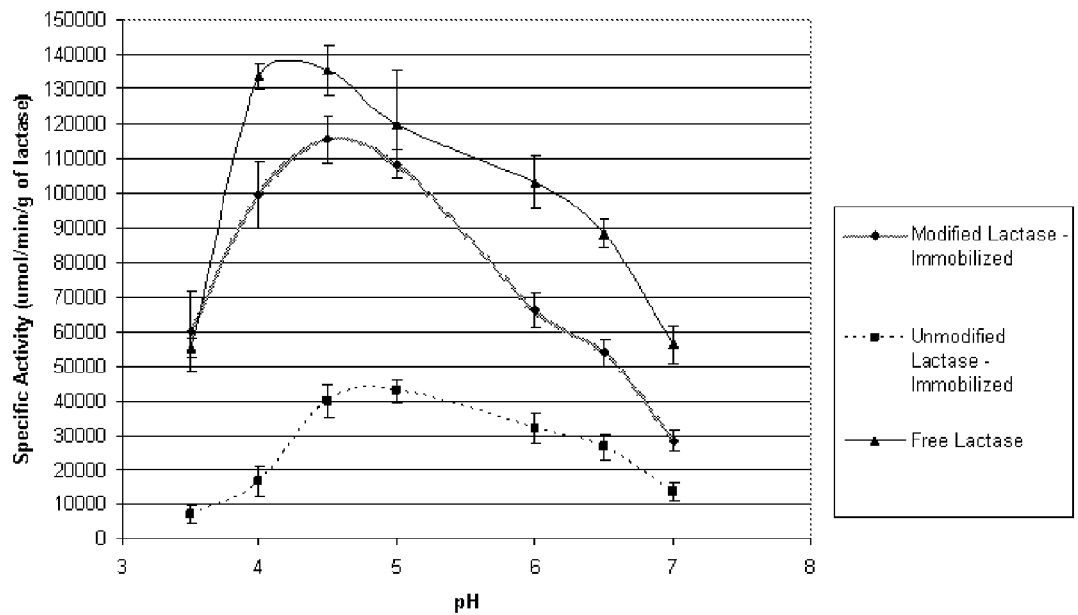

FIG. 19 is a chart showing the effect of pH on native lactase (*A. oryzae*) (SEQ ID NO: 1) and carboxylic acid-blocked lactase (modified with glucosamine), covalently immobilized lactase on low carboxylic acid polystyrene-co-acrylic acid microspheres at 50° C. using ONPG as enzyme substrate. Values represent mean values±standard deviation (N=3).

Figure 20:
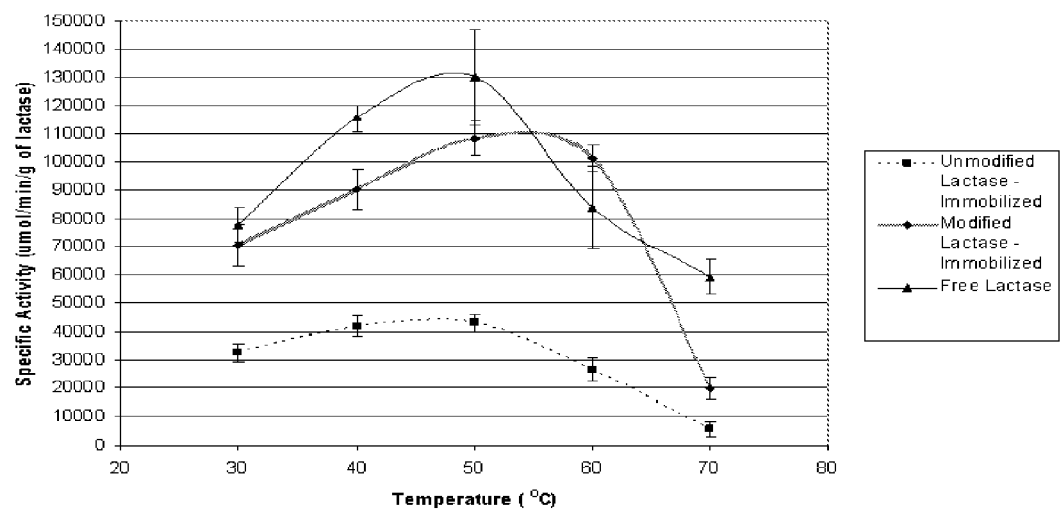

FIG. 20 is a chart showing the effect of temperature on native lactase (*A. oryzae*) (SEQ ID NO: 1) and carboxylic acid blocked lactase (modified with glucosamine), covalently immobilized on low carboxylic acid polystyrene-co-acrylic acid microspheres (1.2 um; 87 Å2 between carboxylic groups) at pH 5.0 (0.1M acetate buffer) using ONPG as enzyme substrate. Values represent mean values±standard deviation (N=3).

Figure 21:
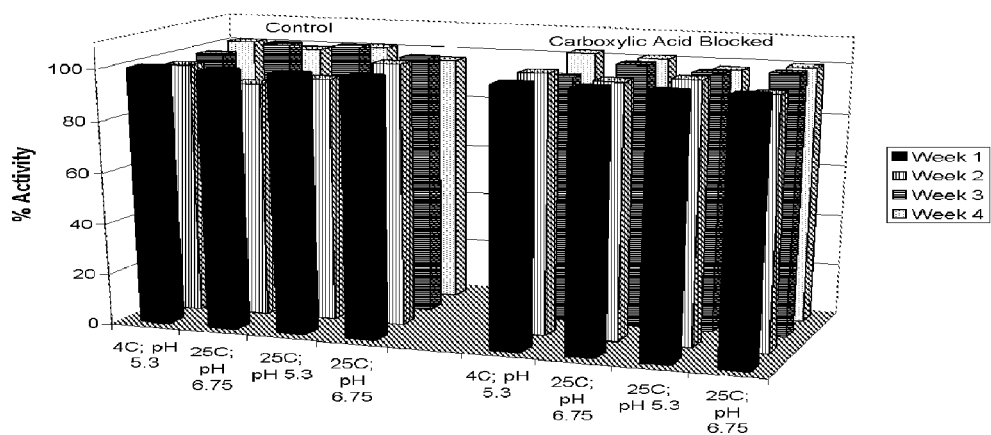

FIG. 21 is a graph showing the stability of immobilized lactase (A. oryzae) (SEQ ID NO: 1) on low carboxylic acid polystyrene-co-acrylic acid microspheres. Activity at 50° C., pH 5.0 using ONPG as enzyme substrate. Values represent mean values±standard deviation (N=3).

Figure 22:
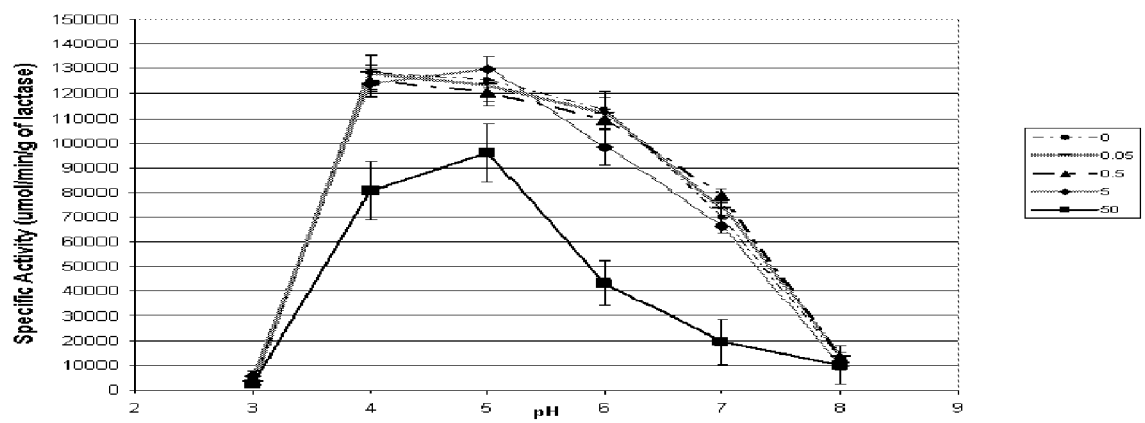

FIG. 22 is a graph showing the effect of pH on carbodiimide-modified lactase (A. oryzae) (SEQ ID NO: 1) activity. Activity at 50° C. (0.1M acetate buffer) using ONPG as enzyme substrate. Legend indicates molar excess of carbodiimide relative to available carboxylic acid of lactase. Values represent mean values±standard deviation (N=3).

Figure 23:
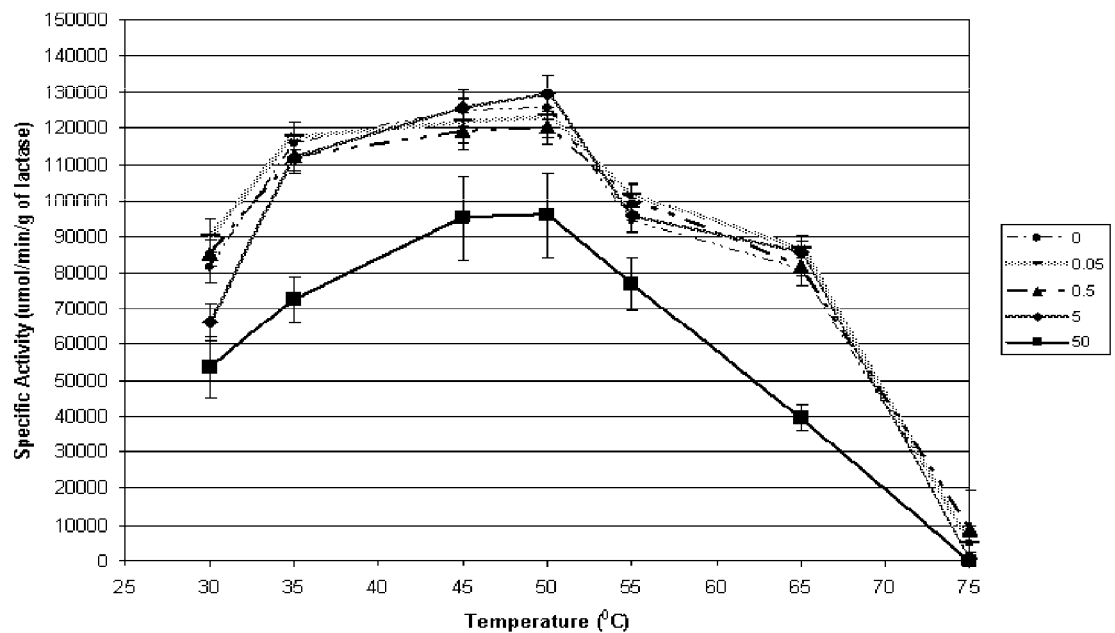

FIG. 23 is a graph showing the effect of temperature on carbodiimide-modified lactase (A. oryzae) (SEQ ID NO: 1) activity at pH 5.0 (0.1M acetate buffer) using ONPG as enzyme substrate. Legend indicates molar excess of carbodiimide relative to available carboxylic acid of lactase. Values represent mean values±standard deviation (N=3).

Figure 24:
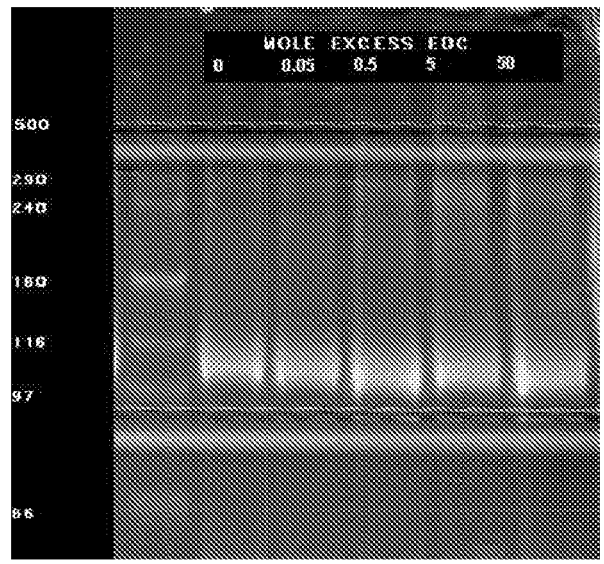

FIG. 24 is a SDS-PAGE gel of lactase modified with molar excess of carbodiimide (EDC).

Figure 25:
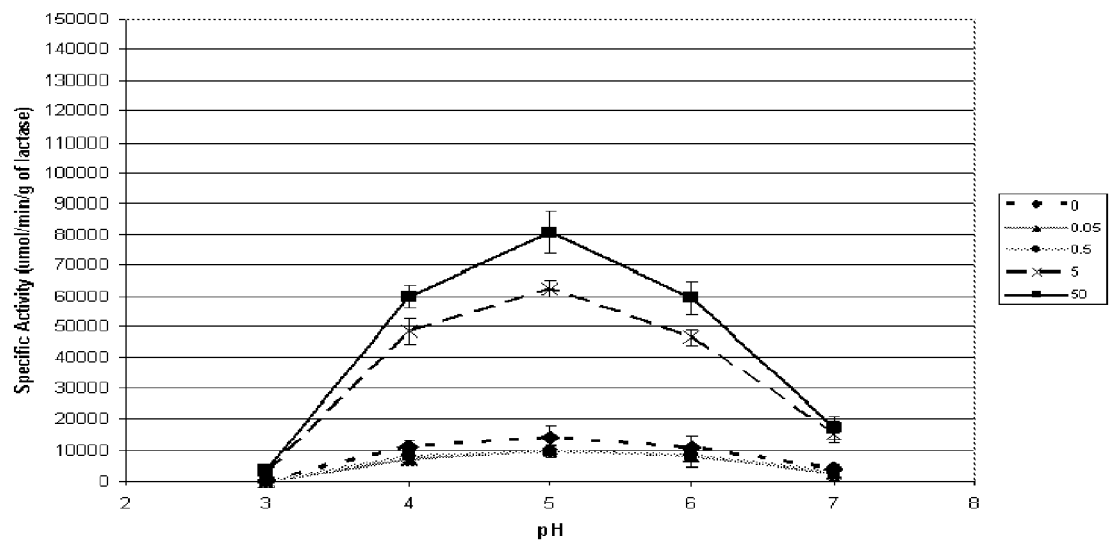

FIG. 25 is graph showing the effect of pH on carbodiimide (EDC) modified lactase (A. oryzae) (SEQ ID NO: 1), covalently immobilized on high carboxylic acid polystyrene-co-acrylic acid microspheres (1.1 um; 6.2 Å2 between carboxylic groups) at 50° C. using ONPG as enzyme substrate. Legend represents molar excess of EDC to enzyme carboxylic acid groups. Values represent mean values±standard deviation (N=3).

Figure 26:
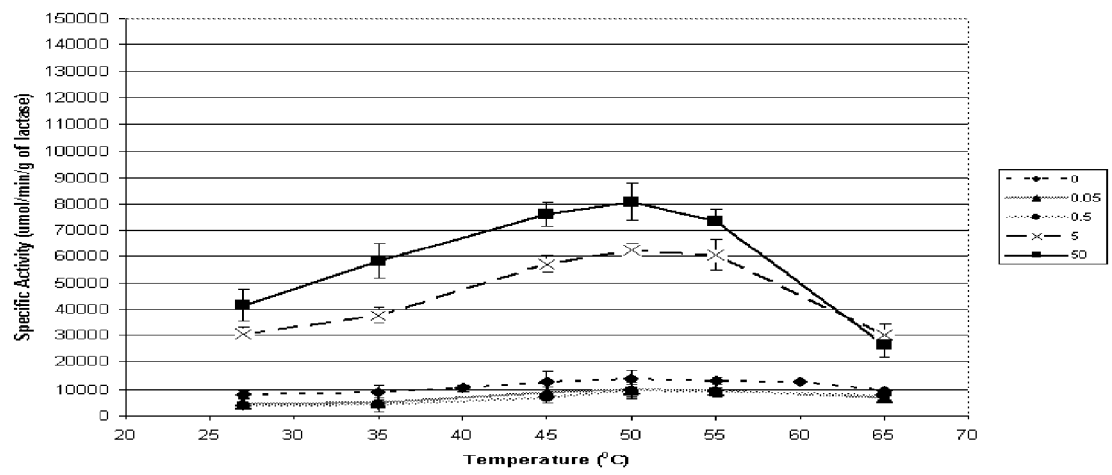

FIG. 26 is a graph showing the effect of temperature on carbodiimide (EDC) modified lactase (A. oryzae) (SEQ ID NO: 1), covalently immobilized on high carboxylic acid polystyrene-co-acrylic acid microspheres (1.1 um; 6.2 Å2 between carboxylic groups) at pH 5.0 (0.1M acetate buffer) using ONPG as enzyme substrate. Legend represents molar excess of EDC to enzyme carboxylic acid groups. Values represent mean values±standard deviation (N=3).

Figure 27:
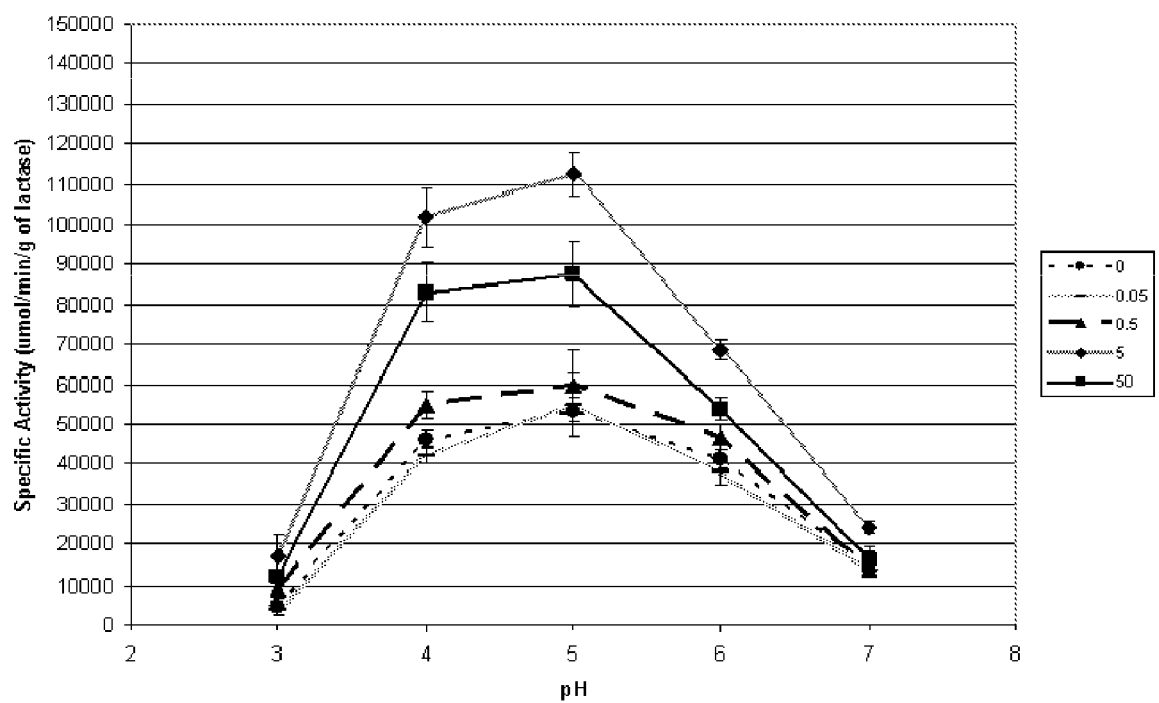

FIG. 27 is a graph showing the effect of pH on carbodiimide (EDC) modified lactase (A. oryzae) (SEQ ID NO: 1), covalently immobilized on low carboxylic acid polystyrene-co-acrylic acid microspheres (1.2 um; 87 Å2 between carboxylic groups) at 50° C. using ONPG as enzyme substrate. Legend represents molar excess of EDC to enzyme carboxylic acid groups. Values represent mean values±standard deviation (N=3).

Figure 28:
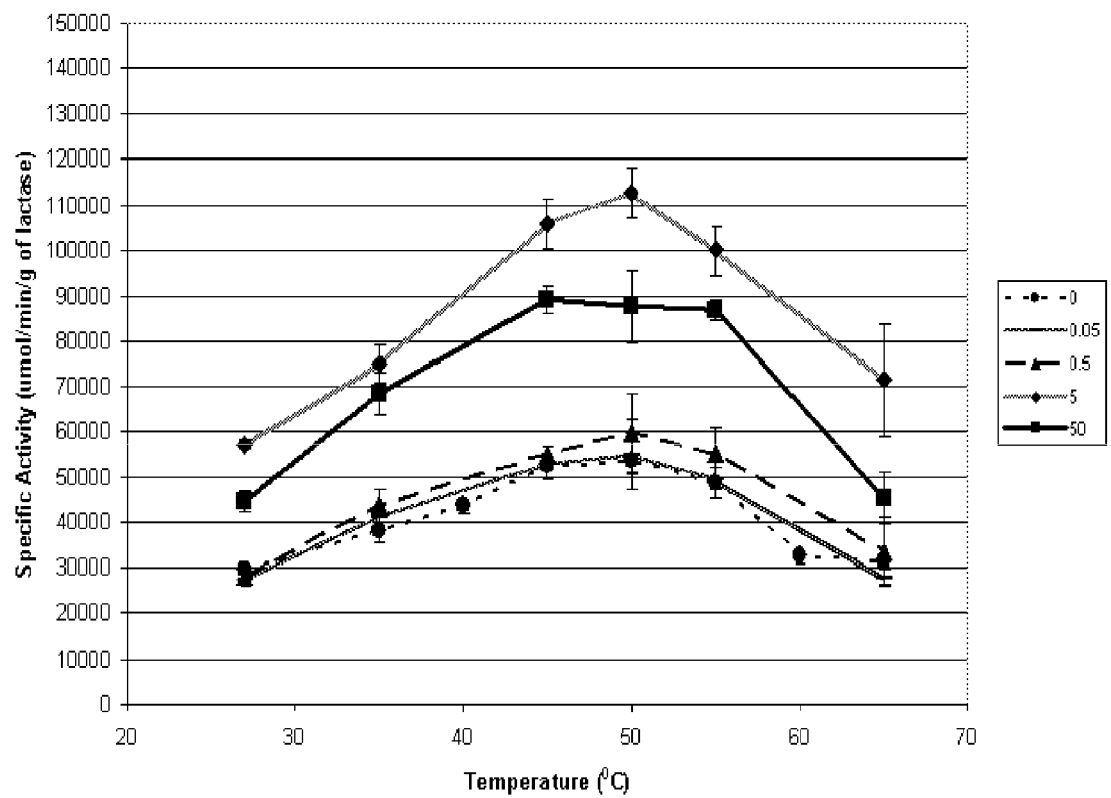

FIG. 28 is a graph showing the effect of temperature on carbodiimide (EDC) modified lactase (A. oryzae) (SEQ ID NO: 1), covalently immobilized on low carboxylic acid polystyrene-co-acrylic acid microspheres (1.2 um; 87 Å2 between carboxylic groups) at pH 5.0 (0.1M acetate buffer) using ONPG as enzyme substrate. Legend represents molar excess of EDC to enzyme carboxylic acid groups. Values represent mean values±standard deviation (N=3).

Figure 29:
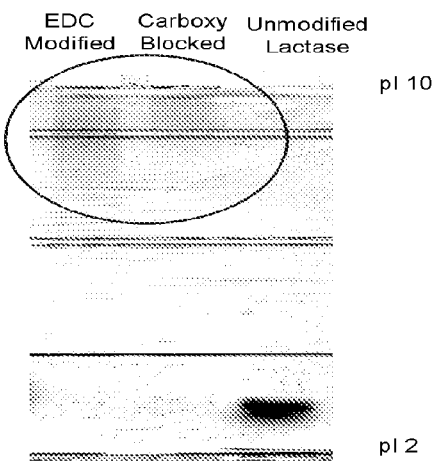

FIG. 29 is a gel electrophoresis showing isoelectric focusing gel of native, carboxylic acid-blocked, and carbodiimide modified (50×) lactase.

Figure 30:
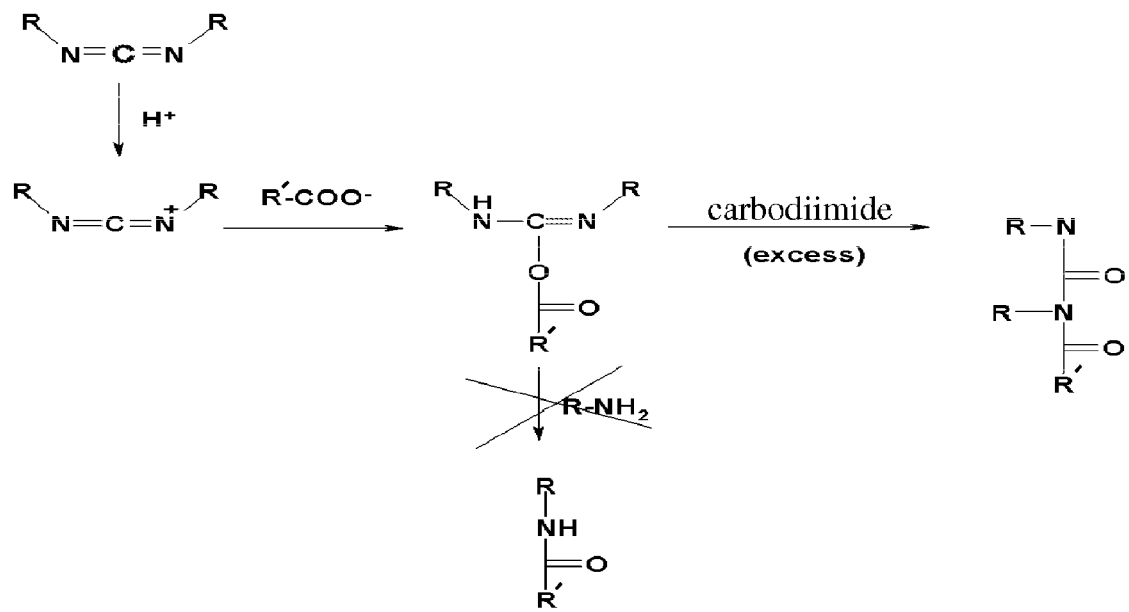

FIG. 30 is a schematic showing N-acylurea formation in the presence of excess carbodiimide and absence of a reactive nucleophile (R—$NH_2$), where R—$COO^-$ represents aspartic acid and glutamic acid residues of lactase.

Figure 31:
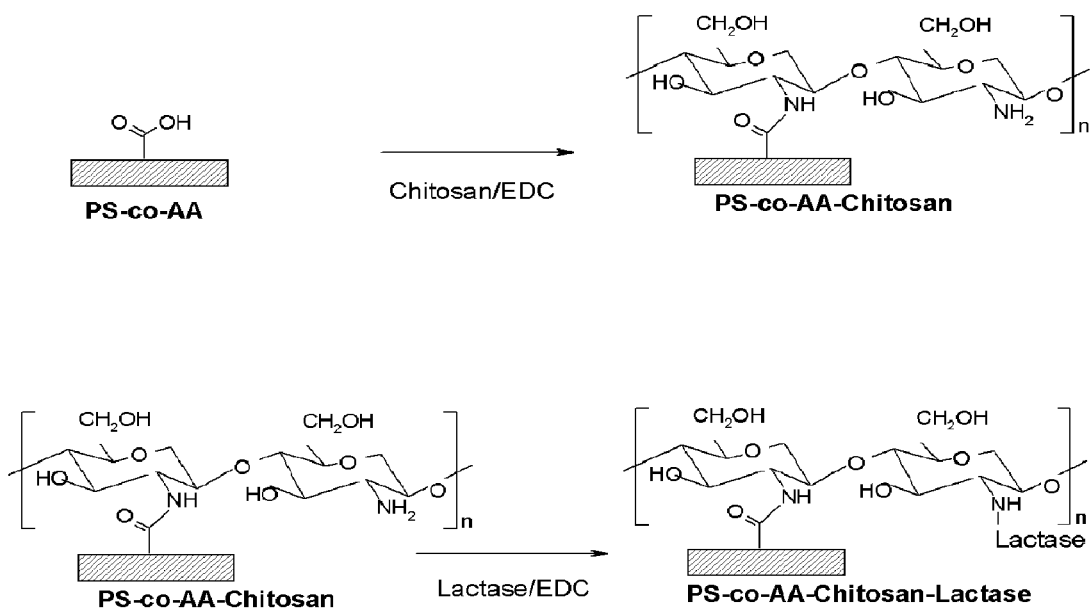

FIG. 31 is a schematic showing lactase immobilization by a chitosan tethered intermediate.

Figure 32:
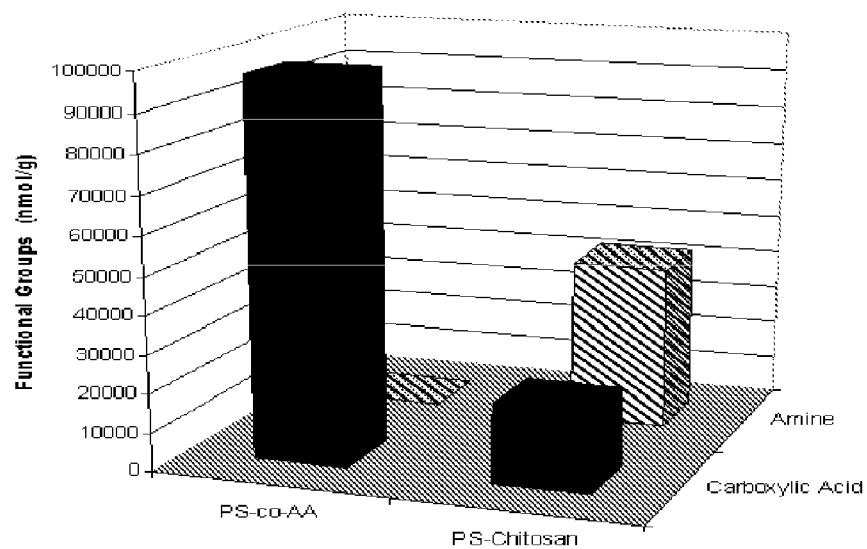

FIG. 32 is a chart showing the functionality of microspheres determined by dye binding assays (N=3).

Figure 33:
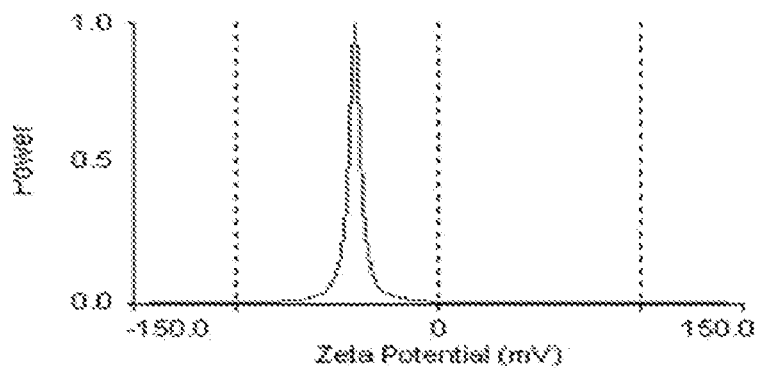

FIG. 33 is a graph showing the zeta potential of carboxylated microspheres (pH 5.3).

Figure 34:
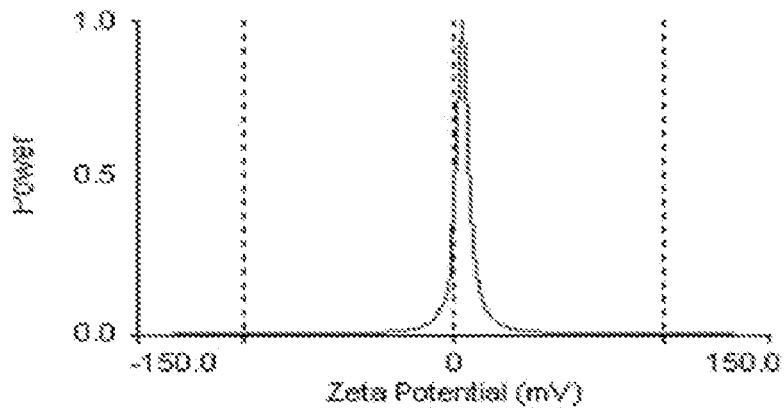

FIG. 34 is a graph showing the zeta potential of chitosan-tethered microspheres (pH 5.3).

Figure 35:
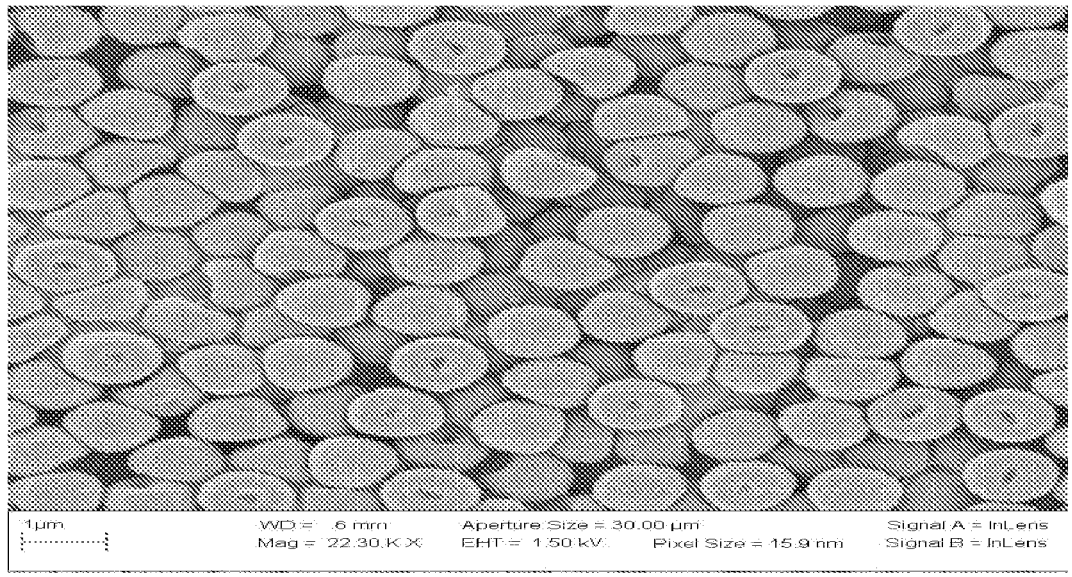

FIG. 35 is a scanning electron micrograph of high carboxylic acid polystyrene-co-acrylic acid microspheres.

Figure 36:
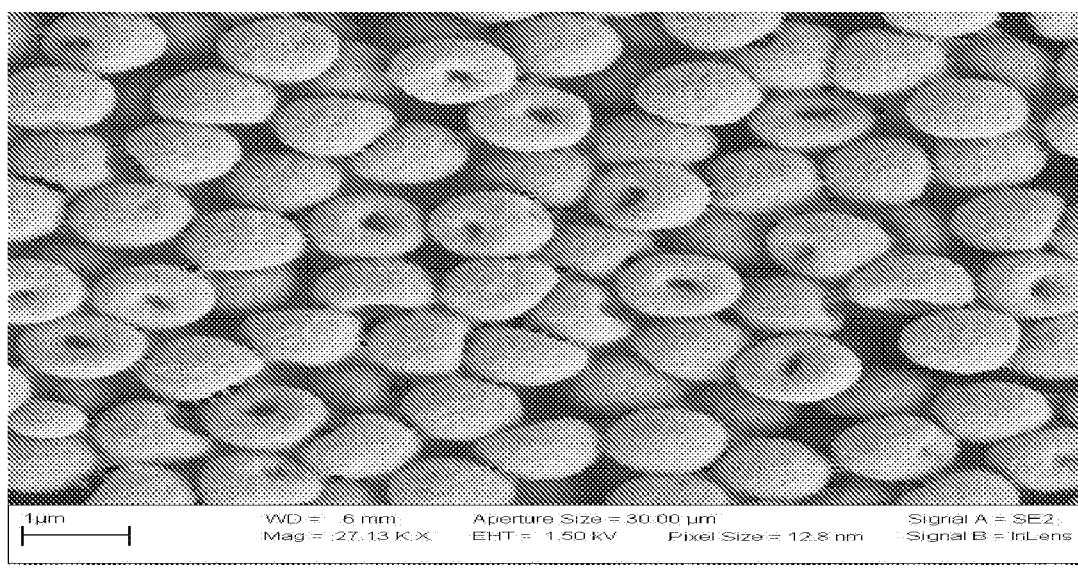

FIG. 36 is a scanning electron micrograph of chitosan-tethered, high carboxylic acid polystyrene-co-acrylic acid microspheres.

Figure 37:
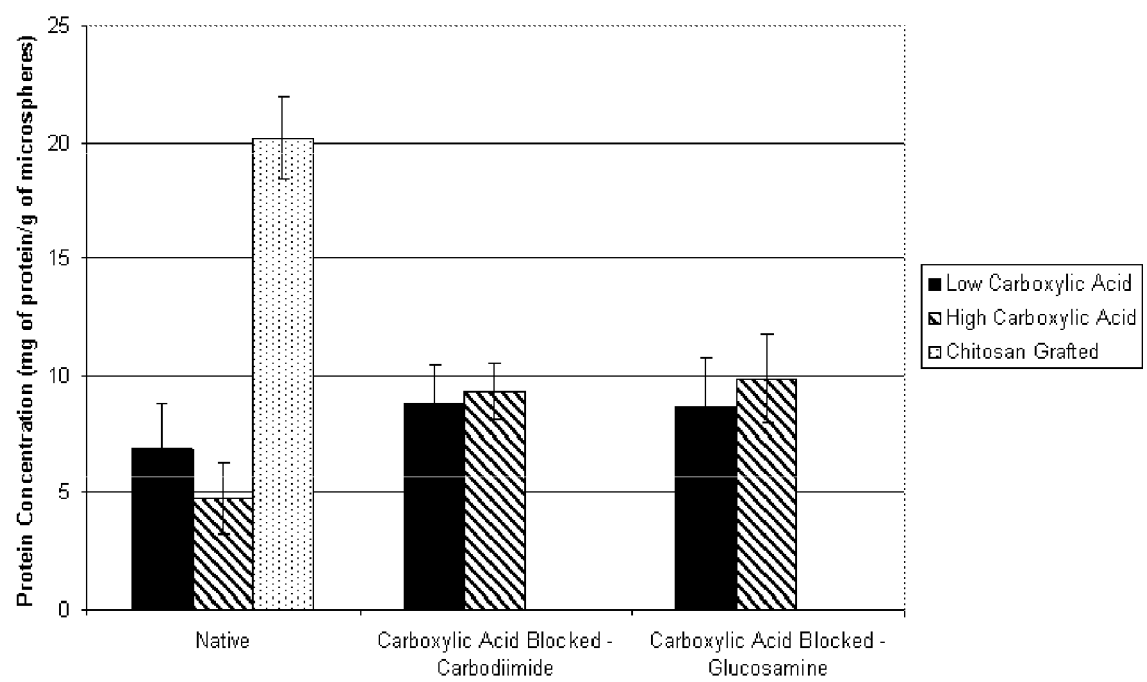

FIG. 37 is a graph showing protein loading (A. oryzae lactase) (SEQ ID NO: 1)on microspheres. Values represent mean values±standard deviation (N=3).

Figure 38:
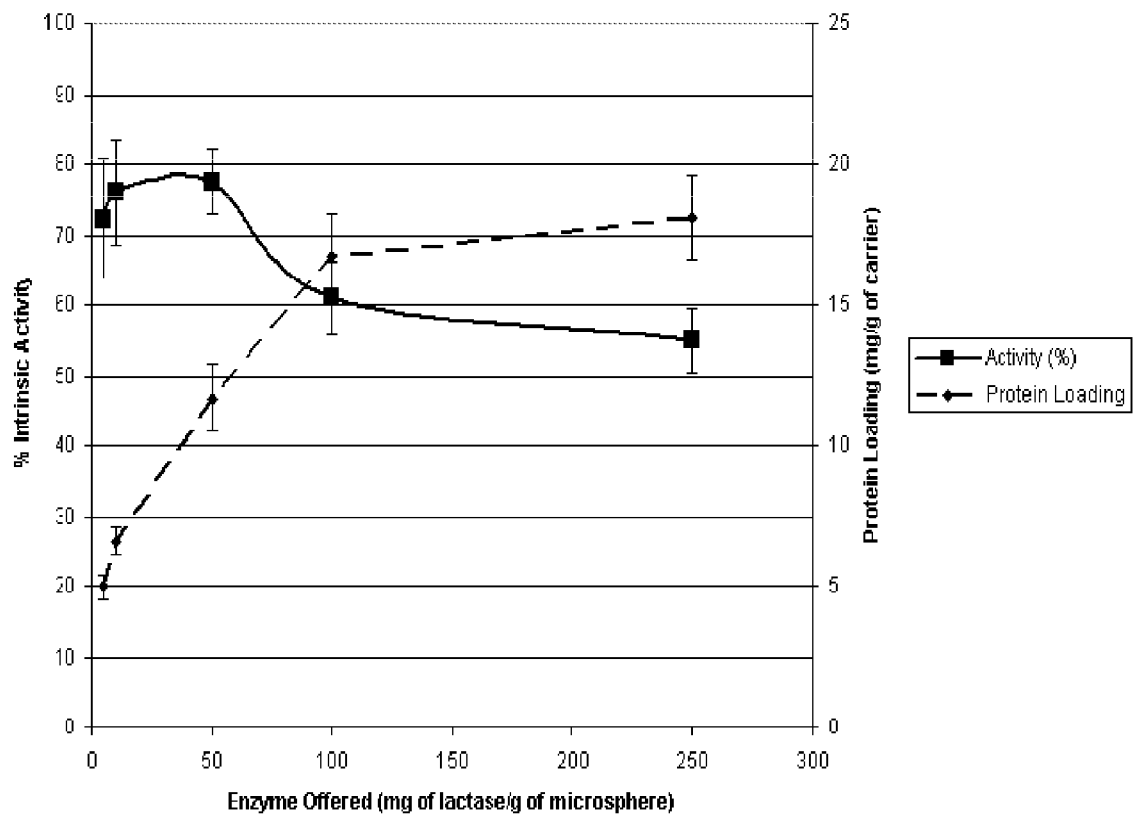

FIG. 38 is a graph of the effect of protein offered on loading and activity of (A. oryzae lactase) (SEQ ID NO: 1) on chitosan-tethered microspheres at pH 5.0 and 50° C. Values represent mean values±standard deviation (N=3).

Figure 39:

FIG. 39 is a graph of the nonlinear fit to mean loading of lactase (A. oryzae) on chitosan-tethered microspheres using a one-site total binding model, where $R^2$=0.98.

Figure 40:
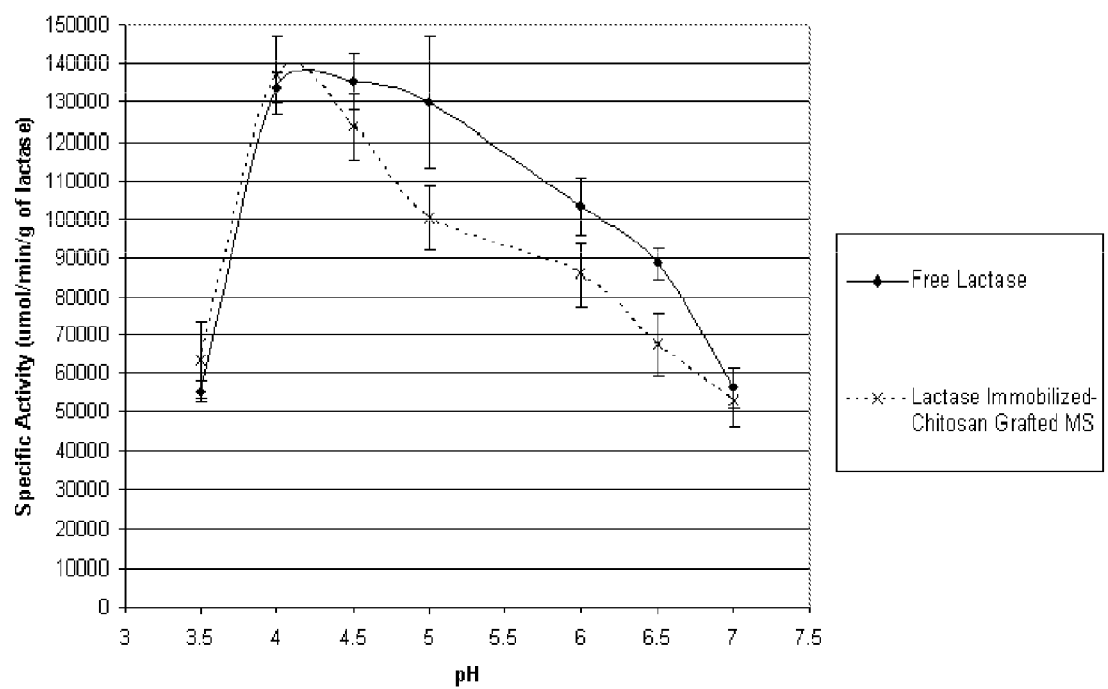

FIG. 40 is a graph of the effect of pH on native and covalently immobilized lactase (A. oryzae) (SEQ ID NO: 1) on chitosan-tethered microspheres at 50° C. using ONPG as enzyme substrate. Values represent mean values±standard deviation (N=3).

Figure 41:
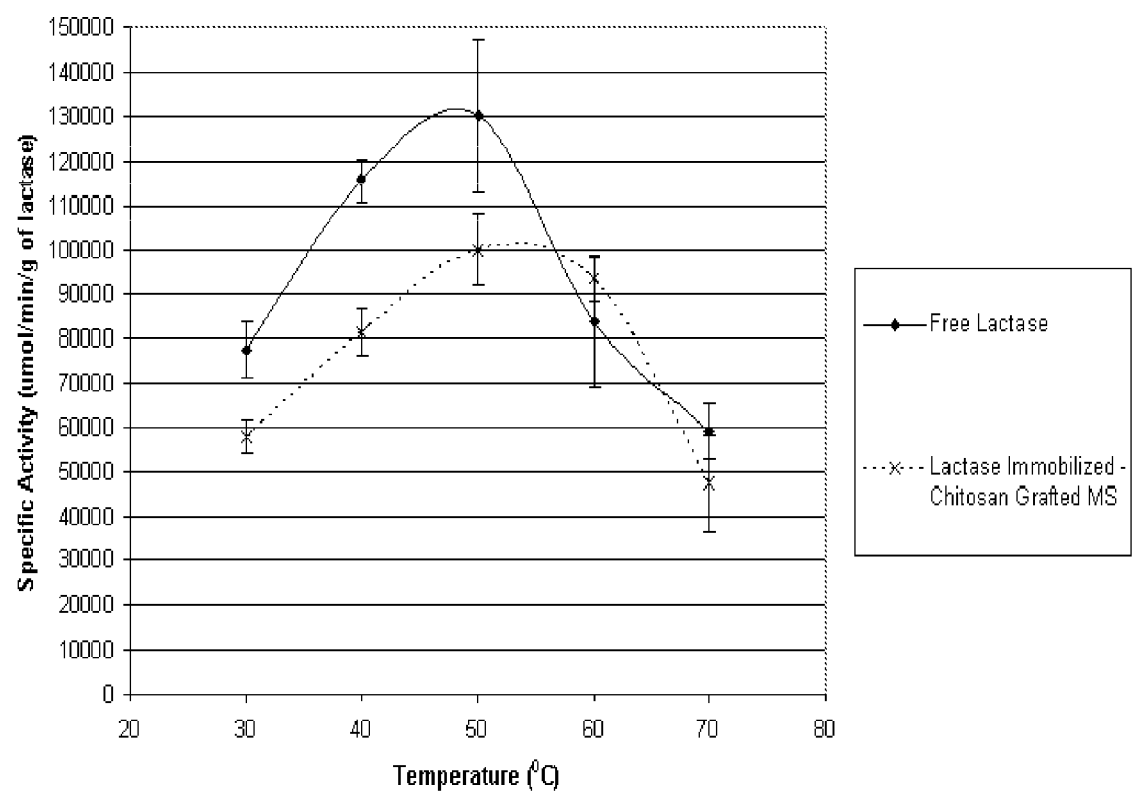

FIG. 41 is a graph of the effect of temperature on native lactase (A. oryzae) (SEQ ID NO: 1) and covalently immobilized lactase on chitosan-tethered microspheres at pH 5.0 (0.1M acetate buffer) using ONPG as enzyme substrate. Values represent mean values±standard deviation (N=3).

Figures 42, 43:
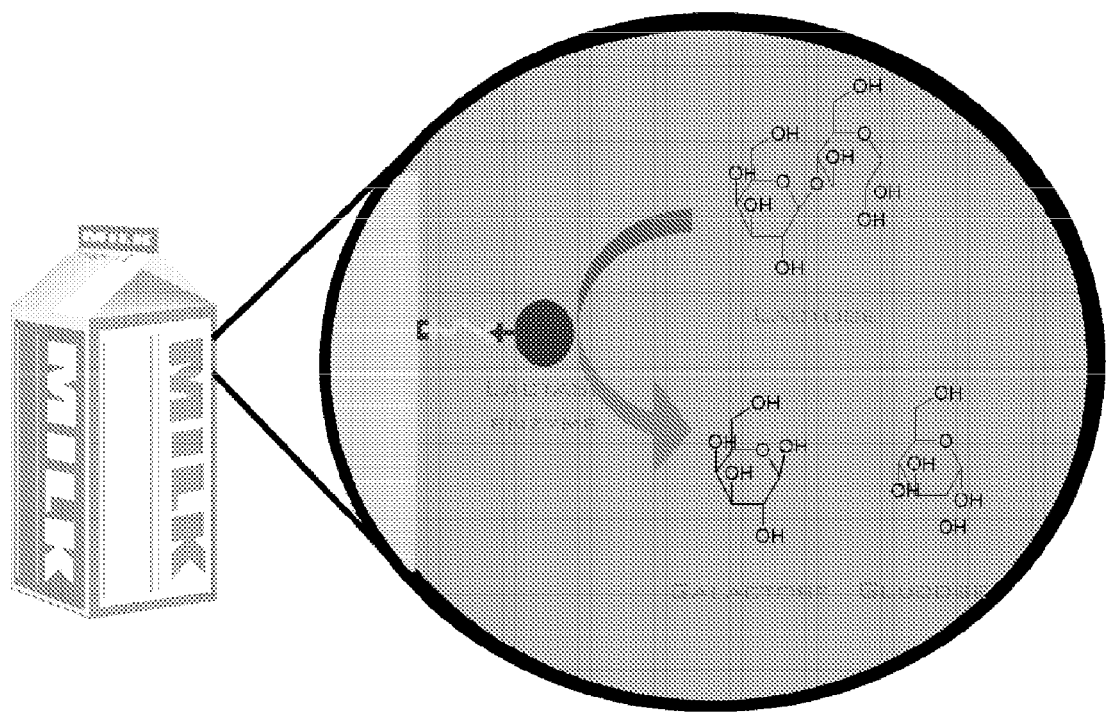

FIG. 42 is a schematic of a lactose-reducing milk carton.

FIG. 43 is a table of the XPS composition of polyethylene films.

Figure 44:
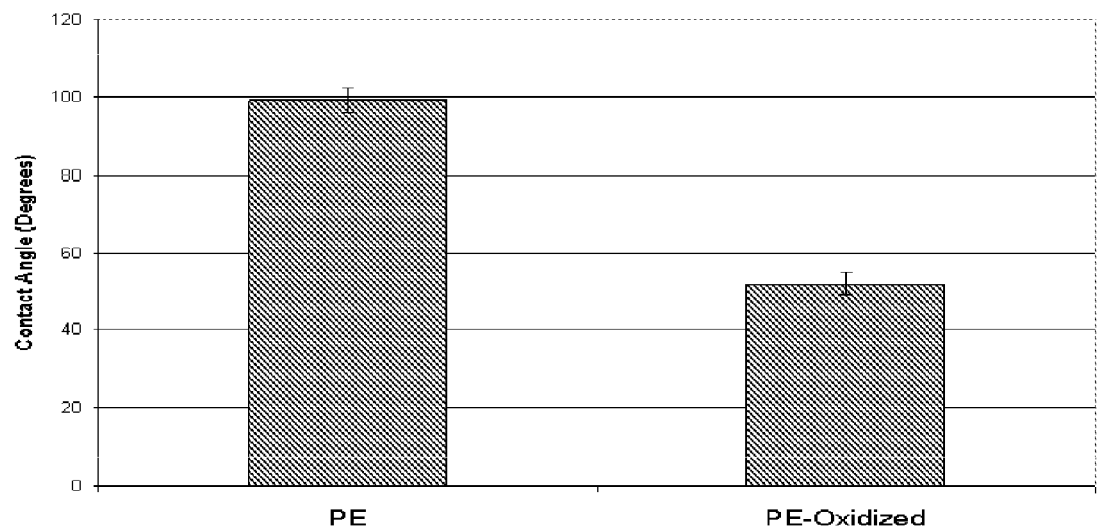

FIG. 44 is a graph of the water contact angle measurements on virgin and oxidized low density polyethylene films. Values represent mean values±standard deviation (N=3).

Figure 45:
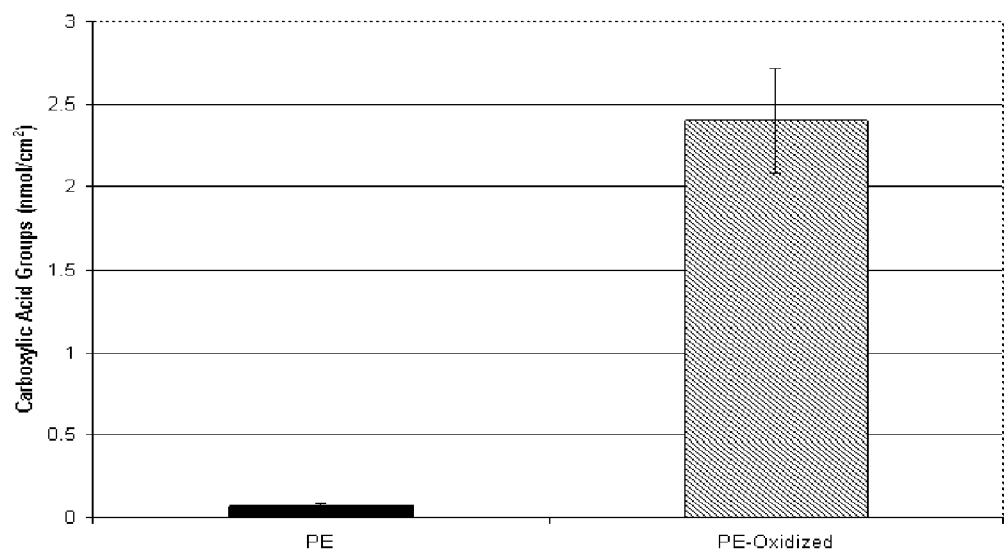

FIG. 45 is a graph of the functionality of polyethylene films. Values represent mean values±standard deviation (N=3).

Figure 46:
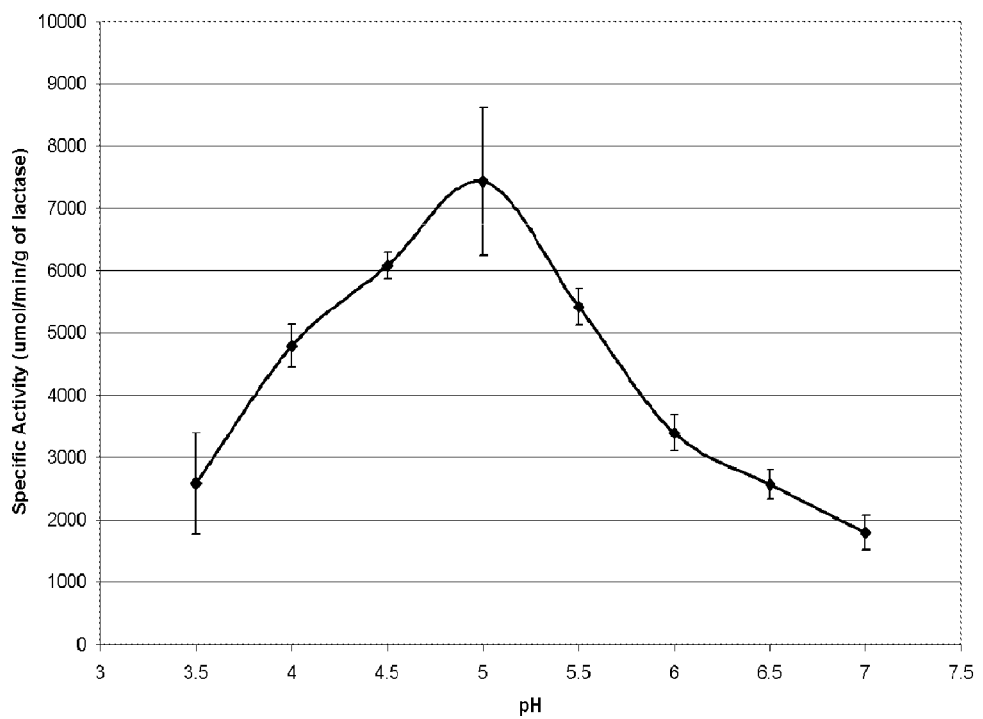

FIG. 46 is a chart of the effect of pH on covalently immobilized, carboxylic acid-blocked lactase (A. oryzae) (SEQ ID NO: 1)on polyethylene films at 50° C. using ONPG as enzyme substrate. Unblocked lactase exhibited no measurable activity when conjugated. Values represent mean values±standard deviation (N=3).

Figure 47:
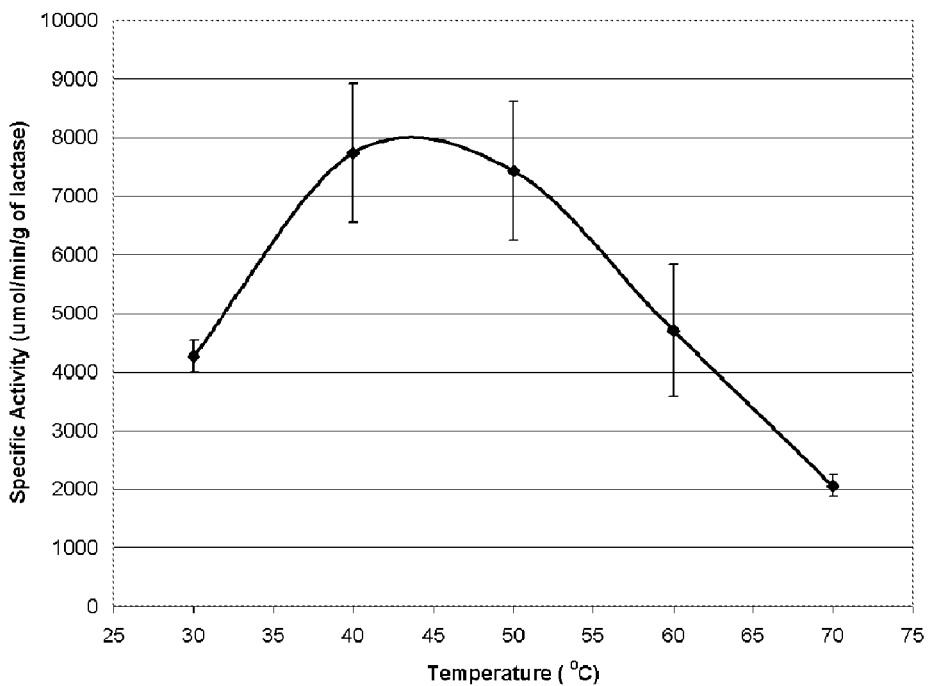

FIG. 47 is a chart of the effect of temperature on covalently immobilized, carboxylic acid-blocked lactase lactase (A. oryzae) (SEQ ID NO: 1) on polyethylene films. Activity at pH 5.0 (0.1M acetate buffer) using ONPG as enzyme substrate. Unblocked lactase exhibited no measurable activity when conjugated. Values represent mean values±standard deviation (N=3).

Figure 48:
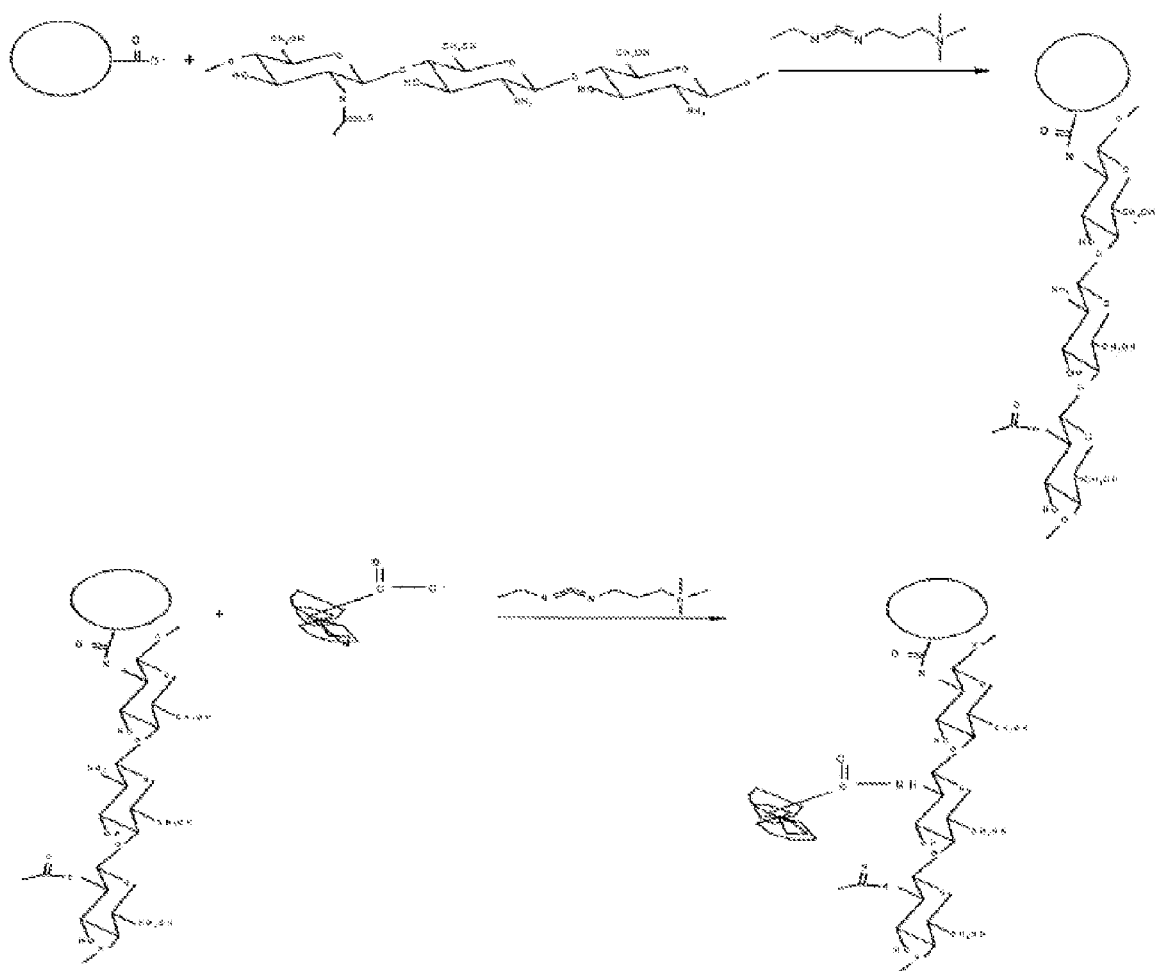

FIG. 48 is a schematic of the immobilization of lactase onto a polystyrene/acrylic acid support using a chitosan intermediate.

Figure 49:
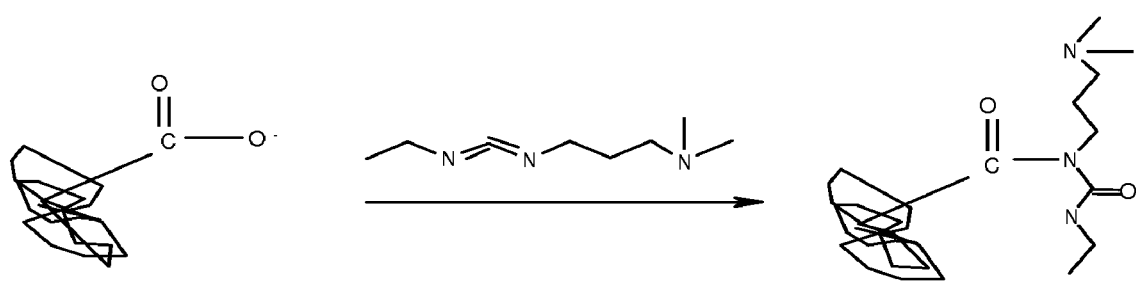

FIG. 49 is a schematic of blocking enzyme carboxyl groups.

Figure 50:
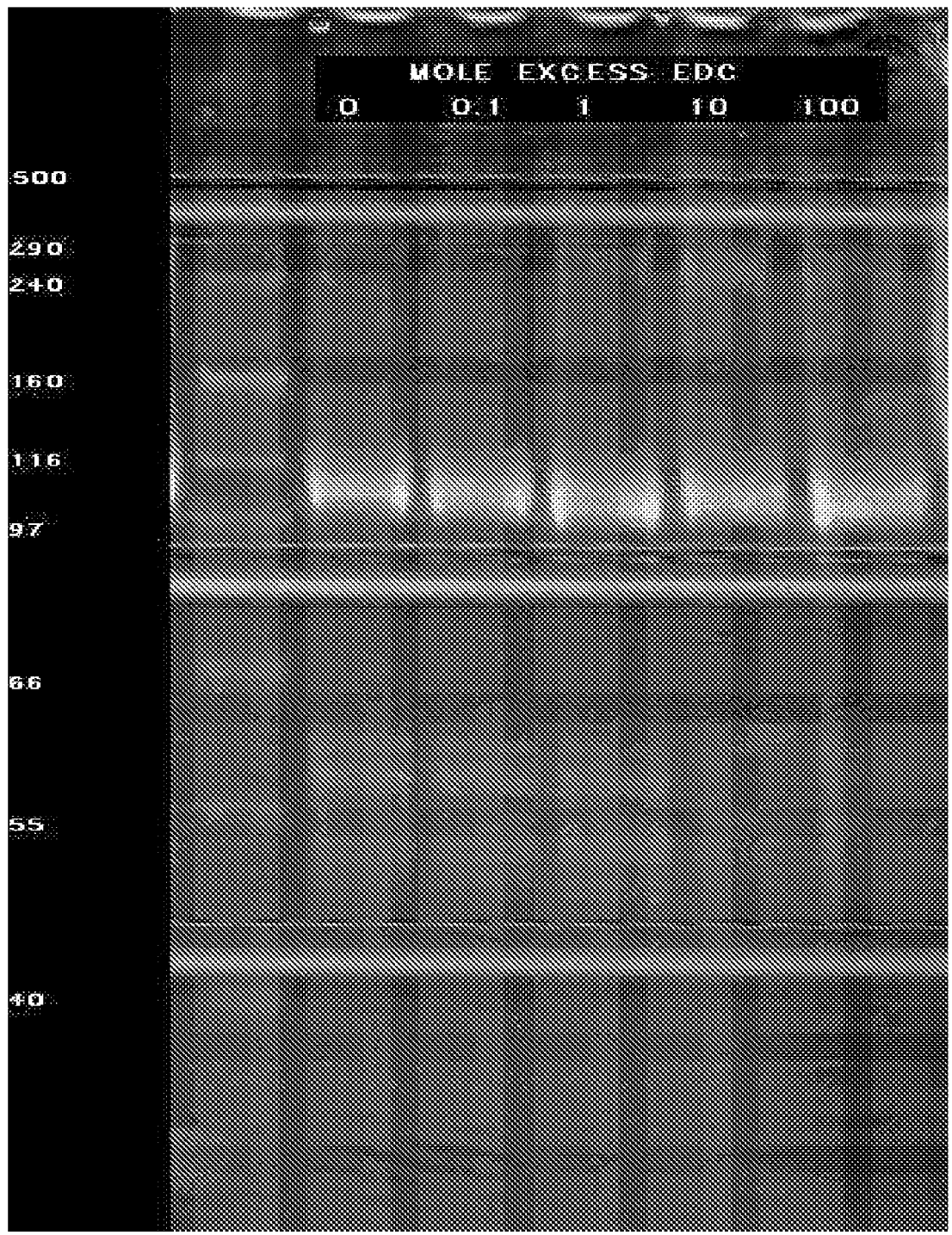

FIG. 50 is a gel electrophoresis of the product showing containment to the intramolecular level of the enzyme as evidenced by the bright gel electrophoresis bands, which corresponds to a single molecular weight subunit.

Figure 51:
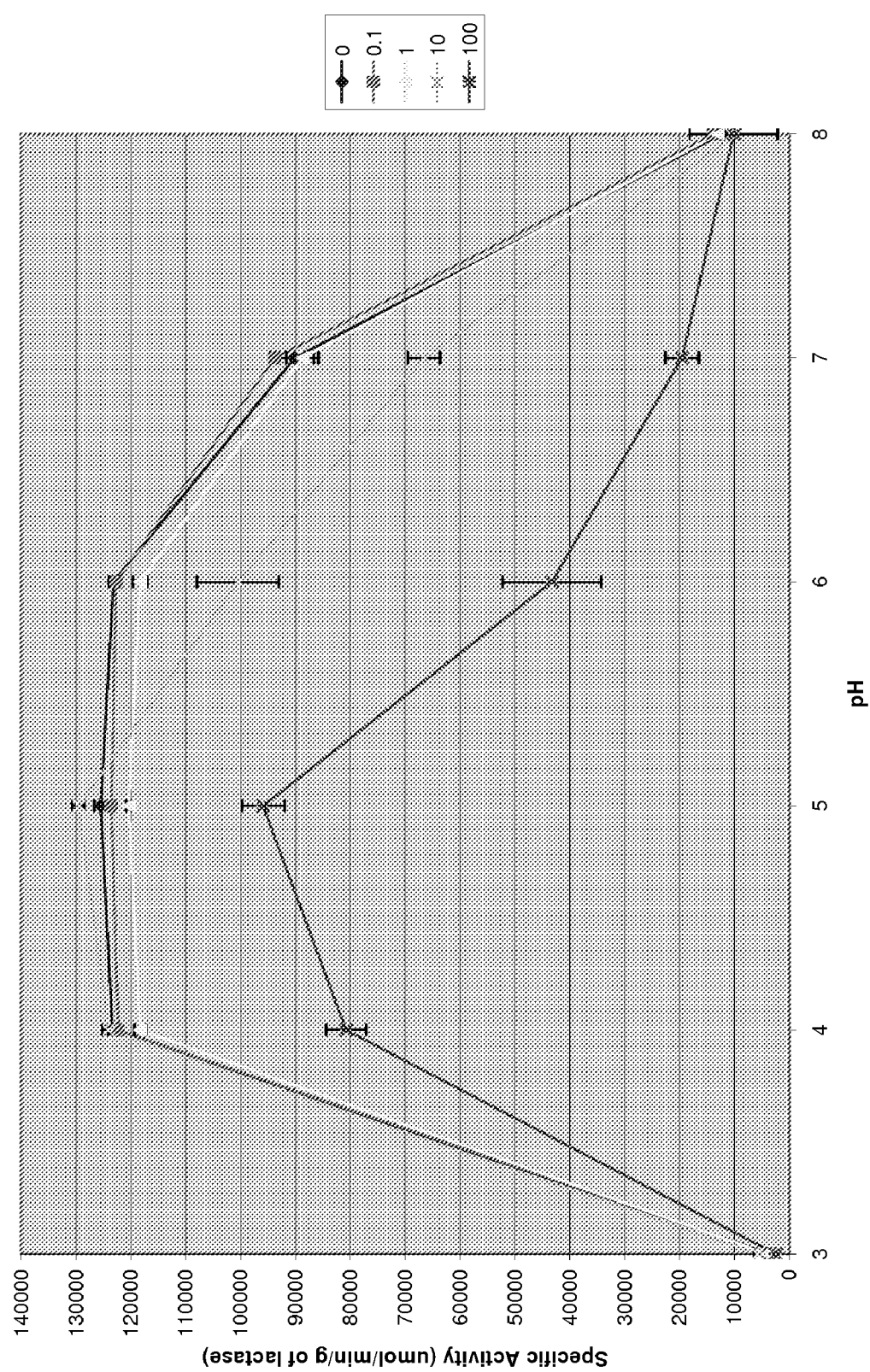

FIG. 51 is a graph of the temperature profile trends of a 100×-carbodiimide enzyme according to the present invention showing a significant change in activity between pH 5 and 6.

Figure 52:
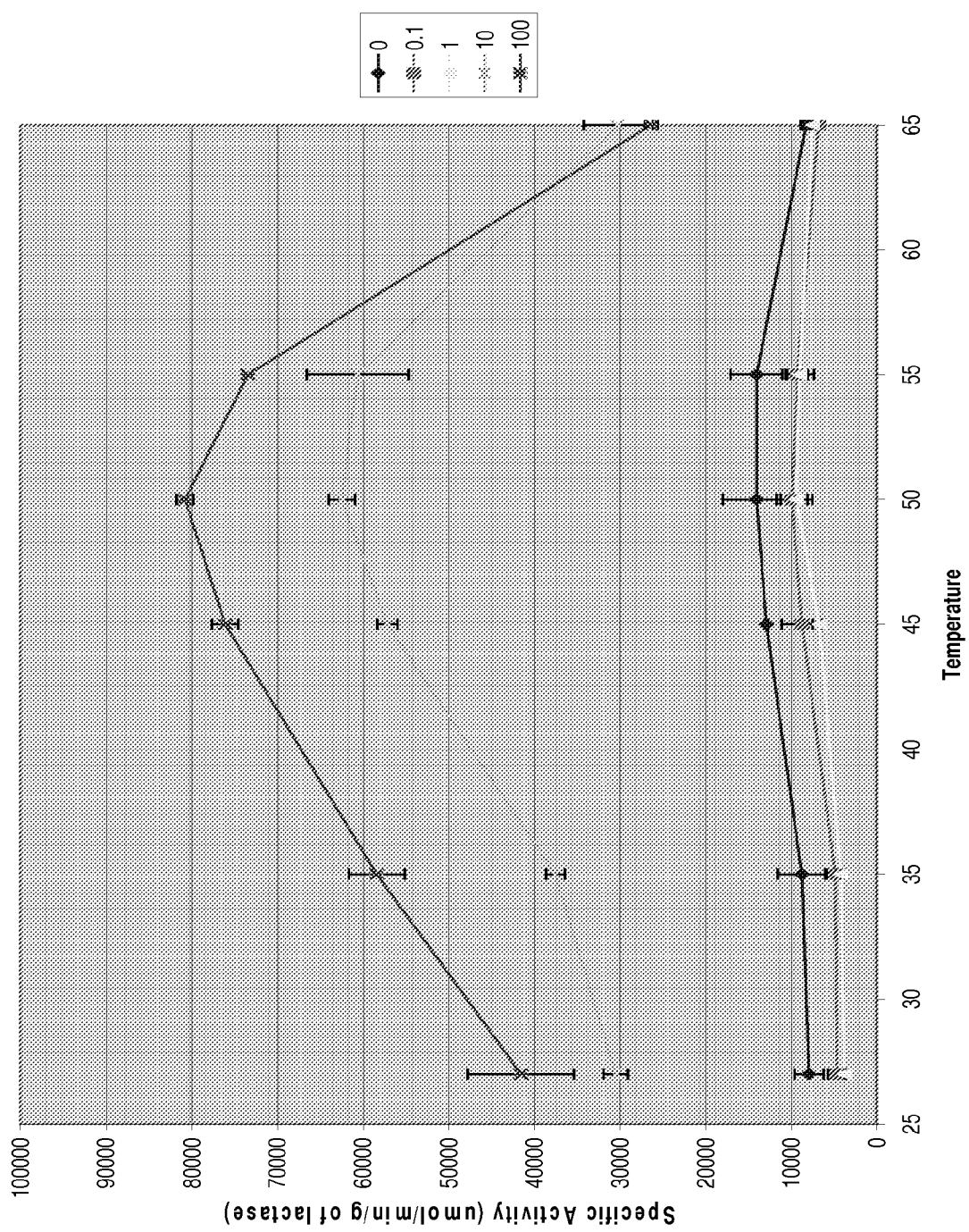

FIG. 52 is a graph of the specific activity of the 100× immobilized enzyme verses temperature.

Figure 53:
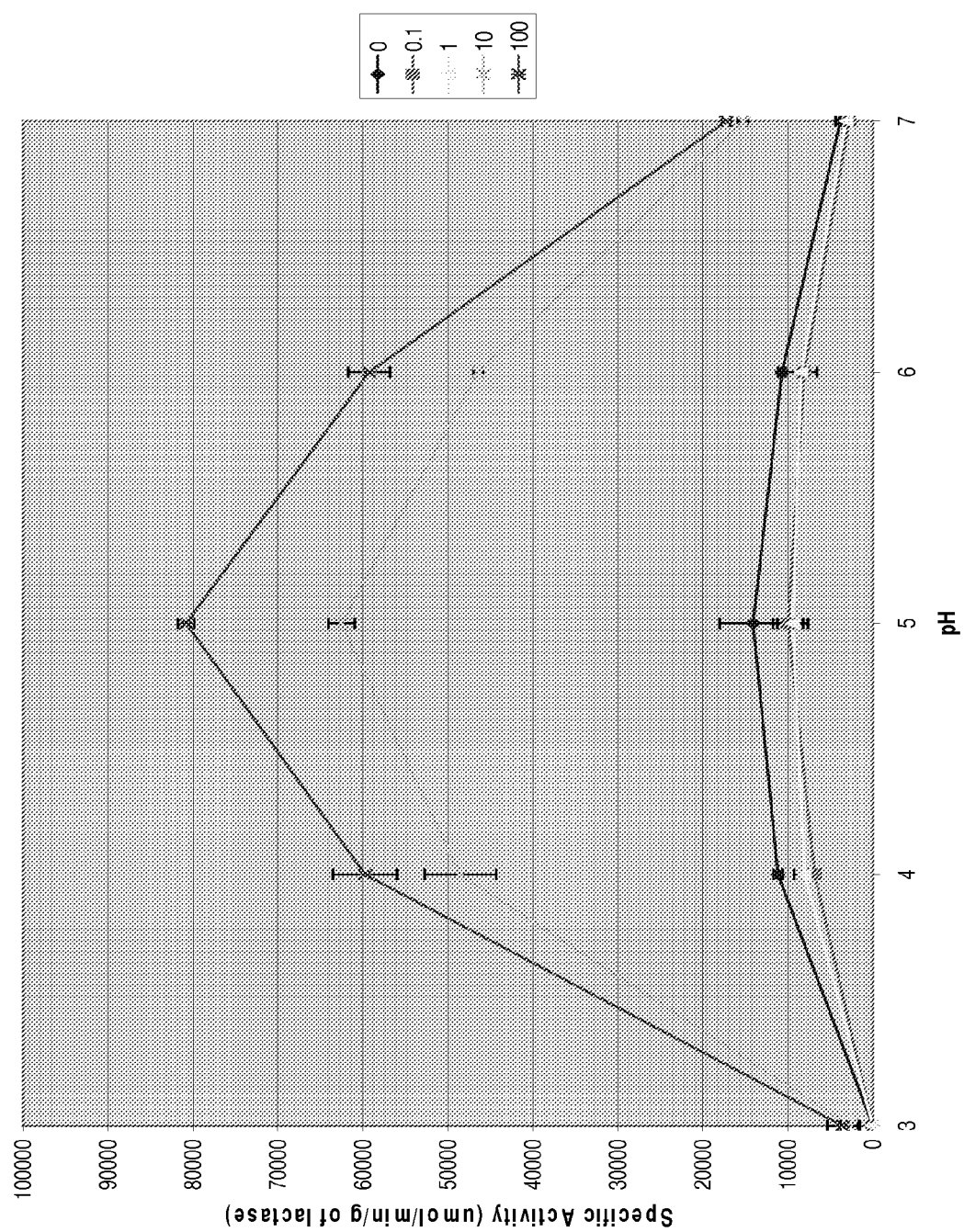

FIG. 53 is a graph of the specific activity of the 100× immobilized enzyme verses pH, respectively, is shown.

Figure 54:
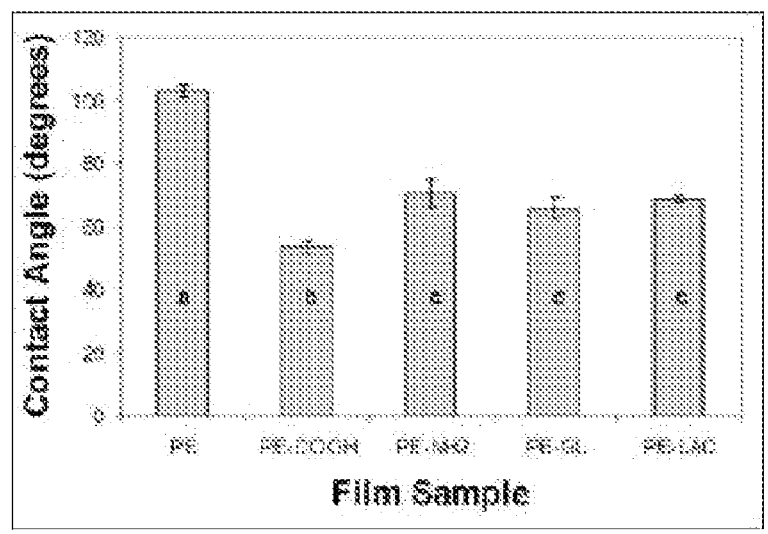

FIG. 54 is a graph of the water contact angle of modified and unmodified films. Values are means of 6 measurements on 1 piece of film (n=6, □/SD). Different letters indicate significant differences (P<0.05).

Figure 55:
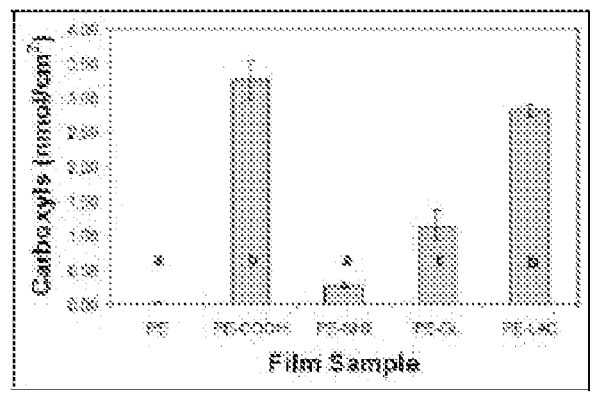

FIG. 55 is a graph of the surface carboxyl concentration of modified and unmodified films. Values are means of 3 independent films (n=3, □/SD). Different letters indicate significant differences (P<0.05).

Figure 56:
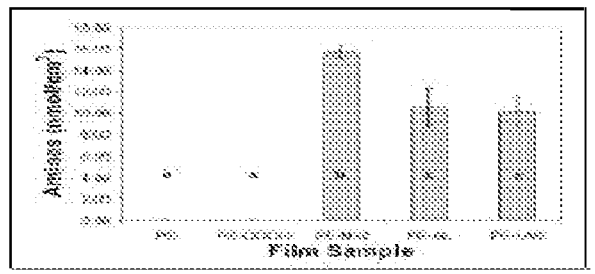

FIG. 56 is a graph of the surface amine concentration of modified and unmodified films. Values are means of 5 independent films (n=5, □}SD). Different letters indicate significant differences (P<0.05).

Figure 57:
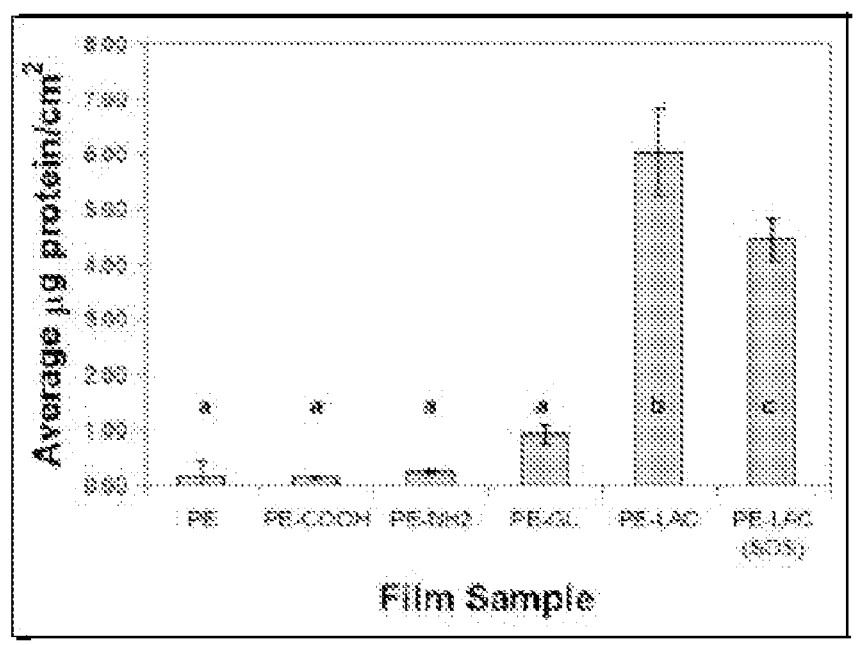

FIG. 57 is a graph of the surface protein concentration of modified and unmodified films. Values, determined by the BCA assay, are means of 3 independent films (n=3, □/SD). Different letters indicate significant differences (P<0.05).

Figure 58:
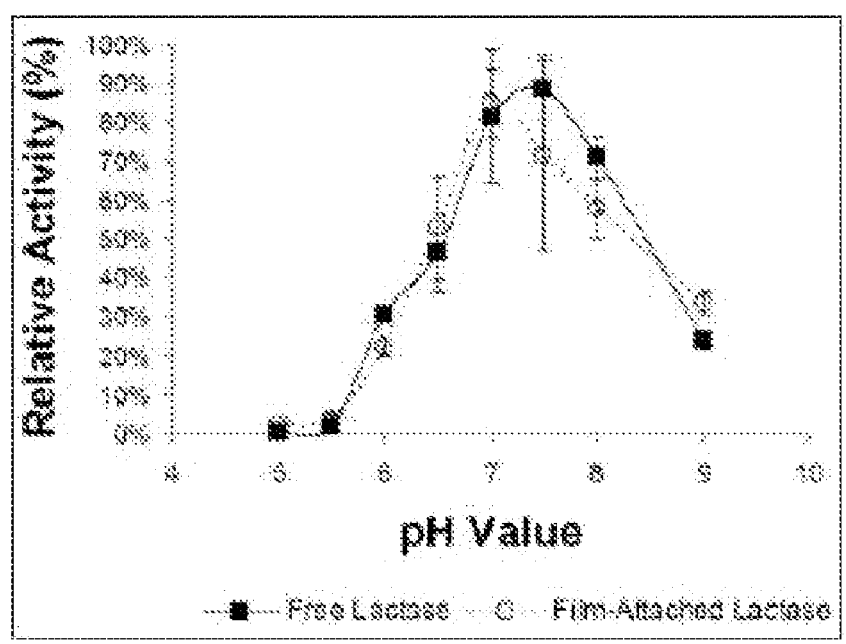

FIG. 58 is a graph of the pH activity profile of free and film-attached lactase. Values are means of 4 independent films (n=4, □/SD). Activities have been normalized to the highest free or film-attached enzyme activity to indicate percent relative activity at each pH value.

Figure 59:
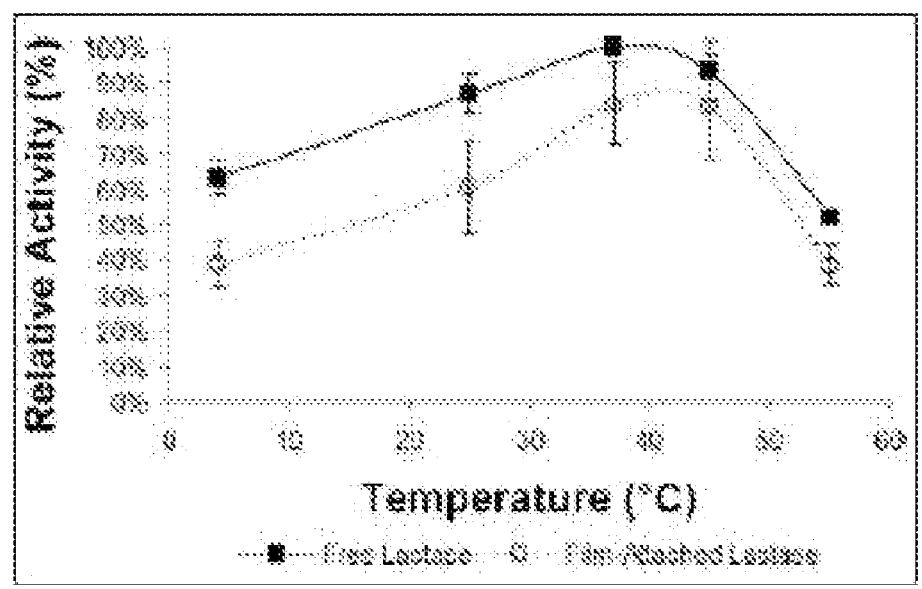

FIG. 59 is a graph of the temperature activity profile of free and film attached lactase. Values are means of 4 independent films (n=4, □}SD). Activities have been normalized to the highest free or film-attached enzyme activity to indicate percent relative activity at each temperature.

Figure 60:
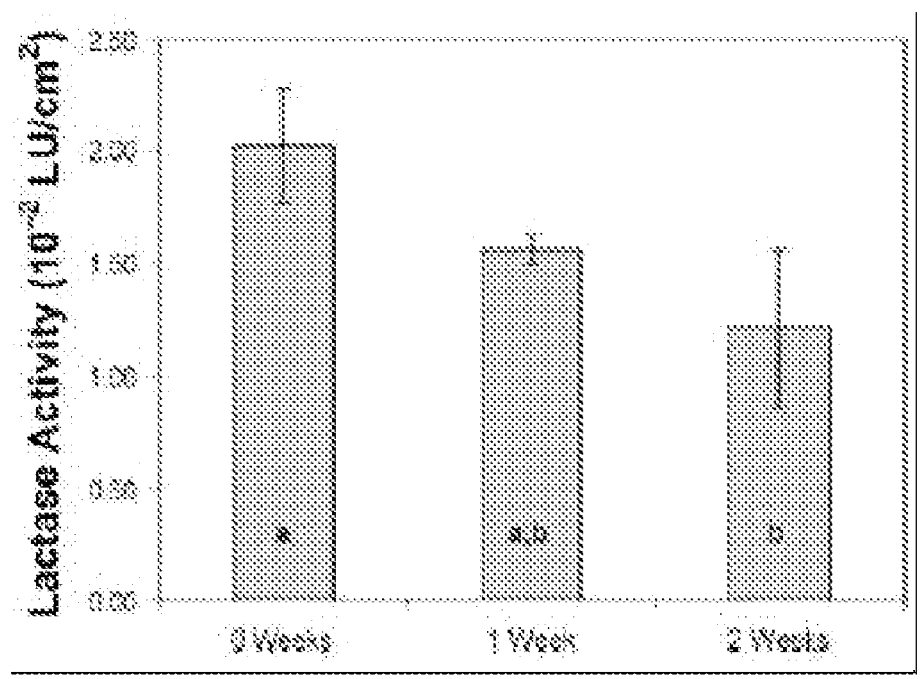

FIG. 60 is a graph of the Lactase activity of films stored in pH 6.8 phosphate buffer at refrigerated conditions. Values are means of 3 independent films (n=3, □/SD). Different letters indicate significant differences (P<0.05). Activities have been reported as lactase units (LU)/cm2, in which 1 LU is defined by the liberation of 1 μmol o-nitrophenol per minute at 37° C.

DETAILED DESCRIPTION OF THE INVENTION

The present invention will be more fully understood and appreciated by reading the following Detailed Description in conjunction with the accompanying drawings, wherein like reference numerals refer to like components.

The present invention addresses the problem of developing a more economical, repeatable, more efficient, more stable, and better adaptable processes and apparatuses for hydrolyzing the disaccharide lactose into constituent galactose and glucose monomers than provided by currently available technology.

Lactase immobilized reactor systems have been explored as economical means to produce lactose-reduced products. Immobilization to a support is an attractive process because it allows for recovery, repeated use, and stabilization. A number of organic and inorganic supports have been employed for immobilization of lactase (as shown in the Tables 1 and 2). Natural supports such (e.g., chitosan, agarose, cellulose) have shown to be suitable in retaining the activity of the enzyme; however, these supports, being hydrophilic, often swell or disintegrate in an aqueous environment thus reducing the mechanical stability and industrial application. Inorganic/nonmetallic composites such as glass and ceramics have also shown to be suitable in preserving enzyme activity after immobilization, particularly when a silica coating or graft is applied. The disadvantages of these materials include cost and the potential for physical hazards if the support contaminated the food product.

Hydrophobic polymers are attractive carriers for enzyme-immobilized applications in the food industry because of mechanical rigidity, low cost, ability to mold into different size and shape arrangements, compatibility with food products, low swelling in aqueous solution, and regulatory approval for food contact. The surface of these supports can be modified to produce functional chemical moieties, such as carboxylic acid groups, that are cable of reacting with biological molecules in a covalent fashion to prevent leakage of the enzyme. The enzyme, lactase β-galactosidase), however, can lose activity when conjugated to these industry-viable carriers, thereby limiting application.

Given the potential applicability of packaging and reactor systems that employ the enzyme, lactase, being covalently immobilized to the surface of a hydropbobic support, an embodiment of the present invention provides a method for retaining enzyme activity after attaching lactase to a hydrophobic polymer support. An embodiment of the present invention also provides products comprising the enzyme attached to the hydrophobic polymer support with such retained enzyme activity.

Advantages of the invention are illustrated by the following Examples. However, the particular materials and amounts thereof recited in these examples, as well as other conditions and details, are to be interpreted to apply broadly in the art and should not be construed to unduly restrict or limit the invention in any way.

Example 1

Lactase is derived from a number of species, though commercial applicability is limited to enzyme from fungal, yeast, and bacterial species. In the food industry, the principal lactase sources are those of *Aspergillus* (sp. *oryzae* and *niger*) and *Kluyveromyces* (sp. *lactis* and *fragilis*). Though both serve to catalyze lactose into glucose and galactose, the optimum catalytic conditions as well as stability under conjugation and storage conditions differ. To determine the suitability of the preparations for immobilization, species from the two organisms, specifically *Aspergillus oryzae* and *Kluyveromyces lactis*, were evaluated for their respective activities and stabilities across multiple conditions in free enzyme form. This Example describes the purification of Lactase from commercial preparations.

A liquid preparation of commercial lactase from *Kluyveromyces lactis* (Valley Research, Inc.: Godo YNL-2), packaged in glycerol, was purified utilizing a two-step filtration method. Initially, 1.5 ml of the enzyme was syringe filtered through a sterile 0.22 um membrane. The product was, subsequently, added to a 2 ml centrifugal ultrafiltration device with a 50,000 molecular weight cut off (MWCO) membrane (Millipore: Centricon YM-50) and centrifuged at 5000×g at 25° C. (120 BCA centrifuge). The supernatant was reconstituted with 0.1M phosphate buffer (pH 7.0) containing 50% glycerol and 10 mM $MgSO_4$ unless otherwise stated.

Lactase from *Aspergillus oryzae* (Enzyme Development Corporation; Enzeco) was purified from a dry sample by reconstituting 20 mg of the commercial preparation in 1.5 ml of 0.1M MES buffer (pH 5.3). The enzyme was syringe filtered through a sterile 0.22 um membrane, and the supernatant added to a 2 ml centrifugal ultrafiltration device with a 50,000 molecular weight cut off (MWCO) membrane (Millipore: Centricon YM-50) and centrifuged at 5000×g at 25° C. (120 BCA centrifuge). The supernatant was reconstituted with 0.1M MES buffer (pH 5.3).

The extent of purification was determined using SDS gel electrophoresis. Samples were denatured by subjecting the enzyme to a temperature of 70° C. for 10 minutes in the presence of SDS. The samples were run on 7% acetate gels (NuPAGE; Novex) using tris-acetate running buffer and a constant voltage of 200V for 35 minutes. The gels were stained using a Coomassie Blue solution (45% v/v water, 45% v/v methanol, 10% v/v acetic acid, and 0.25% w/v Coomassie brilliant blue R250) for 2 hours, and destained using a solution of 50% v/v water, 40% v/v methanol, and 10% v/v acetic acid for intervals of 1 hour, then 12 hours, then 1 hour. Protein bands were compared to protein standards in the range of 40 kDa to 500 kDa (Invitrogen; HiMark Protein Standard).

Figure 1:
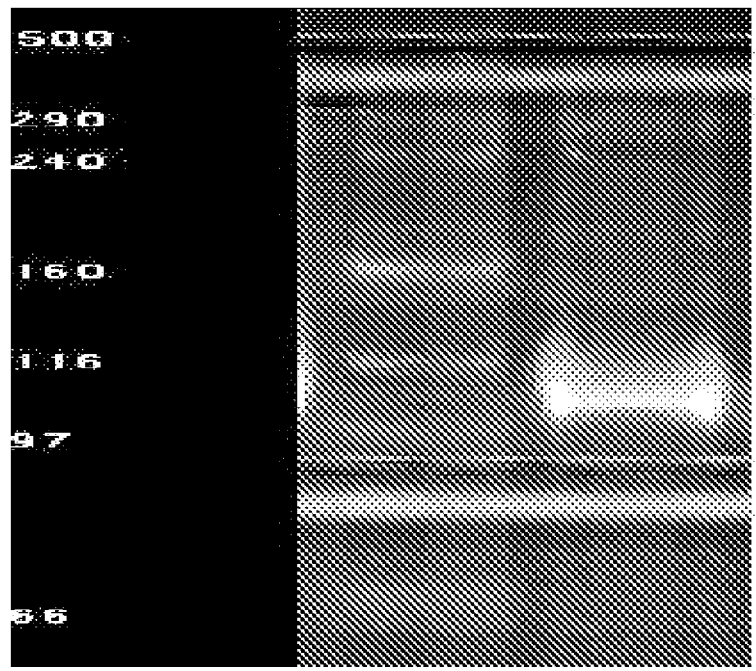
FIG. 1 is a gel electrophoresis of *A. oryzae* (SEQ ID NO: 1) lactase according to an embodiment of the present invention.
Figure 2:
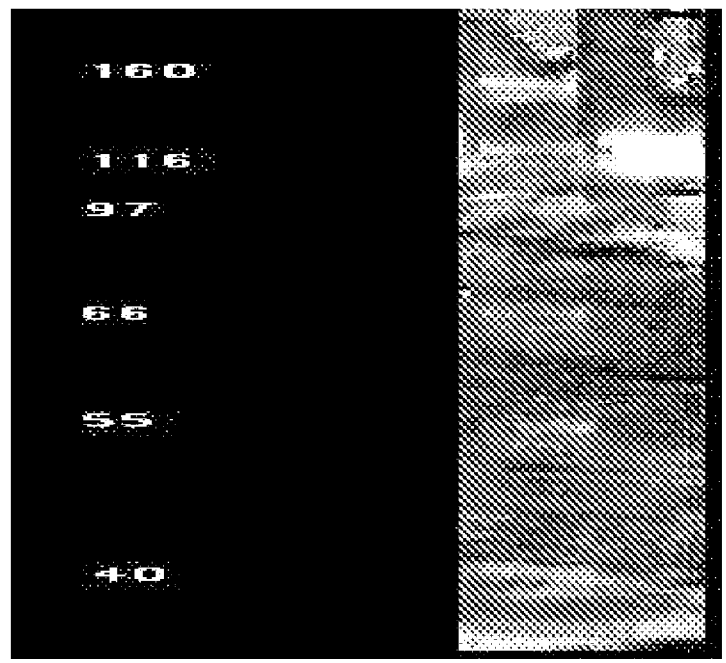
FIG. 2 is a gel electrophoresis of *K. lactis* lactase according to an embodiment of the present invention.

As noted, lactase was purified from commercial preparations to remove stabilizers, extraneous proteins, and cell debris. Syringe filtration (0.22 um) was applied to remove yeast cells (*K. lactis*) or fungal cells (*A. oryzae*) (SEQ ID NO: 1). Stabilizers (glycerol, dextrose, salts) and small non-lactase proteins (ie proteases, lipases, etc.) were, further, removed using centrifugal filtration through 50K MWCO membranes leaving the respective enzymes. The isolated protein was subjected to SDS PAGE with bands seen for *A. oryzae* (SEQ ID NO: 1) (105K Da) (FIG. 1) and *K. lactis* (MW 117K Da) (FIG. 2). These single bands, corresponding to the molecular weight on the enzyme, indicate that the enzymes were appropriately purified, by the described methods, from the commercial preparation and constitute the total protein of the system.

Example 2

This Example describes the determination of lactase specific activity. Lactase specific activity was determined by a modification of Food Chemical Codex method for the determination of acid lactase units. An amount of the enzyme preparation consisting of 2-5 μg was added to 2 ml of a 0.012 mM solution of the synthetic lactose substrate, o-nitrophenyl-β-galactopyranoside, and allowed to react under shaking for 15 minutes. At the completion of the time period, 2.5 ml of 10% sodium carbonate was added to stop the reaction. The solution was diluted to 25 ml with deionized water and the absorbance of 2 ml of the diluted sample was read at 420 nm (Jenway 6300 spectrophotometer). Specific activity was determined using Equation 4 below:

$$\text{Enzyme specific activity } (U) = [(A_{sample} - A_{blank})*(25)]/[(\epsilon)*(t)] \quad \text{Equation 4}$$

Where Asample: absorbance of test sample at 420 nm, Ablank: absorbance of blank (no lactase) at 420 nm, 25: volume of final solution, ml, ε: extinction coefficient (4.54 ml/μmol) using a 1 cm light path length, t: time of reaction, minutes, U: enzyme units (μmol/min/g of enzyme).

As discussed below, lactases from *K. lactis* and *A. oryzae* (SEQ ID NO: 1) were characterized with respect to pH and temperature.

*K. lactis* specific activity as a function of pH was evaluated in the range of 6.0 to 8.5. Phosphate buffer was used between pH 6 and pH 7.5 (0.1M) and borate buffer was used for pH 8.0 and 8.5 (0.1M) at 30° C.

*K. lactis* specific activity as a function of temperature was evaluated in the range of 25° C. to 55° C. at pH 7.0 (0.1M phosphate buffer) using an IsoTemp 125D heating block (Fisher Scientific).

*A. oryzae* (SEQ ID NO: 1) specific activity as a function of pH was evaluated in the range of 3.5 to 7.0. Citrate-dipotassium phosphate buffer was used at pH 3.5, acetate buffer (0.1M) was used from pH 4.0 to pH 6.0, and phosphate buffer (0.1M) was used for pH 6.0 to pH 7.0.

*A. oryzae* (SEQ ID NO: 1)specific activity as a function of temperature was evaluated in the range of 30° C. to 70° C. at pH 5.0 (0.1M acetate buffer) using an IsoTemp 125D heating block (Fisher Scientific).

Figure 3:
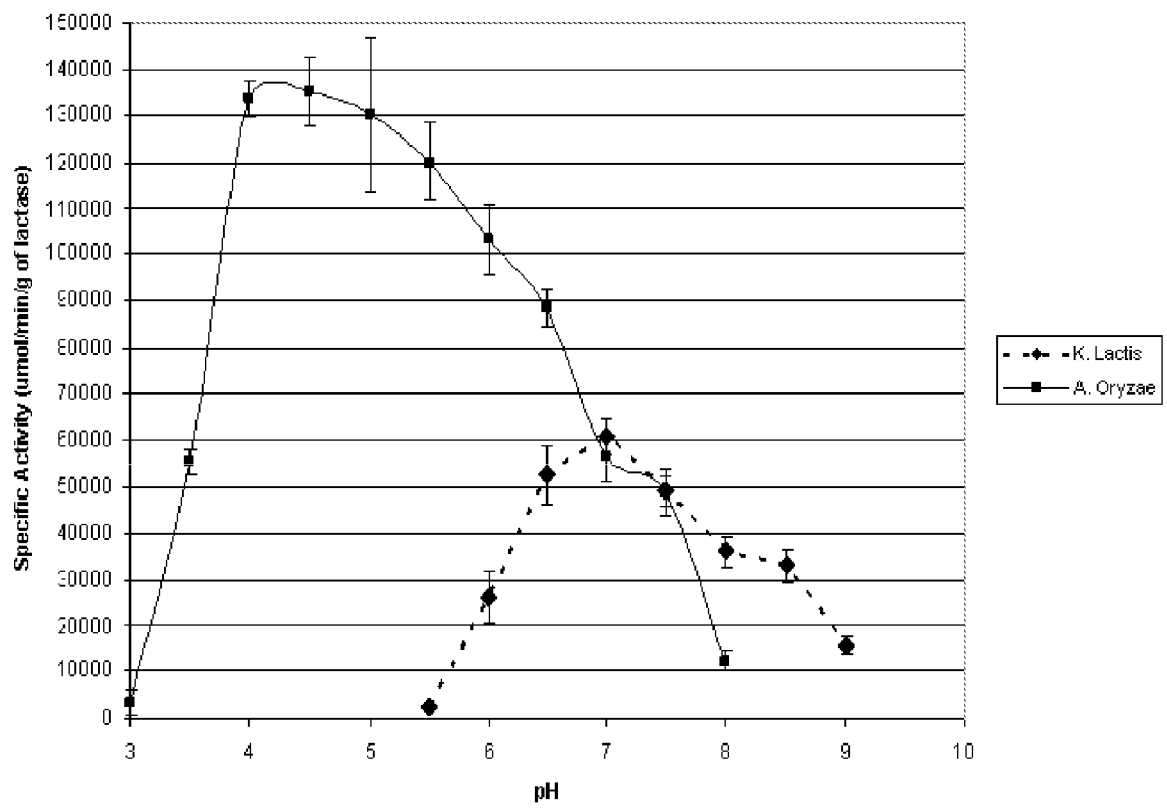
FIG. 3 is a graph showing the effect of pH on free lactase (*A. oryzae* (SEQ ID NO: 1) and *K. lactis*) activity at 50° C. for *A. oryzae* (SEQ ID NO: 1) and 30° C. for *K. lactis* using ONPG as enzyme substrate. Values represent mean values±standard deviation (N=3).
Figure 4:
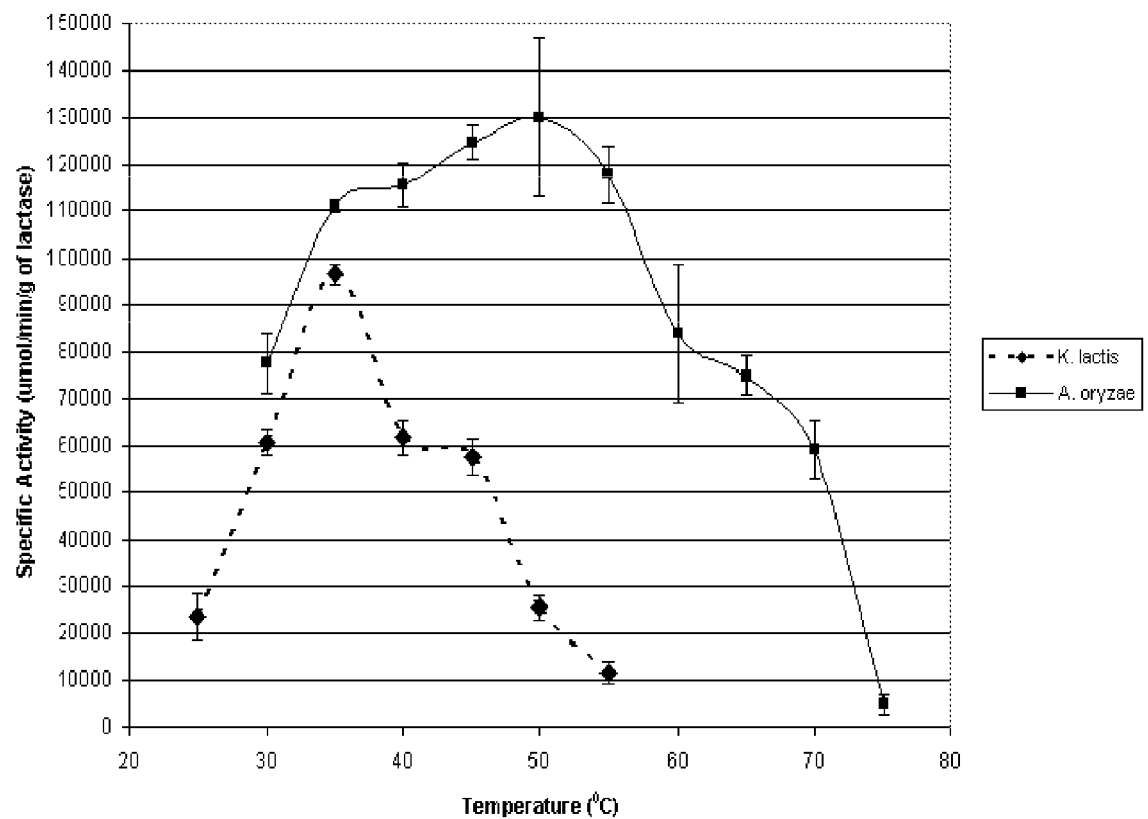
FIG. 4 is a graph showing the effect of temperature on free lactase (*A. oryzae* (SEQ ID NO: 1) and *K. lactis*) activity at pH 5.0 for *A. oryzae* (SEQ ID NO: 1) and pH 7.0 for *K. lactis* using ONPG as enzyme substrate. Values represent mean values±standard deviation (N=3).

The results showed that the free *K. lactis* lactase shows an optimum activity at neutral pH (7.0) (FIG. 3) and 35° C. (FIG. 4), with a maximum activity approaching 98Kumol/min/g of lactase. Though optimum activity of *K. lactis* lactase is 35° C. in its native form, it has been noted that the stability of the enzyme, without stabilizers, can be effected by pH at that temperature. Beyond 55° C., the enzyme was rapidly inactivated. *A. oryzae* (SEQ ID NO: 1) lactase held optimum activity at a more acidic pH (4.0-5.0) (FIG. 3) and a higher temperature (50° C.) (FIG. 4), with maximum activity of 133Kumol/min/g of lactase. Conditions above 50° C. would be beneficial for immobilized lactase preparations in deterring microbial growth rate of mesophilic organisms—favoring the *aspergillus* species. For lactose reduction of dairy products, lactase from *K. lactis* is favored for fluid milk processing because of the optimum activity near that of fluid milk (pH 6.8). *A. oryzae* (SEQ ID NO: 1) lactase is more often used for whey processing, which takes places at acidic pH (<6.0). Though lactase from *K. lactis* would not be able to be used for whey processing because of the inactivity at the necessary acidic pH, *A. oryzae* (SEQ ID NO: 1) lactase may be used for fluid milk processing because it retains activity at pH 7.0 and 50° C. (58Kumol/min/g of lactase), provided the enzyme is stable at that pH.

Example 3

This Example describes the evaluation of the stabilities of the two enzymes of the previous Examples to investigate potential applicability to lactose reduction in whey and fluid milk processing. *K. lactis* lactase stability has been shown to be influenced by magnesium and the presence of glycerol at temperatures above the optimum for catalytic activity (35° C.). Investigation was preformed into the stability of the enzyme with and without magnesium and glycerol at controlled room temperature (25° C.; pH 6.8) and refrigerated temperature (4° C.; pH 6.8).

*K. lactis* stability was determined by reconstituting purified *K. lactis* with one of the following four solutions: 1) 0.1M phosphate buffer; 2) 0.1M phosphate buffer containing 10 mM $MgSO_4$; 3) 0.1M phosphate buffer containing 50% v/v glycerol; or 4) 0.1M phosphate buffer containing 50% v/v glycerol and 10 mM $MgSO_4$. Each preparation was stored at 4° C. and 25° C., and the specific activity at 25° C., pH 7.0 (0.1M phosphate buffer) was periodically determined across a 21-day period.

Figure 5:
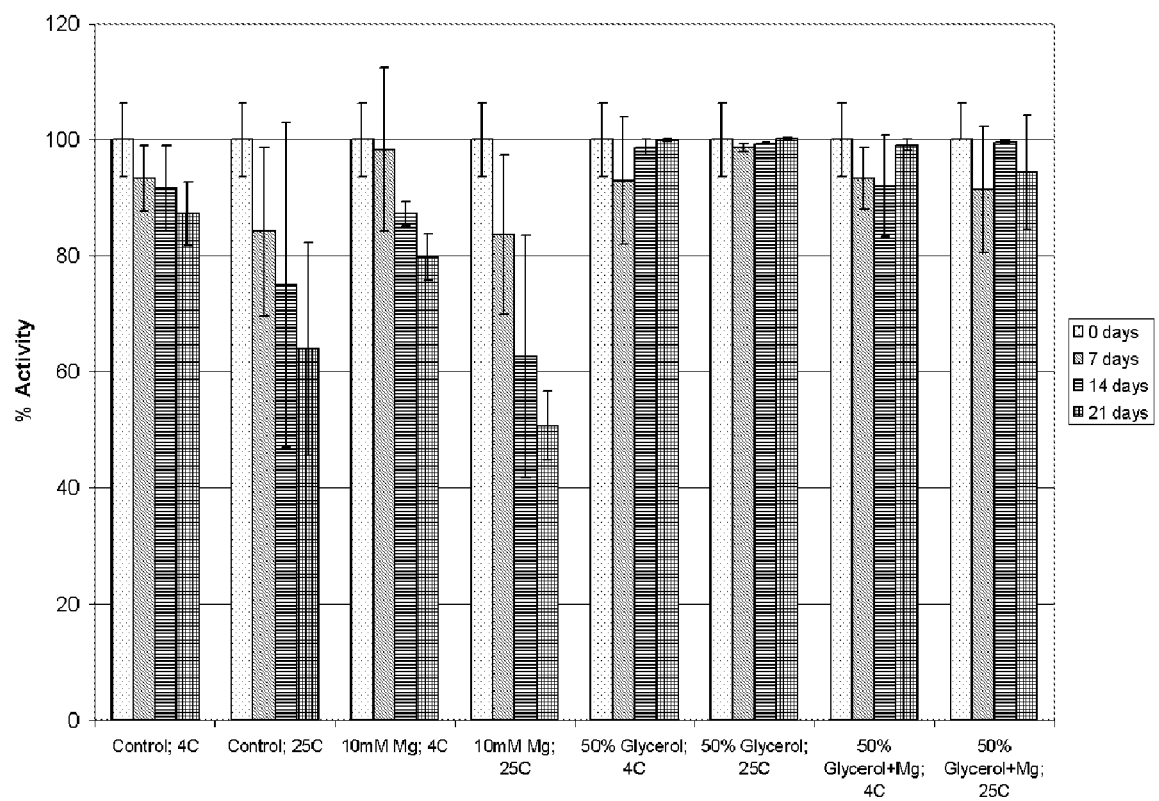
FIG. 5 is chart showing the stability of free lactase (*K. lactis*) at 25° C., pH 7.0 for *K. lactis* using ONPG as enzyme substrate. Values represent mean values±standard deviation (N=3).
Figure 6:
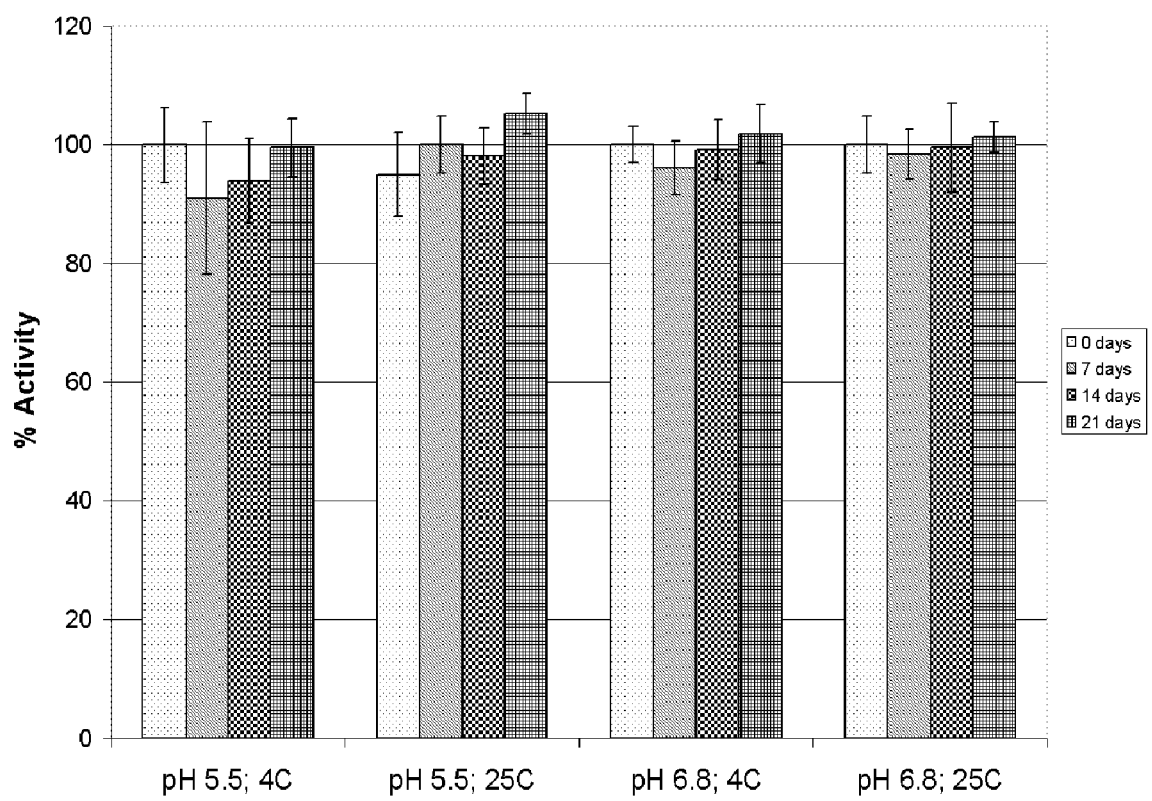
FIG. 6 is chart showing the stability of free lactase (*A. oryzae*). (SEQ ID NO: 1) Activity at 50° C., pH 5.0 for *A. oryzae* (SEQ ID NO: 1) using ONPG as enzyme substrate. Values represent mean values±standard deviation (N=3).

The results showed that at higher temperature (25° C.), the enzyme was less stable across the three week period with or without magnesium than at (4° C.) (FIG. 5). At 4° C., the control and "magnesium only" samples showed a significant reduction in activity at the end of the three week period. Glycerol (50%), had a significant ($p<0.05$) stabilizing effect across the three week period on *K. lactis* lactase at both 4° C. and 25° C., compared to preparation without glycerol—independent of magnesium (FIG. 5). As can be seen from FIG. 5, no significant loss of activity was observed across the three week period when the enzyme was in the presence of glycerol. These results indicate that glycerol, in which the commercial lactase of *K. lactis* is packaged, is used to retain the stability of the free enzyme. Glycerol has demonstrated an ability to promote the stability of proteins, the exact mechanism for this stabilization; however, is still being investigated. Glycerol can mimic the cellular environment—promoting preferential hydration/solvation of the enzyme surface, and protein association. The explanation agrees with the nature of K. lactis lactase, which is an intracellular enzyme that is active in dimer and tetramer forms through association of identical subunits, but not as a monomer. Removing the enzyme from the native environment into a dilute aqueous condition will alter the quaternary and tertiary dynamics, shifting the equilibrium of the native and unfolded state. The necessity of dimer association for catalytic activity suggests that the active site of the enzyme is shared between subunits or interaction promotes a shift in catalytic cleft. In solution, the association-dissociation of subunits making up the quaternary structure is dynamic. During immobilization, the quaternary structure of the lactase, consequently, needs to be retained in the dimer position. Glycerol can, also, effect the hydrogen bonding structure of water to proteins. Because of the necessity of the bound water layer in supporting tertiary structure stabilization, the presence of glycerol may aid in the promotion of these bonds.

A. oryzae (SEQ ID NO: 1) stability was determined by reconstituting purified K. lactis with one of the following four solutions: 1) 0.1M MES buffer pH 5.5; or 2) 0.1M MES buffer pH 6.8. Each preparation was stored at 4° C. and 25° C., and the specific activity at 50° C., pH 5.0 (0.1M acetate buffer) was periodically determined across a two week time period.

Lactase (A. oryzae) (SEQ ID NO: 1) kinetics: The Michaelis constant of native and immobilized β-galactosidase was determined. An 8 mM ortho-nitrophenyl-β-Galactopyranoside (Sigma: ONPG, N-1127, MW 301.3) solution was diluted in 0.1 M acetate buffer (pH 5.0). The 8 mM ONPG solution was then serially diluted, establishing a substrate range from 0 to 8 mM. Lactase (2.5-5 ug) was added to individual tubes containing the ONPG (with a concentration of 0-8 mM) at 50° C. The solution was continuously shaken for four minutes with representative tubes stopped every 30 seconds by the addition of 2.5 ml of 10% sodium carbonate. The absorbance was spectrophotometrically measured at 420 nm. The Michaelis constant ($K_m$) was extrapolated from non-linear regression using Michaelis-Menten enzyme kinetics (Equation 5, below) (Graphpad Prism software).

$$\text{Velocity} = V_{max} * [S] / K_m + [S] \quad \text{Equation 5}$$

Where $V_{max}$=Maximum velocity (mM/min), [S]=Substrate concentration (mM), and $K_m$=Substrate concentration to achieve half $V_{max}$ As noted, the storage stability of A. oryzae (SEQ ID NO: 1) lactase was evaluated under whey and fluid milk pH processing conditions (pH 5.5 and 6.8, respectively) at controlled room temperature (25° C.) and refrigeration conditions (4° C.). The results showed that temperature and pH had no significant effect (p<0.05) on the retained activity of the enzyme across a three week evaluation period. Stability results indicate that A. oryzae (SEQ ID NO: 1) lactase can, with respect to storage pH, be used for both whey and fluid milk processing.

Unlike, K. lactis lactase, A. oryzae (SEQ ID NO: 1) lactase is an extracellular enzyme that is active as a monomer (ie no quaternary structure), and commercially available in a lyophilized powder form. Extracellular enzymes are typically more stable than intracellular enzymes because of localized environmental changes during intracellular folding, expression, and extracellular activity, which warrants robustness. Because A. oryzae (SEQ ID NO: 1) lactase has catalytic function as a monomer and no requirements for quaternary structure, concerns of multiple subunit stabilization during immobilization are alleviated. Lactase from A. oryzae (SEQ ID NO: 1) was determined to be a more suitable candidate than K. lactis lactase for immobilization because of the stability and activity across pH conditions useful for processing and covalent conjugation, long-term stability in aqueous conditions without the need for stabilizers, high catalytic activity at temperatures above the growth optimum for mesophilic organisms, ability to retain activity after sanitation procedures, and lack of quaternary structure requirements.

Example 4

This Example describes the covalent immobilization of lactase on polystyrene-co-acrylic acid microspheres and the effect of carboxylic group concentration.

Previous attempts to covalently immobilize lactase to oxidized packaging films produced no measurable lactase activity Since this loss of activity could not be explained, a model system for conjugation of the enzyme was developed to lay a foundation to eliminate and introduce variables for study. Investigations on the covalent immobilization of lactase to hydrophobic supports focused on the attachment of A. oryzae (SEQ ID NO: 1) lactase to polystyrene-co-acrylic acid microspheres (~1 μm).

For covalent attachment, both the carrier and the enzyme need to have functional groups capable of reacting in a covalent fashion. Though enzymes have native functionality (carboxylic acids, amine, thiols, etc.), hydrophobic carriers are typically inert and need to be made reactive. Introduction of carboxylic groups to hydrophobic polymers is a simple means of creating surface functionality, and can be achieved using diverse methods. Methods for generating carboxylic group functionality include wet chemical treatments, plasma oxidation, corona discharge, flame ionization, and copolymerization with a carboxylic containing monomer (ie acrylic or methacrylic acid). Because of the wide potential applicability and ease of introduction of carboxylic acid functionality to other polymer systems such as food packaging films, a carboxylic acid-containing hydrophobic polymer system was deemed a desirable platform for lactase immobilization. Unlike surface oxidation, introduction of acrylic acids monomers allows the number of carboxylic groups to be tailored in a control fashion without introduction of oxidation byproducts such as hydroxyl or aldhehyde groups that may form using alternative carboxylic group generating methods.

Though particles greater than 100 μm (100 μm-2 mm) are used in immobilized enzyme applications because of pressure drops associated with smaller particles, 1 μm microspheres were chosen because they provide high surface area for two dimensional surface, promote increased Brownian motion that enhances substrate/surface interaction, and, unlike nanomaterials, can be readily separated by centrifugation. Two dimensional supports were employed to reduce variability of protein and substrate diffusion associated with porous carriers, limit swelling, and develop model applicability of two-dimensional systems to alternative polymer-enzyme systems such as packaging films.

Microspheres (Bangs Laboratories, Inc.) were composed of polystyrene-co-acrylic acid with a size range of 1.1-1.2 μm and were characterized. The microspheres were cleaned by removing surfactant from the commercial microsphere preparation by centrifugal spinning of an allocated volume of microspheres at 10,000×g (Fisher microcentrifuge Model 235) in low bind polypropylene microcentrifuge tubes (Eppendorf), removing the supernatant, replacing with water, spinning, and repeating the process with 0.1M MES buffer pH 5.5, 0.1M phosphate buffer pH 7.5, water, and finally desired conjugation or storage buffer.

Available carboxylic groups on the surface of the microspheres were quantified using the Toluidine Blue assay. Microspheres were immersed in 1 ml of $5 \times 10^{-4}$M Toluidine Blue 0 in distilled water that had been adjusted to pH 10 by NaOH. After three hours of shaking at room temperature, the microspheres were centrifuged and the supernatant dye removed. The microspheres were rinsed three times with NaOH solution at pH 10 to remove non-complexed dye. Complexed dye was then desorbed by shaking microspheres three times in 1 ml, 50% v/v acetic acid for 15 minutes at room temperature, followed by centrifugation and removal of the desorbed dye into a cuvette. The absorbance of the desorbed dye was read at 633 nm, and surface carboxyl groups were determined by comparison with a standard curve of dye, knowing the quantity of microspheres and the volume of the desorbing solution under the assumption of one mole of dye complexing with one mole of available carboxyl groups.

Lactase was covalently immobilized onto polystyrene-co-acrylic acid microspheres through a two-step process to form an amide bond. Carboxylic acid groups on the surface of the microspheres were, initially, modified by a 10 mole excess (in relation to the number of total carboxylic acid groups) of 1-ethyl-3-(3-dimethylaminopropyl) carbodiimide (EDC) in the presence of 100 mole excess (in relation to the number of total carboxylic acid groups) of N-hydroxysuccimide (NHS). The reaction was allowed to proceed for one hour at 25° C. at pH 5.5 in 1.5 ml of a 0.1M MES buffer solution to yield an activated succinimdyl ester on the surface of the microspheres. Excess reagent was removed with the supernatant following centrifugation at 10,000×g. The wash step was repeated with 0.1M MES buffer pH 7.0. A 1.5 ml increment of lactase (A. oryzae) (SEQ ID NO: 1) in 0.1M MES buffer, pH 7.0 was added to the activated microspheres in a 5 mole excess (in relation to the theoretical value of the amount of enzyme that could be immobilized) and allowed to react for 2 hours at 2° C. under constant shaking. Enzyme that had not been immobilized was separated by centrifugation as described, previously, for excess reagent until no further protein was detected in the supernatant as determined by addition of 0.5 ml of the supernatant to 3 ml of Bradford reagent and compared to the control containing no enzyme.

Figure 7:
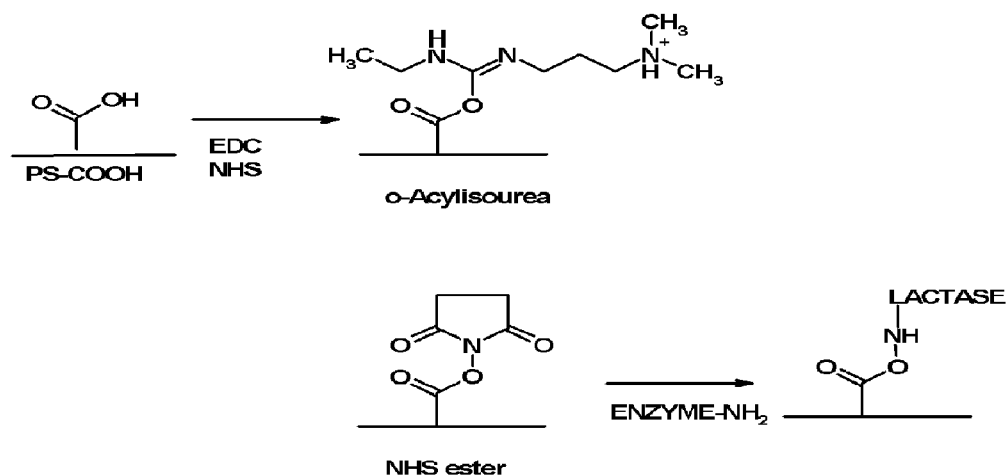
FIG. 7 is a schematic showing EDC/NHS activation of carboxylic groups followed by enzyme conjugation. R—NH$_2$ is indicative of available lysine residues of lactase.

As noted, lactase (A. oryzae) (SEQ ID NO: 1) was conjugated to the microspheres by a two-step carbodiimide reaction (FIG. 7). The carbodiimide (EDC) reacts with the surface carboxylic groups of the microspheres, which in the presence of NHS forms an activated NHS-ester intermediate. In the second step, NHS-ester activated microspheres react with primary amine groups (lysine) on the enzyme surface, forming a "zero length" amide bond after loss of the leaving group from the nucleophilic substitution reaction. The carbodiimide can react with the enzyme and microspheres in a one-step reaction by reaction of amine groups on lactase and carboxylic acid groups on the carrier, but this method may produce intra or intermolecular modification with enzyme carboxylic groups. An advantage of EDC/NHS chemistry is that the reagents are water soluble, which, unlike organic solvent reactions (ie carbonyldiimidazole), is beneficial to enzyme stability and prevents swelling of the synthetic polymer microspheres. For food immobilized enzyme applications, a concern is the use of bioconjugate reagents that may be detrimental to human health if ingested or in contact. By employing carbodiimide chemistry, unreacted activated groups are hydrolyzed back to the corresponding carboxylic acid. Carbodiimide hydrolyzes in water and has a half life of 2-3 seconds when forming the o-acylurea product with carboxylic groups. In the presence of NHS; however, the activation half-life is extended to minutes or hours. The functionality of the NHS-ester, also hydrolyzes back to carboxylic acid groups, leaving no activated functional groups after immobilization that could react with components of a food system. The EDC/NHS reaction can facilitate covalent attachment of biological free amines (ie lysine) to carboxylic acid-functionalized supports at pH 7.0—allowing for conjugation of the enzyme to the support at conditions that promote enzyme stability. Also, the "zero length" between the support and the enzyme allows for covalent surface-surface studies between the protein without the introduction of spacer length variability.

Example 5

This Example describes the determination of the protein concentration of free and immobilized enzyme on the microspheres as described in Example 4 using the BCA assay, which relies on peptide bonds associated with a protein to reduce a solution of copper in biochomic acid. Free or immobilized (0.1 ml) was added to 2 ml of the BCA solution and the reaction took place at 60° C. for 30 minutes. After completion of the reaction period, microspheres were removed from the solution by centrifugation at 10,000×g and passing the supernatant through a 0.22 μm syringe filter. The absorbance of the microsphere-free solution was read at 562 nm and compared to a standard curve of 0-20 μg of bovine serum albumin (BSA).

Protein concentration of free lactase was, also, determined by the dye binding method described by Bradford when BCA-interfering buffers or reagents were present. Free lactase was diluted to an estimated 0.1-1.4 mg/ml in 0.1M phosphate buffer (pH 6.7). Of the diluted solutions, 0.1 ml was added to a glass tube and, subsequently, 3 ml of Bradford Reagent (Sigma, B 6916) that had been brought to room temperature, was added bringing the total volume to 3.1 ml. The solution was then capped, vortexed, and incubated at ambient temperature for 30 minutes. The absorbance was read in a spectrophotometer at 595 nm and compared to a standard curve using bovine serum albumin (BSA). Protein concentration was extrapolated from the regression equation derived from the standard curve and the result was multiplied by the dilution factor to obtain total concentration.

The extent of covalent modification was also determined. Covalent immobilization was distinguished from ionic adsorption through the use of an ionic detergent. Microspheres were diluted in 1 ml of a 1% w/v sodium dodecyl sulfate (SDS) in deionized water solution and heated for 10 minutes at 70° C. Protein concentration, using the BCA method, was determined and compared to a control sample prepared in the same manner without SDS.

The results show that immobilization of lactase on polystyrene-co-acrylic acid microspheres (87 $Å^2$ between surface groups) yielded a protein loading on the carrier of 6.9 (±1.9) mg of lactase/g of microspheres. There was no significant change (p<0.05) in protein loading after subjecting the immobilized enzyme to denaturing conditions in the presence of SDS—confirming the covalent nature of the attachment. The isoelectric point of lactase (4.6) gives the enzyme a negative net charge under conjugation conditions (pH 7.0), which favors preferential association of positively charged amino acids. The theoretical size of a protein having the molecular weight of lactase (MW 105 KDa) would be 7 nm in diameter. Experimental observation using dynamic light scattering indicate that A. oryzae (SEQ ID NO: 1) lactase may be up to 12 nm in diameter, but concede that observations may be skewed by enzyme purity, aggregation, and equipment limitations. Based on the available surface area per gram of the microspheres and assuming lactase to be in a sphere with a diameter of 7 nm with half of the enzyme surface area contributing to protein loading, a theoretical value of 10.7 mg of lactase/g of microspheres can be derived for monolayer coverage (Equation 6, below). This result suggests that experimental surface coverage is approaching that of a monolayer.

Equation 6:
Area of a sphere=$4\pi r^2$
Enzyme diameter=7 nm
Available surface area of microspheres=$4.72 \times 10^{12}$ µm$^2$/g
$4.72 \times 10^{12}$ µm$^2$/g/$(4\pi(0.0035$ µm$)^2)$=$3.07 \times 10^{16}$ enzyme molecules per g of microspheres Since the spherical enzymes are in contact with a flat surface, only the enzyme to half radius would contribute to protein loading giving $(3.07 \times 10^{16}$ enzymes/g of $MS) \times (2)$=$6.14 \times 10^{16}$ enzymes/g of $MS$       Equation 6

Figure 8:
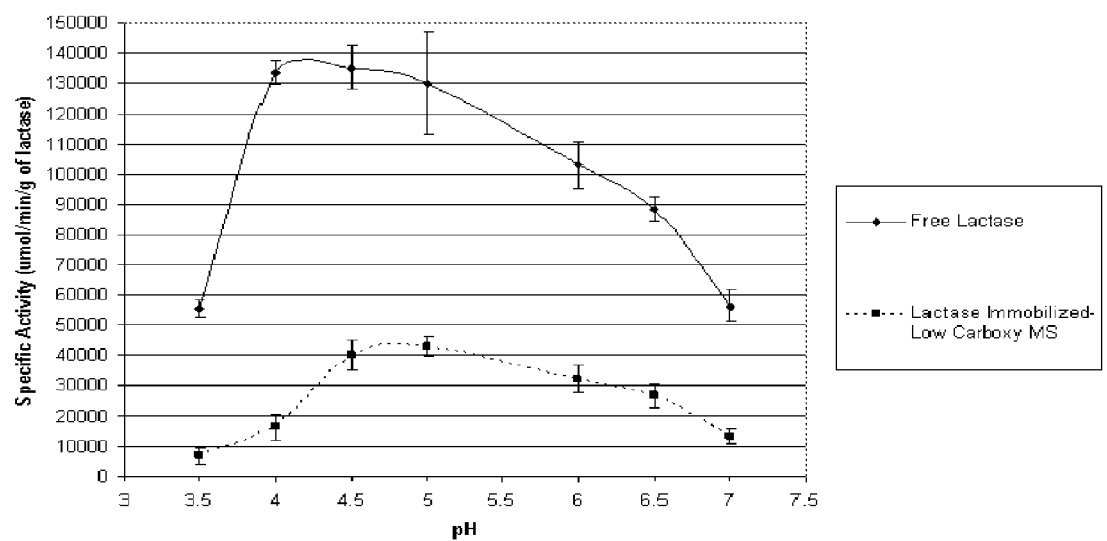
FIG. 8 is a chart showing the effect of pH on free lactase (*A. oryzae*) (SEQ ID NO: 1) and covalently immobilized lactase on polystyrene-co-acrylic acid microspheres (1.2 um; 87 Å2 between carboxylic groups) at 50° C. using ONPG as enzyme substrate. Values represent mean values±standard deviation (N=3).
Figure 9:
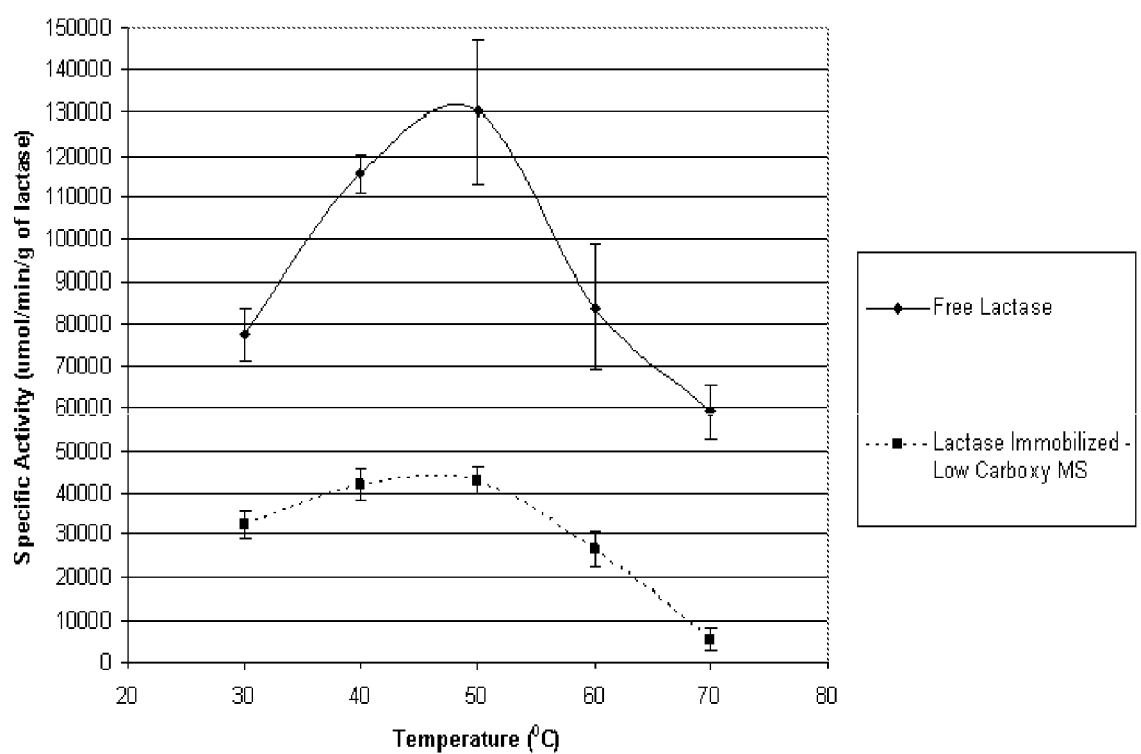
FIG. 9 is a graph showing the effect of temperature on free lactase (*A. oryzae*) (SEQ ID NO: 1) and covalently immobilized lactase on polystyrene-co-acrylic acid microspheres (1.2 um; 87 Å2 between carboxylic groups) at pH 5.0 (0.1M acetate buffer) using ONPG as enzyme substrate. Values represent mean values±standard deviation (N=3).

Using Avargado's number and the molecular weight of lactase gives:

$(6.14 \times 10^{16}$ enzymes/g of $MS)/(6.02 \times 10^{23}$ enzyme molecules/mol$\times$
(105,000 g of lactase/mol)=
10.7 mg of lactase/g of $MS$ Immobilization of the enzyme resulted in a 67% mean decrease in specific activity compared to the free enzyme under optimum conditions as determined by the conversion of ONPG to ONP (FIG. 8, FIG. 9). There was no change in the optimum catalytic temperature (50° C.), but the apparent optimum pH shifted from 4.5 for the free enzyme to 5.0 for the immobilized enzyme (FIG. 8). The shift in pH optimum can be attributed to localized pH at the surface due to the presence of carboxylic groups. The bulk pH may, for example, be 5.0, but the hydrogen ion concentration is greater near the negatively charged surface, yielding a more acidic pH at the surface interface. Factors affecting the loss of activity after immobilization on two dimensional supports can be attributed to hydrophobic interactions between the protein and the surface, loss of mobility, microenvironmental pH shifts, mass transfer limitations/substrate accessibility, surface regularity, protein-protein interactions/crowding, van der Waal forces, orientation, cofactor disassociation, bioconjugation chemistry, active site/necessary amino acid modification, Brownian motion, dehydration of the enzyme-bound water layer, distance from the surface, subunit disassociation (loss of quaternary structure, electrostatic interaction/repulsion between the enzyme and carrier surfaces, curvature of the carrier, competitive hydrogen bonding. These factors may occur alone or in combination to reduce activity of the conjugated enzyme.

Example 6

This Example describes the immobilization of lactase to polystyrene-co-acrylic acid microspheres (1.2 µm) having size and surface characteristics as described in the Examples supra, but with a greater density of available carboxylic acid groups (6.2 Å$^2$ between surface carboxylic acid groups compared to 87 Å$^2$ between surface groups) (Table 3, below). This was done to elucidate the reason(s) for loss of enzyme activity. The "high carboxylic acid" carrier increases the surface charge, hydrophilicity, and potential for multipoint binding relative to the "low carboxylic acid" support—allowing for probing of the effect of these variables on enzyme activity. Lactase was immobilized in an identical manner as described in the Examples supra, to control for conjugation effects.

TABLE 3

| Microsphere characterization | | |
|---|---|---|
| | High Carboxyl | Low Carboxyl |
| Mean Diameter (µm) | 1.1 | 1.2 |
| Binding Capacity | 0 | N/A |
| Surface Titration Data (µeq/g) | 137.3 | 9 |
| Number of Microspheres/gram | 1.34E+12 | 1.04E+12 |
| Surface Area (µm$^2$/g) | 5.13E+12 | 4.72E+12 |
| Parking Area (Å$^2$/Surface Group) | 6.2 | 87 |
| Number of Microspheres/ml | 1.42E+11 | 1.05E+11 |

Protein loading (4.7±1.6 mg of lactase/g of support) on the "high carboxylic acid" microspheres was not significantly different (p<0.05) compared to loading on the "low carboxylic acid" microspheres. A significant reduction in maximum enzymatic activity (p<0.05); however, occurred after conjugation of lactase to the high carboxylic acid microspheres (FIG. 10, FIG. 11). Relative to the activities of the free enzyme and the enzyme when conjugated to low carboxylic acid microspheres, attachment of lactase to high carboxylic acid microspheres resulted in a mean 89% reduction (relative to the free lactase) and 66% reduction (relative to the low carboxy-conjugated lactase) of specific activity under optimum conditions, respectively. There was also no significant difference (p<0.05) in the Michaelis constant ($K_m$) of the lactase on the high carboxylic acid microspheres (0.78±0.21), low carboxylic acid microspheres (0.72±0.25), or the free enzyme (0.83±0.22)—suggesting that activity is not a localized function of the substrate (as expected given the uncharged nature and high concentration of the substrate in combination with the size/two-dimensional nature of the microspheres). These results indicate that electrostatic attraction and/or repulsions between the negatively charged carrier and the enzyme surface may promote enzyme structural instability and loss of activity on the support. Alternatively, enhanced multipoint conjugation to enzyme amine groups that results from a carrier having increased functionality, counter ion (Na$^+$) accumulation at the electrostatic double layer, or changes in hydrogen bonding pattern with the more hydrophilic carrier surface, provide explanations as to the loss of activity.

Example 7

This Example describes the modification of lactase for immobilization on polystyrene-co-acrylic acid microspheres (as described supra).

Controlling the extent of polymer surface functionality can be difficult when using wet chemistry, plasma oxidation, and chemical modification techniques because of the inherent nature of these processes to uniformly alter the surface. Likewise, the distribution of charged amino acids on the surface of enzymes is not always uniform; rather clusters of ionic groups have been observed. With these limitations and the objectives of both: (1) determining if inactivation of lactase when immobilized to carboxylic acid functionalized polystyrene microspheres results from protein-carrier interfacial electrostatic interactions, surface hydrophilic/hydrophobic balance, counter ion accumulation, or multipoint attachment; and (2) exploring means of retaining enzymatic activity of carboxylic acid functionalized hydrophobic polymers—enzyme surface modification was investigated.

Chemical modification of enzymes is used to change solubility, thermostability, and/or evaluate structure/function relationships. Though often utilized to evaluate properties of the free enzyme, this fundamental concept was applied to immobilized lactase by covalently blocking surface-available carboxylic (i.e., aspartic and glutamic acid) of lactase with low molecular weight molecules prior to immobilization on low and high carboxylic acid polystyrene-co-acrylic acid microspheres.

Lactase was modified by blocking the carboxylic acid groups of the enzyme by the formation of an amide bond between free carboxylic acids and glucosamine. Purified lactase was added to 1 ml 0.1M MES buffer, pH 5.3 to give a protein concentration of 0.5 mg/ml. Glucosamine dissolved in 0.1M MES buffer, pH 5.3 was added (0.25 ml) in 100 mole excess relative to the total mole amount of carboxylic acid groups present. An additional 0.25 ml containing EDC dissolved in 0.1M MES buffer, pH 5.3, was, subsequently, added to give a mole ratio of EDC to lactase carboxylic acid groups of 5:1.

The artificial glycosylation reaction proceeded for 2 hours at 25° C. under constant shaking followed by centrifugal filtration at 5000×g through a 50K MWCO membrane to remove unreacted reagent and byproducts. The filtered enzyme was reconstituted with 1 ml of 0.1M MES buffer, pH 5.5.

Non-denaturing isoelectric focusing was used to evaluate changes in the isoelectric point of lactase that occurred from the modification of ionically charged amino acid (ie $COO^-$ or $NH_3^+$). Lactase conjugates (7 µg) were added to sample buffer and loaded on pre-cast vertical isoelectric focusing gels composed of 5% polyacrylamide and 2% ampholytes with a pH gradient of 3-10. The upper chamber was filled cathode buffer (Novex) and the lower chamber filled with anode buffer (Novex) with the gel running from cathode (−) to anode (+) (ie pH 10 at the top of the gel and pH 3 at the bottom of the gel). Gels were run for 2.5 hours with the voltage step-up of 100V for 1 hour, 200V for 1 hour, and 500V for 0.5 hours. The gels were stained using a Coomassie Blue solution (45% v/v water, 45% v/v methanol, 10% v/v acetic acid, and 0.25% w/v Coomassie brilliant blue R250) for 4 hours, and destained using a solution of 50% v/v water, 40% v/v methanol, and 10% v/v acetic acid for intervals of 1 hour, then 12 hours, then 1 hour.

As noted, carboxylic acid groups of lactase were modified by conjugation of glucosamine in the presence of EDC (FIG. 12). The single amino residue of glucosamine has a low pKa value (6.91) that favors conjugation of the amine as a nucleophile via EDC—the reaction, of which, must take place at acidic to neutral pH because of the necessity for carboxylic acid to be in a deprotonated state. The glucosamine molecule, also, provides a lone point of attachment to the enzyme—preventing crosslinking. The neutrally charged hydroxyl groups of the carbohydrate, whose potential ester formation with the activated carboxylic acid would not be expected to compete with amide formation because of the low pKa of the terminal amine, would retain the hydrophilic nature of the enzyme after blocking the surface carboxylic acid groups so as not induce insolubilization or aggregation.

The amino sequence reveals that lactase (*A. oryzae*) (SEQ ID NO: 1) has 100 acid amino acid groups (aspartate and glutamate) capable of reaction with the carbodiimide (FIG. 13). The majority of available amino groups would be expected to be on the surface of the enzyme to facilitate hydrogen bonding and minimize destabilization of the hydrophobic core.

Because of the solubility of the enzyme at the isoelectric point, isoelectric focusing was employed rather than titration methods to indicate modification of the enzyme via deviation of the isoelectric point (pI) of the enzyme (the pH at which the enzyme has no net electrical charge) before and after blocking. The results showed that after the reaction of the enzyme with glucosamine, there is a substantial increase in the band surrounding the isoelectric point of the enzyme to a more basic pH (FIG. 14). This result indicates that the carboxylic groups available to contribute to the overall net charge of the enzyme have been reduced by glycosylation—leaving, predominately, basic amino groups to donate to enzyme charge and yielding a higher pI than the control.

Modification of carboxylic acids groups of lactase yielded no significant change (p<0.05) in the activity at optimum catalytic conditions or optimum conditions of pH and temperature when compared to the unmodified free enzyme (FIG. 15 and FIG. 16). Active site protection via saturation with substrate or a reversible inhibitor can be used if modification lends itself to loss of activity from conjugation of amino acids necessary for catalytic activity. *A. oryzae* (SEQ ID NO: 1) lactase; however, did not require protection of the active site during blocking of charged functional groups, under the described conditions, to retain catalytic activity—suggesting carboxylic acid groups are not present in the active site, are unavailable to react with the modifying agents under the conditions of the experiment, or are kinetically restrained. This agrees with the proposed data that the active site of lactase consists of a histidine and cysteine residue.

Example 8

This Example describes the conjugation of carboxylic acid-blocked lactase to high and low carboxylic acid polystyrene-co-acrylic acid microspheres (which was accomplished as described supra).

The results show that no significant change (p<0.05) in the amount of enzyme conjugated to the microspheres was observed for the carboxylic acid-modified lactase (high carboxylic acid-9.8±1.9 mg/g; low carboxylic acid-8.9±2.1). The specific activity of carboxylic-acid blocked lactase immobilized on high carboxylic acid functionalized polystyrene microspheres compared to the free enzyme and the unblocked immobilized enzyme can be seen in FIG. 17 and FIG. 18. Under optimum conditions, the immobilized, carboxylic acid-blocked lactase exhibited a 7-fold increase in activity compared to the unblocked, immobilized lactase. With respect to the free enzyme, a 34% mean decrease in activity occurred after immobilization of the carboxylic acid blocked lactase. A shift in optimum pH, from 4.5 for the free enzyme to 5.0 for the immobilized enzyme was observed though the change was not significantly different (p<0.05). Activity changes with pH and temperature is similar for both the free and immobilized modified-lactase with the exception of activity at 70° C. The change in molecular motion with high temperature may allow for unavailable electrostatic groups, such as those buried in the enzyme or involved in salt bridges to become available for interaction with the surface, leading to loss of structural stability.

As with the high carboxylic acid microspheres, the results show that conjugation of carboxylic acid blocked lactase to low carboxylic acid functionalized microspheres exhibited an increase in activity retention. Conjugation of the blocked enzyme did not result in a significant change (p<0.05) in enzyme activity (116Kµmol/min/g) compared to free lactase under optimum conditions (FIG. 19 and FIG. 20). These results along with the activity of modified lactase on high carboxylic acid microspheres lends evidence that lactase immobilization on carboxylic acid activated polystyrene is dependent upon protein-carrier interfacial interactions.

As the pH becomes more basic from pH 5.0, there is a significant drop in activity. With increasing pH comes an increase in deprotonation of the carboxylic acid groups of the enzyme—the pKa of amino acids in a protein being variable. Net electrostatic repulsion as well as deprotonation and repulsion of carboxylic acid chains, which were unavailable at pH 5.3 for blocking, would be expected to increase with increasing pH, introducing detrimental negative-negative interfacial electrostatic interaction—yielding activity values that are not significantly different from that of the modified enzyme on high carboxylic acid at the same corresponding pH. The temperature profile of the immobilized modified-enzyme was shifted compared to the free enzyme (FIG. 19). At 70° C., there is a significant loss in activity (p<0.05) for the immobilized modified-enzyme compared to the free enzyme. As described for the high carboxylic acid, higher temperature promotes enhanced molecular motion and, subsequent, structural confirmation sampling and interaction with, not only the aqueous medium, but also the carrier, which seems to promote loss of activity.

These results provide further evidence that inactivation of the enzyme after conjugation to carboxylic acid functionalized polystyrene microspheres is due to negative-negative interfacial charge repulsion between the carrier and enzyme and not multipoint binding, since the same quantity of amine groups on the enzyme are free to react with the carrier before and after blocking of the carboxylic acids on the enzyme. The repulsion of the enzyme from the surface may be localized from charge amino groups or result from net charge above the isoelectric point of the enzyme. Literature results regarding conjugation of lactase on negatively charged surface appears conflicting. The activity of bacterial (E. coli) lactase was shown to be substantially inhibited on a polyanionic structure compared to an anionic surface. Contrary, the activity of lactase adsorbed to sulfate dextran-modified MANAE-agarose was reported to be 100%; however, the activity appears to result from activity measurements taken after desorption of the enzyme from the carrier. If activity is inhibited on the surface but not after desorption (ie the protein is distorted on the surface but recovers in solution), ionic supports may be used for separation of the protein without concerns of denaturation. Blocking the carboxylic acid groups of lactase, by changing the pI of the enzyme and retaining enzyme activity, may have application for, not only covalently bound enzyme, but also recycling of enzyme on ionic supports.

Example 9

This Example describes the evaluation of the stability of the immobilized lactase (from A. oryzae) (SEQ ID NO: 1), as described supra. The activity of the carboxylic-acid blocked lactase and unmodified lactase (control) on carboxylic acid microspheres was monitored across a 4-week period to evaluate long-term stability of the conjugates at potential processing storage conditions (FIG. 21). The stability of immobilized lactase preparations (A. oryzae) (SEQ ID NO: 1) were evaluated by storing the samples in 0.1M MES buffer at 4° C., pH 5.5; 4° C., pH 6.8; 25° C., pH 5.5; and 25° C., pH 6.8. Specific activity was accessed every two weeks over an 8 week period.

The results show that across the evaluation period, no significant changes (p<0.05) were observed at the respective pH and temperature storage conditions, indicating that that conjugates are stable and changes in activity as a function of conjugation occur prior to activity measurement.

Example 10

This Example describes carbodiimide modification of lactase for conjugation to polystyrene-co-acrylic acid microspheres. Carbodiimide addition to lactase in the absence of glucosamine was investigated to explore the possibility of non-specific inter and intramolecular crosslinking reactions that may occur when using the reagent in solution. Molecular crosslinking has been shown to occur when using EDC with proteins because of the ability of the carbodiimide to react with protein carboxylic acid groups with available amine groups present on the protein. Activity was assessed for lactase after incubation with EDC at 0, 0.5, 5, and 50 molar excess with respect to the moles of carboxylic acid groups associated with the enzyme.

The effect of carbodiimide on the free and immobilize stability of lactase was evaluated using 1-ethyl-3-(3-dimethylaminopropyl)carbodiimide (EDC). Purified lactase was added to 1 ml 0.1M MES buffer, pH 5.3 to give a protein concentration of 0.5 mg/ml. An additional 0.5 ml containing carbodiimide dissolved in 0.1M MES buffer, pH 5.3, was, subsequently, added to give the following mole ratio of EDC to lactase carboxylic acid groups: 0:1, 0.05:1, 0.5:1, 5:1, and 50:1.

The reaction proceeded for 2 hours at 25° C. under constant shaking followed by centrifugal filtration at 5000×g through a 50K MWCO membrane to remove unreacted reagent and byproducts. The filtered enzyme was reconstituted with 1 ml of 0.1M MES buffer, pH 5.5.

As can be seen from (FIG. 22 and FIG. 23), the results show that there is a lowering in the activity of lactase after incubation with 50 molar excess EDC—suggesting modification of the enzyme. Decrease in activity after the addition of high concentrations of carbodiimide to lactase has been observed, previously, though details for the loss of activity were not described.

Example 11

This Example describes the use of SDS PAGE, as described previously, to determine the extent of intermolecular crosslinking associated with carbodiimide modification, as described in Example 10. The number of primary amino groups (ie lysine and N-terminus) on lactase modified by modification was determined based on methods described by Habeeb and Mokrasch. Lactase conjugates were diluted in distilled water to a protein concentration of 0.2-0.6 mg/ml as determined by the previously reported Bradford method. To separate tubes containing 1.95 ml of 0.1M borate buffer (pH 9.6) was added 50 µl of the respective diluted enzyme solutions. Picrylsulfonic acid (2,4,6 trinitrobenzenesulfonic acid (TNBS)). A 5% w/v TNBS solution was made in deionized water and diluted to a 0.03M concentration by the addition of 0.3 ml of the TNBS solution to 1.4 ml of distilled water to bring the total volume to 1.7 ml. The 0.03M TNBS was made daily when determining the degree of modification. To the tubes containing 50 µl of diluted enzymes in 0.1M borate buffer was added 20 µl of 0.03M TNBS. The tubes were vortexed and incubated in the dark at 24° C. for two hours. Upon completion of the incubation period, the solutions were placed in cuvettes and the absorbance read in a spectrophotometer at 420 nm and compared to a standard curve. The standard curve was created using glycine which was diluted in distilled water to a concentration of 0.266 mM. The diluted glycine was added to individual glass tubes in amounts of 0, 25 µl, 75 µl, 125 µl, 175 µl, 225 µl, and 275 µl, and enough 0.1M borate buffer (pH 9.6) was added to bring the total volume to 2 ml. The standards were treated with TNBS as described for the enzyme samples. A regression equation was derived from the standard curve of absorbance versus moles of free amino assuming a 1:1 relationship of moles of free amino group to mole of glycine, as well as a 1:1 relationship of TNBS to mole of glycine. The moles of free amino groups of lactase conjugates were extrapolated from the regression equation and expressed as a function of the quantity of protein. The degree of modification of lactase was determined by dividing the moles of free amino groups per milligram of modified-lactase by the moles of free amino groups per milligram lactase, subtracting the product from one, and multiplying the solution by 100 to obtain a percent of amino group modification. Samples were done in triplicate. Thiol concentration was determined using Ellman's reagent. A standard curve was prepared using cysteine. 250 µl of a 0-1.5 mM solution of cysteine in 0.1M phosphate buffer, pH 8.0 was added to glass tubes containing 50 µl of Ellman's reagent and 2.5 ml of 0.1M phosphate buffer, pH 8.0 giving solutions containing 0 to $3.75 \times 10^{-7}$ moles of free thiol groups. The unmodified and modified lactase solutions were added to glass tubes containing 50 µl of Ellman's reagent and 2.5 ml of 0.1M phosphate buffer, pH 8.0 giving solutions containing 3 mg of enzyme. Samples were incubated at room temperature for 15 minutes and the resulting absorbance read at 412 nm. Free thiol groups were calculated using the standard curve and dilution procedure.

Isoelectric focusing, as described previously, was employed to detect carboxyl group modification of the enzyme.

Modified-lactase specific activity for the free enzyme was determined as described previously with protein concentration being determined by the Bradford method.

The results show that SDS-PAGE of the enzyme preps after incubation with EDC reveals all preps to be monomers of the same molecular weight—indicating that EDC does not promote intermolecular crosslinking of lactase (FIG. 24). Likewise, evidence of intramolecular crosslinking was pursued by determining the availability of amine and thiol groups. If intramolecular crosslinking occurs during incubation, free amines and thiols would be expected to react and fewer of those groups would be available for detection. TNBS and Ellman's reagent, used for detecting free amines and thiols, respectively, showed no significant difference (p<0.05) between the quantity of available amine and thiol groups associated with the enzyme incubated without EDC and those incubated with EDC, suggesting that intramolecular crosslinking does not occur, is at a level below assay detection limits, or reacts with other amino acids such as tyrosine.

Lactase preps modified with the indicated molar excess of EDC were immobilized on high and low carboxylic acid polystyrene-co-acrylic acid microspheres. Loading on the microspheres was not significantly (p<0.05) different across incubation levels. When immobilized to high carboxylic acid polystyrene-co-acrylic acid microspheres, there was no significant (p<0.05) difference in lactase activity associated with EDC incubation until 5 molar excess (relative to the moles of carboxylic acid groups of lactase) of EDC was used. For 5 molar excess, a significant increase (p<0.05) in activity was observed with a 50% mean activity retention compared to the same free enzyme prep under optimum conditions (FIG. 25 and FIG. 26). Enzyme prep incubated at 50 molar excess had a greater increase in activity—yielding an 83% mean activity retention compared to the same free enzyme prep under optimum conditions.

Immobilization of lactase to low carboxylic acid polystyrene-co-acrylic acid microspheres displayed a similar trend, with significant activity increases corresponding to 5 and 50 molar excess EDC incubation (FIG. 19 and FIG. 20). The peak total specific activity of the immobilized enzyme corresponded to the 5 molar excess prep (111Kµmol/min/g of lactase) on the low carboxylic acid polystyrene co-acrylic acid microspheres. The activity accounted for 89% mean activity retention under optimum conditions. The highest activity retention was obtained with the 50 molar excess—having 92% mean activity retention compared to the corresponding 50 molar excess free lactase prep. This immobilized enzyme had lower total activity, though, because of the decrease in activity of the free enzyme after incubation with 50 molar excess EDC.

The enzyme preps incubated with a high mole excess of EDC (5 and 50 molar excess), when immobilized, display characteristics similar to that of carboxylic acid blocked lactase. To determine if carboxylic acid groups of the enzyme were modified, isoelectric focusing of lactase after incubation with 50 molar excess EDC was performed. IEF gel revealed an isoelectric range corresponding to that of carboxylic acid blocked lactase suggesting carboxlic acid groups of lactase had been modified (FIG. 24).

Excess carbodiimide, relative to mole quantity of carboxylic acids, can form stable N-acylurea products in the absence of amines—noting that no change in carboxylic groups (ie N-acylurea formation) occurred at less than molar excess quantities because of hydrolysis of the carbodiimide activated carboxylic acid groups back to free carboxylic acid (FIG. 30). A stable N-acylurea product being formed when EDC is in excess of lactase carboxylic acid groups (ie blocking of the carboxylic acid groups) corresponds with isoelectric focusing and immobilized stability results. The results suggest that under assay conditions, N-acylurea formation from reaction of excess EDC with carbodiimide activated carboxylic acid groups of lactase can occur without the formation of intra and intermolecular crosslinks. This data verifies the negative-negative electrostatic effect between the enzyme and carrier, and suggest that, for *A. oryzae* (SEQ ID NO: 1) lactase, a "one pot" attachment to a reactive amine surface may be used without concern for intra and intermolecular crosslinking or carboxylic group modification of the free enzyme, provided EDC is not used in excess.

Example 12

This Example describes the tethering if chitosan to the polystyrene-co-acrylic acid microspheres.

Loss of enzyme activity after attaching lactase to carboxylic-acid activated polystyrene-co-acrylic acid microspheres and low protein loading (<10 mg of enzyme/g of microspheres) on such supports are limitations to application of these lactase-immobilized systems. Investigations were made into the covalent immobilization of lactase to polystyrene-co-acrylic acid microspheres via a chitosan-tethered intermediate using carbodiimide-mediated chemistry, given that:

1. loss of enzyme activity on polystyrene-co-acrylic acid microspheres can be attributed to electrostatic interactions between carboxylic acid groups on the enzyme and carrier surface;

2. glucosamine can be conjugated to lactase carboxylic acid groups without a significant loss of activity;

3. polymers, tethered to a solid support, have been shown to increase surface loading on a carrier;

4. lactase (*A. oryzae*) (SEQ ID NO: 1) has been shown to retain activity when conjugated to chitosan—an FDA approved natural polymer composed of repeating glucosamine monomer units; and 5. carbodiimide chemistry can be used to conjugate lactase to glucosamine without concern of intra or intermolecular crosslinking.

Chitosan was tethered to polystyrene-co-acrylic acid microspheres by carbodiimide coupling. The chitosan solution was obtained by the dissolution of 50 mg of low molecular weight chitosan (Sigma) in 10 ml of a 0.03M solution of HCl followed by stiffing for 15 minutes. When the chitosan had dissolved completely, 10 ml of 0.1M MES buffer, pH 5.8, was added, adjusting the final pH to 5.3 and giving a chitosan solution of 2.5 mg/ml. The chitosan solution (1 ml) was added to 0.5 ml of 0.1M MES buffer pH 5.3 containing 0.006 g of clean PS-AA, high carboxyl, microspheres and mixed. Carbodiimide (EDC) was introduced at a 10 mole excess (0.0016 g) relative to the mole amount of carboxyl groups present on the microspheres. The reaction was held at 25° C. for 2 hours. Free chitosan and residual EDC was removed by centrifugation using a 5× rinse of 0.1M acetic acid buffer, pH 4.0.

As noted, chitosan was covalently grafted to high carboxylic acid polystyrene-co-acrylic acid microspheres using EDC—linking the amine groups of chitosan to the carboxylic acid groups of the microspheres and leaving free amine groups on the surface for further conjugation (as shown in FIG. 31).

The pKa of the amino groups of chitosan (pH 6.5), as with glucosamine, promotes reactivity (i.e. deprotonation of the amine to induce nucelophilic attack under the conditions of the assay) of the aminated polymer with carboxylic acid groups in the presence of EDC. Here, too, ester formation associated with hydroxyl groups of the polymer would not be expected to compete because of dominate reactivity of the amine groups. Though acetic acid is most often used to dissolve chitosan, diluted hydrochloric acid was employed to prevent non-specific reaction with EDC.

The extent of chitosan tethering was determined using the Toluidene Blue assay and the Acid Orange 7 assay. The Toluidiene Blue assay was used to follow the loss of carboxylic acid groups on the surface and was performed as described previously. The Acid Orange 7 assay was used to characterize the appearance of amine groups associated with chitosan (Uchida et al, 1993). Microspheres were immersed in 1 ml of a $1 \times 10^{-3}$ M Acid Orange 7 solution in distilled water that had been adjusted to pH 3 by HCl. After 3 hours of shaking at room temperature, the microspheres were rinsed with distilled water at pH 3 to remove non-complexed dye and collected by centrifugation. Complexed dye was, then, desorbed by shaking microspheres in water, adjusted to pH 12 by NaOH, for 15 minutes at room temperature, followed by centrifugation and removal of the desorbed dye into a cuvette. Absorbance of the desorbed dye was read at 460 nm and compared to a standard curve of dye with the assumption that one mole of dye complexes with one mole of available amine groups and knowing the volume of the desorbing solution (pH 12 NaOH).

The results show evidence of chitosan attachment, as seen in FIG. 32, by the change in carboxyl and amino groups using dye adsorption. There is a significant increase (p<0.05) in the surface amines ($131 \pm 59$ nmol/cm$^2$ to $54928 \pm 6740$ nmol/cm$^2$) and decrease in carboxylic groups ($97816 \pm 4228$ nmol/cm$^2$ to $26774 \pm 1629$ nmol/cm$^2$) upon conjugation of chitosan. Coverage of surface carboxylic acid groups on the microspheres was incomplete, which can be attributed to steric hindrance of the polymer chains during conjugation or amine accessibility to available carboxylic acid groups.

Example 13

This Example describes zeta potential testing that was utilized to determine the electrokinetic potential of the supports at lactase conjugation pH (5.3). Though not a measure surface charge, zeta potential does reflect the nature of the particle surface by determining the potential between the medium and stationary layer attached to the microspheres.

Microspheres in 0.1M acetate buffer (pH 5.3) were diluted to low concentrations (~0.0033 µg/ml) in ultra pure water with a final pH of 5.3. A Brookhaven 90Plus Nanoparticle Size Analyzer (Brookhaven Instruments Corp., Holtsville, N.Y.) was fitted with the ZetaPlus option, and measurements were performed in the High Precision mode at 20° C. and setting "water" as solvent. The measurement consisted of 30 cycles/run, with an intercycle delay of 5 seconds. Protein dilutions were adjusted in order to achieve the recommended instrument count rate of 300-350 kcps.

The results show that the analysis verified conjugation of chitosan (see FIG. 33 and FIG. 34). Zeta potential increased from −42 mV for the carboxylated microspheres to 4 mV for the chitosan-tethered microspheres at pH 5.3. As amines are introduced to the surface and carboxylic acid groups are blocked, the charge increases. As can be seen from FIG. 33, the analysis also revealed that, at pH 5.3, the zeta potential of the chitosan-tethered molecules is approaching zero—indicative of the isoelectric point of the carrier system. The potential is reflective of not only the available carboxylic acid and amine groups being present but also the isoelectric points of the carboxylic acid and amine molecules. Stability of colloids, with respect to zeta potential, increases as the potential moves away from zero in the positive or negative direction. This result is significant in that it suggests pH conditions used for lactase conjugation to the chitosan-tethered supports promotes flocculation of the support. This measurement; however, may be skewed given that the microspheres would be settling under gravity during the assay (i.e. moving out of the field of measurement), which may alter the absolute value of the corresponding zeta potential.

Example 14

This Example describes the analysis of the high carboxylic acid polystyrene-co-acrylic acid microspheres and the chitosan tethered, high carboxylic acid polystyrene-co-acrylic acid microspheres.

Microspheres were dried on a glass microscope slide. Analysis was performed at the Cornell Nanofabrication Facility. The particles were sputter coated with Au/Pd in a Hummer V(Technics) sputtercoater. Images were produced using a scanning electron microscope (Zeiss Ultra) with SE1/InLensdetector.

The results show that though the microspheres appeared suspended in the solution to the naked eye, the flocculation phenomenon was observed by scanning electron micrographs (FIG. 35 and FIG. 36). Aggregation appears to be between chitosan chains suggesting surface interaction as the pH of the system (5.3) is nearing the isoelectric point of chitosan (6.5). Association is evident for solubilized chitosan in solution as it moves from acidic to neutral and basic conditions.

Example 15

This Example describes the immobilization of lactase to the polystyrene-co-acrylic acid microspheres via the tethered chitosan intermediate (described in the previous Examples).

Lactase was covalently immobilized onto chitosan-tethered polystyrene-co-acrylic acid microspheres through formation of a peptide bond. A 1.5 ml increment of lactase (*A. oryzae*) (SEQ ID NO: 1) in 0.1M MES buffer, pH 7.0 or 5.3 was added to chitosan-tethered microspheres in the presence of a EDC at a 0.9:1 mole ratio of EDC to enzyme carboxylic acid groups (total glutamic and aspartic acid). The reaction proceeded for 1 hour at 25° C. under constant horizontal shaking. Enzyme that had not been immobilized was separated by centrifugation as described, previously, for excess reagent until no further protein was detected in the supernatant as determined by addition of 0.5 ml of the supernatant to 3 ml of Bradford reagent and compared to the control containing no enzyme.

As noted, lactase (*A. oryzae*) (SEQ ID NO: 1) was conjugated to the chitosan-tethered microspheres via the addition of EDC in a 0.9:1 molar ratio of EDC to carboxylic acid groups to alleviate concerns of carboxylic blocking from N-acylurea formation. The reaction scheme for lactase conjugation to chitosan-tethered supports is shown in FIG. 31.

The results show that conjugation of lactase (500 mg of lactase offered per gram of carrier) to chitosan-tethered microspheres resulted in a significantly higher ($p<0.05$) protein loading compared to loading on microspheres without a chitosan-tethered intermediate (FIG. 37). The increase in loading can be explained by the available surface area associated with the microspheres being enhanced with chitosan tethering and resulting polymer brushing/extension from the carrier surface, or physical/chemical interactions of the enzyme with the surface that promotes loading. Though no intermolecular crosslinking was observed with the addition of EDC to free lactase, changing the surface microenvironment may drive the protein to the surface, promoting enzyme interaction, aggregation, and crosslinking and increased protein loading. A similar phenomenon is observed in the formation of crosslinked enzyme aggregates (CLEAs).

The effect of offered enzyme (i.e. free enzyme available in solution) on chitosan-tethered microspheres protein loading and specific activity was investigated to determine the optimal condition for conjugation. Protein was offered from a theoretical value of 5 mg/g to 500 mg/g. At low protein concentrations (ie 5 mg/g), the enzyme taken-up approaches 100% (FIG. 38). Beyond the offered 100 mg/g, activity decreases, as well as the rate of loading. Loss of activity with increased loading has been observed on other supports and has been attributed to crowding of the enzyme at the surface which leads to spatial restrictions, limited active site accessibility, or denaturing of the protein. The loading was fitted by nonlinear regression using a one site total binding model (Graphpad Prism software) (FIG. 39). The equation fitting the model is described in Equation 7:

$$Y = B\text{max} * X/(Kd+X) + NS * X + \text{Background} \qquad \text{Equation 7}$$

Where: Bmax is the maximum specific binding in the same units as Y, Kd is the protein offered needed to achieve a half-maximum binding at equilibrium (same units as X), NS is the slope of nonspecific binding in Y units divided by X units.

$$\text{Giving: } Y = 16.7 * X/(17.14+X) + 0.0085 * X + 0.393$$

Comparing the model with FIG. 37, lactase binds specifically (i.e., in a noncrowded fashion) until reaching a loading of 16.7 mg/ml ($B_{max}$). Beyond the $B_{max}$, the protein associates in a nonspecific way (i.e., crowded). This explanation appears to correlates well with the specific activity of the enzyme under the noncrowded/crowded conditions. The curve may also be described as a Langmuir adsorption isotherm—suggest that, as more enzyme is offered, the fraction of available binding sites decreases until the fixed number of sites are covered.

The specific activity of lactase on chitosan-tethered microspheres was not significantly different ($p<0.05$) compared to the free enzyme under optimum conditions (FIG. 40 and FIG. 41). Optimum pH was shifted to a more acidic condition upon conjugation of the enzyme to the chitosan-tethered support, most likely due to the microenvironmental effects associated with protonated amines near the support surface which results in a more basic localized pH and apparent optimal pH shift associated with the bulk. The effect of pH and temperature on lactase activity indicates that increasing temperature and decreasing pH causes the conjugated lactase to behave more like the free enzyme. This result would be expected if mass transfer limitations exist when moving from extended, solubilized chitosan polymers and high molecular interaction at low pH and high temperature to collapsing, insoluble chitosan (deprotonated amines) and low molecular interactions at increasing pH and decreasing temperature. Though surface carboxylic acid groups are still available after tethering of chitosan (at levels greater than low carboxylic acid polystyrene-co-acrylic acid microspheres), the negative protein-surface interactions, as determined from specific activity, do not seem to occur. Both spacing between the protein and surface accompanying the chitosan tether, and preferential interaction between the negatively net charged enzyme and positively charged polyglucosamine surface may prevent these negative associations. Both of these explanations are in agreement with previous work. These results indicate that a chitosan-tethered surface can promote loading and stability of lactase on carboxylic acid activated supports. Though the system may serve as an alternative to blocking of the enzyme for conjugation to the carboxylic acid activated supports, flocculation of the carrier may present a limitation to the use of the system for some applications that require high dispersability of the support under low mixing force.

Example 16

The next several Examples describe the immobilization of lactase on low density poly(ethylene) films.

A package that is able to reduce lactose is an area of interest in new product development for dairy applications. Potential markets exist for lactose reduced products though advancements into these markets are limited for small producers because of capital investment and technical input. Employing the package itself as a reactor could produce lactose-reduced fluid milk that is independent of processing variability—requiring only a packaging change at the end of the production line that, during shipping, would produce a lactose-reduced product (FIG. 42).

Low density poly(ethylene) and poly(ethylene vinyl acetate) make attractive carrier foundations for lactose-reducing films because of the low cost of materials and the inherent use of the films as heat seal layers in such packages—assuring contact of the innermost film surface with the product. Immobilization of proteins to these films; however, is limited because of the physical nature of the polymer, processing conditions that are not amendable to enzyme entrapment, and the inert surface of the films which restricts covalent conjugation chemistries. Oxidation of the surface of the film by plasma oxidation and wet chemical methods has proven to be an effective means of creating functional groups of the surface of the material. Previous attempts have been made to immobilize lactase to carboxylic acid-activated poly(ethylene) for producing a lactose-reducing film and entrapped within poly(ethylene vinyl acetate) films. These methods; however, retain little or no intrinsic enzyme activity. With the knowledge that microenvironmental influences, when conjugated carboxylic-activated hydrophobic microspheres, can be minimized and lactase activity preserved by blocking enzyme carboxylic acid groups, investigations were made into extending this approach to the immobilization of lactase on carboxylic acid activated low density poly(ethylene) packaging films.

Example 17

This Example describes the activation of low density poly (ethylene) (LDPE) films using chromic acid to oxidize the surface of the film and generate carboxylic acid groups. In a first step, Additive-Free Low Density Polyethylene (LDPE) films (6401, Dow Chemical Company, 100 um) were cut in 2×2 $cm^2$ pieces and cleaned by the 3-step process described by Goddard. Films were sonicated 3 times in dichloromethane for 10 minute intervals, followed by identical treatments in acetone and, then, deionized water.

The polyethylene films were then functionalized by chemical oxidation using a chromic acid solution. A weight percent ratio solution of 29:42:29 $CrO_3$:$H_2O$:$H_2SO_4$ was prepared and distributed to glass vials held in a heating block at 70° C. Cleaned PE films were individually submerged in 15 ml of the chromic acid solution and held at 70° C. for two minutes then rinsed 3 times in deionized water. The rinsed, oxidized films were submerged in 70% nitric oxide for 15 minutes at 50° C. to dissolve any chromium salts present on the film, and subjected to triplicate rinse in deionized water prior to storage in deionized water until further use.

XPS (X-ray photoelectron spectroscopy) analysis of the functionalized polyethylene films was conducted at the Penn State Materials Characterization Laboratory (State College, Pa., U.S.A.) on a Kratos Analytical Axis Ultra (Kratos Anaytical, Inc, Chestnut Ridge, Ny, U.S.A.) with a monochromatic Alka X-ray source at an X-ray power of 280 W, a 90° takeoff angle, and a spot size of 700×300 p.m.

The X-ray photoelectron spectroscopy verified the presence of oxidative products as indicated by the presence of oxygen in the surface elemental analysis (FIG. 43).

Contact angle measurements were used to provide evidence of film modification. Films were mounted on glass microscope slides using double-sided tape for use with a Tantec contact angle meter. A single drop of reagent grade deionized water (pH 7.0) was syringe fed until it was in contact with the film. The resulting angle taken from the origin through the height of the droplet and its half-width was determined in triplicate and labeled as the contact angle of the film.

The contact angle measurement provided qualitative evidence for surface activation (FIG. 44). Oxidation of the methyl groups on the surface of the film lowers the surface energy, yielding a more hydrophilic interface and lower surface contact angle. As seen in FIG. 44, oxidation of LDPE films reduces the water contact angle of the surface from a mean 99° to 52°—verifying surface modification of the film.

Oxidation of the LDPE surface to produce carboxylic acids was quantified using Toluidine Blue O dye adsorption/desorption with the charged surface. Available carboxylic groups on the surface of the microspheres were quantified using the Toluidine Blue assay (Kang et al, 1996). Films (2×2 $cm^2$) were immersed in 10 ml of 5×$10^{-4}$M Toluidine Blue O in distilled water that had been adjusted to pH 10 by NaOH. After three hours of shaking at room temperature, the films were rinsed three times with NaOH solution at pH 10 to remove non-complexed dye. Complexed dye was then desorbed by shaking films three times in 5 ml, 50% v/v acetic acid for 15 minutes at room temperature, and the absorbance of the desorbed dye was read at 633 nm, and surface carboxyl groups were determined by comparison with a standard curve of dye, knowing the quantity of microspheres and the volume of the desorbing solution under the assumption of one mole of dye complexing with one mole of available carboxyl groups (Uchida et al, 1993).

As seen in FIG. 45, the results show that there was a significant increase ($p<0.05$) in the carboxylic acid on the surface of the film, resulting in 2.4 (±0.32) nmol of carboxylic acid groups/$cm^2$ of film. The amount of carboxylic acid groups indicates more than a monolayer of surface carboxylic groups—indicating etching of the surface.

Example 18

This Example describes the conjugation of lactase and carboxylic-acid blocked lactase (*A. oryzae*) (SEQ ID NO: 1) to carboxylic acid-activated LDPE films using carbodiimide chemistry. Unmodified and glucosamine-modified lactase (*A oryzae*) (SEQ ID NO: 1) were immobilized to oxidized films by a two-step process. Oxidized PE films were added to 100 ml of 0.1M MES buffer, pH 5.3 under continuous stirring to keep the films submerged. 1-ethyl-3-(3-dimethylaminopropyl)carbodiimide (EDC) was added in a 10 mole excess and N-hydroxysuccinimide (NHS) was added in a 100 mole excess relative to number of carboxyl group present on the film. The reaction was allowed to proceed for 1 hour at room temperature. The resulting films, with an activated NHS-ester group, were rinsed in deionized water and placed in a 100 ml of a 0.1M MES buffer (pH 7.0) containing 5 mg of either the modified or unmodified lactase. The reaction occurred for two hours at room temperature. Films were, subsequently, rinsed three times in 0.1M MES buffer (pH 5.5) and stored in the same buffer at 4° C. until further use.

Protein concentration was determined using the BCA films described previously. One 2×2 $cm^2$ film was added to 2 ml of the BCA solution and kept at 60° C. for 30 minutes. The film was removed and the absorbance at 562 nm was read and compared to a control film with no immobilized lactase. Protein concentration per $cm^2$ of film was determined by dividing the protein concentration on the 2×2 $cm^2$ film by eight since lactase was immobilized on both sides of the film. Covalent immobilization was distinguished from ionic adsorption through the use of SDS as described, supra.

The results show that protein loading on the carboxylic acid-activated surface (0.67±1.7 μg/$cm^2$) was higher than a monolayer verifying etching of the surface.

The specific activity of unmodified or glucosamine-modified lactase, immobilized on oxidized PE films, was determined using a modification of the FCC method for free enzyme activity. One film was added to 10 ml of a 0.012 mM solution of the synthetic lactose substrate, o-nitrophenyl-β-galactopyranoside, and allowed to react under shaking for 15 minutes. At the completion of the time period, 2 ml of the solution was pipetted into 2.5 ml of 10% sodium carbonate to stop the reaction. The solution was diluted to 25 ml with deionized water and the absorbance of 2 ml of the diluted sample was read at 420 nm (Jenway 6300 spectrophotometer). Specific activity was determined using equation 4. Temperature and pH effects were evaluated in the range described for the free enzyme. The Michaelis constant was determined by transferring a single 2×2 $cm^2$ film to preheated tubes (under shaking) at each time point (30 second intervals) in a given substrate concentration (0-8 mM). Upon completion of each time increment, the film was transferred to the tube representing the proceeding time increment, while the preceding was, simultaneously, stopped by the addition to 10% sodium carbonate. Separate films were used for each substrate concentration and $K_m$ was determined from Equation 5.

The results show that the specific activity of lactase-immobilized LDPE films was accessed as a function of pH and temperature (FIG. 46 and FIG. 47).

The results also show that unmodified lactase on oxidized LDPE films demonstrated no measurable specific activity under conditions of low mass transfer limitations (ie high stirring and excessive bulk substrate concentration). The activity of the enzyme on oxidized polyethylene films is dependent upon the surface of the enzyme and the surface of the film. Blocking the carboxylic acid groups of lactase with glucosamine, as with conjugated polystyrene-co-acrylic acid microspheres, aided in the retention of activity when the enzyme was conjugated to carboxylic acid-activated LDPE—indicating that electrostatic interactions between the carboxylic groups of the oxidized surface and enzyme influences structural and activity stability. For a typical one liter package, immobilization-lactase, under optimum conditions (and assuming unaltered kinetics when interchanging lactose for ONPG), would take 24 days to reduce lactose in the package by 70%.

Assuming microenvironmental influences were managed, as demonstrated on carboxylic-acid activated microspheres, the dramatic loss of activity must be explained by additional variables. The regularity of a surface as well as the curvature of a carrier as it relates to protein-protein lateral interaction, have been shown to contribute to enzyme activity. Michaelis-Menton kinetics, and, subsequently, an enzyme's intrinsic activity, applies to systems that succumb to Brownian motion and are freely allowed to randomly move and collide with substrate molecules and visa versa. The apparent activity of "immobilized" enzymes, when mass transfer limitations are removed (i.e. system is under high stirring), bulk substrate concentration is much greater than enzyme concentration, there are no electrostatic interactions driving substrate interaction, and the intrinsic activity of an enzyme is unchanged upon conjugation, may be owed to the mobility of the carrier (and the enzyme). The Stokes-Einstein equation, which is used to describe molecules in solutions, has been shown to apply to larger particles—including microspheres. Kinetic parameters are only slightly changed between free alpha-chymotrypsin and the enzyme immobilized to polystyrene nanoparticles with diameters between 110-1000 nm. The nanoparticle biocatalysts behaved according to the Stokes-Einstein equation and collision theory. However, when the enzyme was attached to a thin film (free from mass transfer effects) and the Stokes-Einstein equation no longer held, the activity was 1% of the enzyme activity when attached to the 1000 nm particles. The authors believed the change in activity was due to hindered mobility of the enzyme. If this is the case, then not only microenvironment but also mobility/size of the carrier will influence conjugated enzyme activity, which may hinder active packaging applications. As indicated before, the system was conducted under high stirring—limiting mass transfer limitations. The Michaelis constant ($K_m$) of the immobilized system was evaluated to determine if substrate accessibility influenced perceived activity. A significant increase in $K_m$ was observed when immobilized to the polyethylene films (2.05±0.28 mM vs 0.83±0.22 mM). Though an increase in Michaelis constant was observed, and can be attributed to the mobility of the carrier as described, previously, the $K_m$ was below the substrate concentration used to determine specific activity (12 mM). Because the activity, under the conditions of the assay, is not influenced the substrate concentration of the system, loss of activity must be attributed to alternative factors such as surface morphology caused by etching, surface irregularity, dehydration near the film surface, or oxidative byproducts (ie hydroxyl or aldehyde) groups interacting with the enzyme.

According to the Examples set forth, supra, embodiments of the present invention have demonstrated the following: Lactase (*A. oryzae*) (SEQ ID NO: 1) can be covalently bound to carboxylic acid, hydrophobic supports by "zero length" carbodiimide-mediated chemistry; the loss of lactase activity when conjugated to polystyrene-co-acrylic acid microspheres is, predominately, a protein-carrier, surface-surface phenomenon and dependent upon the interfacial density of surface carboxylic acid groups on the support; increasing the density of surface carboxylic acid from 87 $Å^2$ between surface carboxylic acid groups to 6.2 $Å^2$ between surface carboxylic acid groups results in a 67% and 89% decrease, respectively, in enzymatic specific activity relative to free lactase under optimum conditions; blocking carboxylic acid groups of lactase with glucosamine ("carboxylic acid blocked-lactase") does not significantly alter specific enzyme activity on a per protein basis, conjugation of carboxylic acid-blocked lactase to polystyrene-co-acrylic acid microspheres significantly increases enzymatic activity compared to the conjugated enzyme that was not blocked without significantly effecting the amount of enzyme loaded on the carrier; negative surface-negative surface enzyme-carrier electrostatic interfacial interactions are responsible for loss of enzyme activity upon conjugation; the addition of excess carbodiimide (EDC), relative to enzyme carboxylic acid groups and in the absence of a nucleophile, results in blocking of enzyme carboxylic acid groups by N-acylurea formation; on a per protein basis, modification of enzyme carboxylic acid groups with excess EDC prior to attachment yields a significant decrease in free enzyme activity, but a significant increase in enzymatic activity upon conjugation to polystyrene-co-acrylic acid microspheres—verifying negative surface-negative surface enzyme-carrier electrostatic interfacial interactions are responsible for loss of enzyme activity upon conjugation; chitosan can be tethered to polystyrene-co-acrylic acid microspheres with amine groups available for the attachment of lactase; on a per protein basis and under optimum conditions, attachment of lactase to chitosan-tethered polystyrene-co-acrylic acid microspheres yields no significant change in specific activity compared to the free lactase, blocking enzyme carboxylic acid groups with glucosamine prior to covalent immobilization of lactase to oxidized low density polyethylene yields an active packaging film with lactase activity.

Example 19

This Example describes the covalent attachment of chitosan to polystyrene/acrylic acid microspheres. Chitosan, dissolved in 0.001M HCl is added to cleaned polystyrene/acrylic acid microspheres (1 μm diameter) in pH 5.5 buffer. The carbodiimide, 1-ethyl-3-(3-dimethylaminopropyl)carbodiimide (EDC) is added to the solution, mixed, allowed to proceed for two hours—leading to the covalent attachment of the amino groups of chitosan to the carboxyl groups of the PS/AA microspheres Upon completion of the reaction time, the modified microspheres are separated from the reactants by centrifuging and the supernatant is removed.

Example 20

This Example describes the immobilization of lactase to the modified microspheres as described in Example 19. Commercial lactase from *Aspergillus oryzae*, purified using syringe filtration and ultrafiltration, is added, along with EDC, to the cleaned chitosan-PS microspheres (pH 5.5). The reaction is allowed to proceed for two hours, yielding a product in which the free amino groups of chitosan are attached to the carboxyl groups of lactase by a amide bond formation. The lactase-immobilized spheres are separated from unreacted lactase by centrifugation, as described supra (see FIG. 48, showing the immobilization of lactase onto a polystyrene/acrylic acid support using a chitosan intermediate).

The results show that the microspheres contain 50-60 mg of covalently bound lactase/g of microsphere with a maximum activity of 3600 μmol/min per gram of microsphere when using the synthetic substrate o-nitrophenyl-β-galactopyranoside as a substrate (55° C., pH 5.0). At 70° C. the bound enzyme retained 22% of its maximum activity while the soluble enzyme retains 7%, indicating that the thermal stability is increased upon attachment to the support.

This Example demonstrates the advantages of an embodiment of the present invention that provides a hydrophobic core composed of a polystyrene/acrylic acid copolymer and a covalently grafted hydrophilic layer composed of chitosan, as discussed in the Summary of the Invention section, supra. This Example also demonstrates that the size and solubility of the microspheres enables the enzyme to be recovered and reused; optimal lactose reduction can be achieved at about 55° C. to decrease microbial growth; lactase can be covalently attached under weakly acidic pH conditions that can provide optimal stability for the enzyme; the conjugate can be achieved in a two step process, totaling about four hours; under optimal conditions, 70% of the soluble enzyme activity can be maintained after conjugation; and stability of the conjugate, relative to the soluble enzyme, can be increased at higher temperatures.

Example 21

The following several Examples describe an additional embodiment of the present invention related to the blocking of enzyme carboxyl for immobilization to charged supports.

As shown and discussed supra, one of the simplest ways to make an inert hydrophobic support hydrophilic and/or functionalized (ie having groups capable of conjugating to reactive groups on a molecule . . . such as an enzyme), is to create carboxylic acid (COO—) groups on the surface. These groups can be introduced in a number of ways: plasma; chemical oxidation; and copolymerization with polymers or monomers bearing carboxylic groups (ie acrylic acid). Additionally, amine containing polymers (ie, chitosan or polyethylenimine as discussed herein) are preferred as grafting intermediates because they are readily available, inexpensive, and can be covalently attached to a carboxylic acid surface in water (as opposed to hydroxyl containing polymers such as PVOH and agarose, which have to be conjugated in organic solvents and may dissolve/swell the polymeric support).

Also as discussed supra, the problem with both caroboxylic and amine surfaces is that they contain a positive (amine) or negative (carboxylic acid) charge around biologically relevant pH. Likewise, enzyme surfaces contain positively (ie, glutamic and aspartic acid) and negatively (ie, lysine) charged amino acids that may interact favorably or unfavorably with the charge surface of the support through electrostatic attractions and repulsions. The unfavorable interactions may lead to denaturation of the enzyme upon conjugation.

Because carboxylic and amine containing surfaces on hydrophobic materials enhance hydrophillicity of the surface, are reactive, readily created, and often used in bioconjugation of proteins, and proteins may denature when in contact with these surfaces, an embodiment of the present invention provides a means to prevent the unfavorable electrostatic interactions between the surface of a protein and the surface of a charged support.

Example 22

This Example describes a method comprising blocking unnecessary functional groups (amine or carboxyl) on the enzyme with small molecules to provide a means of preventing unfavorable electrostatic interactions on a highly charged surface.

In a first step, carboxyl groups of lactase from *Aspergillus oryzae* were blocked using varying amounts of carbodiimide [1-ethyl-3-(3-dimethylamino)propyl)-carbodiimide; EDC]. The carbodiimide has been shown to form stable N-acylurea products with carboxylic acid when used in excess and in the absence of reactive amines and adjacent carboxyls (Naoki and Ikada. 1995. Mechanism of amide formation by carbodiimide for bioconjugation in aqueous media. Bioconjugate Chemistry; 6: 123-130). 0:1, 0.1:1, 1:1, 10:1; 100:1 molar excess of carbodiimide:enzyme carboxyl group was added to a 0.1M MES buffer solution, pH 5.3 and reacted for 2 hours at 25° C. As seen in FIG. 49, enzyme carboxyl groups are blocked by carbodiimide.

The results show that the product has been is contained to the intramolecular level of the enzyme as evidenced by the bright gel electrophoresis bands in FIG. 50, which corresponds to a single molecular weight subunit (ie, no intermolecular crosslinking with free amines of the enzyme).

The results also show that the activity of the free enzyme after blocking is not significantly different until 100 molar excess carbodiimide, resulting in a ~20% decrease in activity under optimum conditions. Though the temperature profile trends of the modified enzymes are not different, there is a significant change in activity between pH 5 and 6 of the 100×-carbodiimide enzyme (FIG. 51). This characteristic is likely due to the effect of the protonation state of the gluatamic and aspartic residues of the enzyme that are altered when blocked.

Example 23

This Example describes the conjugation of the lactase enzyme to activated acrylic acid/polystyrene microspheres. In a first step, acrylic acid/polystyrene microspheres (1 μm; 6.2 squared angstroms between surface carboxyl groups) are activated by reacting surface carboxyl groups with carbodiimide (EDC) in the presence of N-hydroxysuccinimide (NHS) (pH 5.5; 250C, 2 hours) as shown below:

The enzyme is then conjugated though available free amine groups on the molecule to the activated microspheres (pH 6.0; 250C, 2 hours) as shown below:

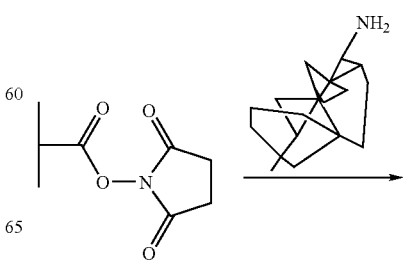

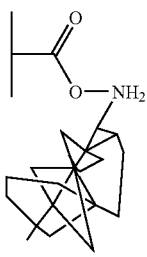

The results show that upon covalently immobilizing the enzyme directly to polystyrene-acrylic acid microspheres (~1 μm), there is an enhancement in the activity profile of the immobilized enzyme at 10× and 100× carbodiimide (excess where the stable acylurea is formed so as to block the carboxyl group).

As seen in FIG. 52 and FIG. 53, specific activity of the enzyme vs. temperature and pH, respectively, is shown. Under optimum conditions, the 100× immobilized enzyme contained ~85% of the activity of it's free enzyme counterpart and ~65% of control free enzyme, compared to ~12% activity retention if the free enzyme is immobilized directly to the support without the addition of carbodiimide. The enhanced activity is believed to be due to a blocking of the carboxyl groups of the enzyme, which occurs in the presence of excess carbodiimide by the formation of a stable N-acylurea product and prevents electrostatic repulsion with the negatively charged surface of the microsphere.

In accordance with an embodiment of the present invention, a similar method can be used for reducing unfavorable ionic interactions on highly charged grafted intermediates that contain amine groups (such as chitosan and PEI) in which carboxyl or amine groups of the enzyme are blocked followed by covalent attachment to an amine-containing support via free amine or carboxyl groups. Additionally, this can be a useful strategy for other enzymes that are susceptible to denaturation when conjugated to ionically charged surfaces such as oxidized materials, carboxymethyl cellulose, pectin, dextran sulfate, alginate, furcellaran, carageenan, and ion exchange supports.

Example 24

The following several Examples describe an additional embodiment of the present invention related the use of surface modification and bioconjugation chemistries to develop materials to which bioactive compounds, that may have use in food packaging, can be covalently attached. Because the bioactive compound can be covalently attached to the food packaging surface, it is unlikely to migrate to the food, and thus is unlikely to be consumed. In accordance with an embodiment of the present invention, a method is provided to covalently attach lactase to the surface of a common food contact polymer, such as polyethylene.

The following Examples include the following materials. Additive-free low-density polyethylene (PE) (100 μm) was kindly donated by Dow Chemical Company (Midland, Mich., U.S.A.). Anhydrous calcium sulfate, glutaraldehyde (50 wt %, photographic grade), sodium cyanoborohydride coupling buffer, 2-nitrophenyl β-D-galactopyranoside (ONPG), Bradford reagent, Schiff's reagent, acid orange 7 (AO7), N-hydroxysuccinimide, polyethyleneimine (PEI, Mw 25,000), bovine albumin (98%), and 1-ethyl-3-(3-dimethylamino-propyl)carbodiimide (EDAC) were purchased from Sigma-Aldrich (St. Louis, Mo., U.S.A.). Reagent grade deionized water (RGDI) was purchased from RICCA Chemical Company (Arlington, Tex., U.S.A.). Lactose, potassium phosphate dibasic, potassium phosphate monobasic, nitric acid (70%), dichloromethane (99.9%), and sulfuric acid (96.0%) were purchased from Mallinckrodt (Paris, Ken., U.S.A.). Centrifugal filter devices were purchased from Millipore (Billerica, Mass., U.S.A.). Acetone (99.7%), syringe filters, toluidine blue 0 (TBO), sodium carbonate, and chromium trioxide (anhydrous) were purchased from Fisher Scientific (Fair Lawn, N.J., U.S.A.). Tris-acetate SDS running buffer (207) was purchased from Invitrogen (Carlsbad, Calif., U.S.A.). Bicinchoninic acid (BCA) assay reagents were purchased from Pierce Biotechnology Inc. (Rockford, Ill., U.S.A.). β-galactosidase (GODO-YNL2), from *Kluyveromyces lactis*, was donated by Valley Research Inc. (South Bend, Ind., U.S.A.), and purified as described below. All other chemicals and reagents were used as received.

The following Examples use one or more of the following abbreviations: PE=Cleaned low density polyethylene; PE-COOH=PE which has been oxidized in chromic acid; PE-NH2=PE-COOH to which polyethylenimine has been covalently attached; PE-GL=PE-NH2 to which glutaraldehyde has been covalently attached; PE-LAC=PE-GL to which lactase has been covalently attached.

Statistical analyses were conducted using Minitab_Release 14.1 Statistical Software (State College, Pa., U.S.A.). One-way analysis of variance (ANOVA) followed by Tukey's pairwise comparison was conducted to determine differences ($P<0.05$). Results were representative of 2 separate trials conducted on different days.

Example 25

This Example describes the surface functionalization of polyethylene. Squares of PE film (20×20 mm) were cleaned by sonicating in dichloromethane (99.9%), acetone (99.7%), and deionized water (10 min per repetition, 3 repetitions per solvent). Films were dried overnight over anhydrous calcium sulfate. Unless otherwise noted, films were rinsed in 3 consecutive deionized water rinses after each modification step. Functionalized films not used immediately were stored in RGDI to minimize migration of polar surface functional groups into the bulk polymer. Films were submerged for 2 min each in a 29:42:29 weight ratio solution of anhydrous chromium trioxide, deionized water, and sulfuric acid (96.0%) at 70° C. (Rasmussen and others 1977). Films were then immersed in nitric acid (70%) at 50° C. for 15 min to remove any chromium salts that may have precipitated during oxidation treatment. PEI was covalently attached to the oxidized film using a modification of the method of Kingshott (Kingshott and others 2003). The conjugation buffer was composed of 30 mg/mL PEI, $3\times10^{-3}$ M EDAC, and $3\times10^{-3}$ MNHS in 0.1 M pH9.6 sodium carbonate buffer. Films were shaken in conjugation buffer for 2 h at 25° C. Surface amine groups were modified with glutaraldehyde to generate surface-reactive aldehyde functionalities via reductive amination (Hermanson 1996). Films were shaken overnight at 25° C. in 0.1 M pH 9.6 sodium carbonate buffer containing 0.08% sodium cyanoborohydride and 0.7 mg/mL glutaraldehyde. Following 3 rinses in deionized water, films were rinsed in 1/15 MpH 6.8 phosphate buffer to condition them for lactase conjugation.

Contact angles (n=6, 1 film per treatment) of control and functionalized PE surfaces were measured on a Tantec CAM-Plus goniometer (Schaumburg, Ill., U.S.A.) using RGDI (Bartell and Zuidema 1936; Mack 1936). Changes in surface chemistry were quantified using specific dyes that interact with specific functional groups. The number of surface carboxyl groups was determined using the toluidine blue O assay (Kang and others 1996). Triplicate films were immersed in $5\times10^{-4}$ M toluidine blue O in deionized water adjusted to pH 10 by NaOH. After 5 h of shaking at 25° C., the films were rinsed with NaOH solution at pH 10 to remove noncomplexed dye. Complexed dye was then desorbed by shaking films in 50 wt % acetic acid for 15 min at 25° C., and absorbance of the acetic acid solution was read at 633 nm. One mole of dye has been reported to be complex with 1 mole of available carboxyl groups (Uchida and others 1993). Absorbance was compared to a standard curve made of dye in 50 wt % acetic acid and has been reported as nmol/cm2. Primary amine groups per unit area were similarly determined except that acid orange 7 was utilized (Uchida and others 1993). Film samples (n=5) were immersed in $1\times10^{-3}$ M acid orange 7 in deionized water adjusted to pH 3 by HCl. After 5 h shaking at 25° C., films were rinsed, dye was desorbed in deionized water adjusted to pH 12 by NaOH, and absorbances were read at 460 nm. The presence of surface aldehydes was qualitatively confirmed using Schiff's reagent (Feigl 1960).

The results show that chromic acid oxidation decreased the contact angle from 105×2° to 50×2° due to increased hydrophilicity (FIG. 54). Further surface modifications remained more hydrophilic than the unmodified PE, but were less hydrophilic than PE-COOH. Dye assays revealed that chemical oxidation resulted in a carboxylic acid concentration of 3.3×0.3 nmol/cm2 Amination of the carboxyl groups with PEI resulted in a primary amine concentration of 15.7×0.6 nmol/cm2 (FIG. 55 and FIG. 56). After glutaraldehyde conjugation, there was an apparent increase in carboxylic acid concentration most likely due to the electrostatic interference of the aldehyde functionality with the dye assay. The reduction in available primary amines after glutaraldehyde conjugation indicated successful attachment of glutaraldehyde to the surface. Only PE-GL films gave a positive result using Schiff's reagent, indicating the presence of aldehyde groups. After attachment of lactase to the surface there was an increase in carboxylic acid concentration, no change in primary amine concentration, and a negative Schiff's reagent response, all of which supported the covalent attachment of lactase to the film surface.

Example 26

This Example describes the covalent attachment of lactase to the surface functionalized polyethylene of Example 25. The commercially prepared β-galactosidase was purified by syringe filtration through a 0.22-μm membrane followed by centrifuge filtration through a 50 KDa centrifugal filter device. Using the Bradford assay (Bradford 1976) with bovine albumin as a standard, the protein content of the purified enzyme preparation was determined to be 60 mg/mL. N-terminal α-amines and lysine ε-amines from lactase were covalently attached to surface aldehyde groups via reductive amination (Hermanson 1996) in 1/15 MpH 6.8 potassium phosphate buffer containing 0.07% sodium cyanoborohydride. Lactose was added to the conjugation buffer at 5 mM to block the enzyme active site during conjugation Films were shaken in conjugation buffer overnight at 37° C. and rinsed 3 times in 1/15 MpH 6.8 phosphate buffer.

Example 27

This Example describes XPS (X-ray photoelectron spectroscopy) analysis. The XPS analysis was conducted at the Penn StateMaterials Characterization Laboratory (State College, Pa., U.S.A.) on a Kratos Analytical Axis Ultra (Kratos Anaytical, Inc., Chestnut Ridge, N.Y., U.S.A.) with a monochromatic Alka X-ray source at an X-ray power of 280 W, a 90° takeoff angle, and a spot size of 700×300 μm.

The results show that the XPS analysis confirmed a change in surface chemistry with each modification (Table 4, below). PE had 99.6% carbon, indicating a clean, pure control film. Chromic acid oxidation introduced 5.6% oxygen, and amination introduced 7.6% nitrogen to the surface, which supports the results of the dye assays. Attachment of glutaraldehyde increased the surface carbon, as expected for an alkyl dialdehyde, and decreased the surface nitrogen due to addition of another monolayer. The presence of lactase was confirmed by the large jump in percent oxygen and nitrogen, the essential elements of a peptide bond.

TABLE 4

XPS atomic composition of control and modified polyethylene films

| Sample | C (%) | O (%) | N (%) |
|---|---|---|---|
| PE | 99.6 | 0.4 | 0.0 |
| PE-COOH | 94.4 | 5.6 | 0.0 |
| PE-NH$_2$ | 82.9 | 9.1 | 7.6 |
| PE-GL | 84.0 | 9.0 | 6.8 |
| PE-LAC | 69.8 | 16.4 | 13.3 |

Example 28

This Example describes the quantification of surface bound protein. Surface-bound protein was quantified by a modified BCA assay, which has been demonstrated to be well suited for determining surface-bound protein with enhanced sensitivity (Plant and others 1991; Sapan and others 1999). Triplicate films were submerged in 1 mL of BCA reagent for 30 min at 37° C. Absorbances were read a 562 nm and surface protein was determined by comparison to a bovine albumin standard curve. The covalent nature of the attachment was verified by heating triplicate films for 10 min at 65° C. in an ionic denaturant (sodium dodecyl sulfate, SDS), followed by quantification of remaining surface protein by BCA assay. After overnight shaking in the reaction buffer, films were rinsed in 3 consecutive vials of 1/15 MpH 6.8 phosphate buffer. The Bradford assay was used on rinse buffer to ensure that all remaining lactase was covalently attached (Bradford 1976).

The results show that the protein content of the unmodified, oxidized, aminated, and aldehyde-treated film was below the detection limit (1.0 μg/cm2) and 6.0×0.8 μg/cm2 following conjugation (FIG. 57). After rigorous treatment with SDS, 74% of attached protein remained, supporting the covalent nature of the attachment of lactase to film. The observed decrease in surface protein under the denaturing conditions may be ascribed to separation of the lactase dimers or changes in secondary structure affecting the BCA assay (Wiechelman and others 1988).

Example 29

This Example describes the determination of free and film-attached lactase. Lactase activity was determined using a modification of the lactase (acid) activity assay (Anonymous 2003), which utilizes ONPG, a synthetic lactose-like substrate that, upon cleavage, releases a yellow compound that can be quantified in a spectrophotometer Films were immersed in 2 mL 3.7 mg/mL ONPG in 1/15 M pH 6.8 phosphate buffer that had equilibrated to 37-C. After 15 min shaking at 37° C., the reaction was quenched by addition of 2.5 mL 10% sodium carbonate in water. Blank and test solutions were diluted to 25 mL with deionized water, and absorbances were read at 420 nm Lactase activity has been reported as lactase units (LU)/cm2, as defined by the liberation of 1 μmol o-nitrophenol per minute per square centimeter of film under the conditions of the assay. The temperature profile of free and film-attached lactase was investigated by conducting the modified assay in 1/15 M pH 6.8 phosphate buffer at temperatures ranging from 5° C. to 60-C. The pH activity profile of free and film-attached lactase was investigated by conducting the lactase assay at 37° C. using 3.7 mg/mL ONPG dissolved in 1/15 M phosphate buffer with pH ranging from 5.0 to 9.0.

The results show the activity of covalently attached lactase at 37° C. and pH 6.8 to be $2 \times 10^{-2}$ LU/cm2, or approximately 4500 LU/g, in which 1 LU is defined as the quantity of ONPG cleaved per unit time at the given conditions, in μmol/min The pH and temperature activity profiles of covalently attached lactase were similar to those of free lactase (FIG. 58 and FIG. 59). Immobilized enzyme systems have been reported to exhibit a change in pH optima as a result of surface charge effects on local microenvironment (Lamb and Stuckey 2000; Wentworth and others 2004). Because milk is neutral in pH, it was important not to change the pH optima of bound enzyme. Covalently attached lactase was found to exhibit optimum activity at pH of 7.0 to 7.5 and temperatures from 37° C. to 45° C., similar to that of free enzyme.

Example 30

This Example describes the assessment of the stability of the covalently attached lactase (as described in the previous Examples). Storage stability was assessed by storing films for 2 weeks in 1/15 M pH 6.8 phosphate buffer at 5-C. ONPG and BCA assays were conducted at 0, 7, and 14 days to quantify lactase activity and surface protein, respectively. Storage buffer was tested for protein to measure possible lactase migration from the film during storage.

In order to assess the stability of the covalently attached lactase, films that were stored in 1/15 M pH 6.8 phosphate buffer at 5° C. were tested for migration of enzyme into storage buffer, quantity of covalently attached protein, and activity of film-attached lactase.

Bradford assay on storage buffers indicated that no enzyme migrated from the film (detection limit=1 μg/mL protein). The results also show that the quantity of surface protein remained constant throughout the study, supporting that the enzyme was covalently attached to the surface (data not shown). Film-attached lactase decreased in activity by 22% to 23% per week during storage (FIG. 60).

In accordance with an embodiment of the present invention, Examples 24-30 demonstrate that yeast-derived β-galactosidase was covalently attached to a surface-modified polyethylene film while sustaining enzyme activity over a range of temperature and pH similar to that of free enzyme. The bond between the film-attached lactase and the functionalized polyethylene withstood heated treatment in an ionic denaturant with 74% enzyme retention, suggesting that migration into foods would be unlikely to occur. The activity, per unit weight, of the covalently attached enzyme was approximately 10% that of free enzyme, possibly due to the removal of the stabilizing agent glycerol during enzyme purification (Cavaille and Combes 1995, supra).

In accordance with an embodiment of the present invention, Examples 24-30 further demonstrate an approach to covalently attaching bioactive compounds to inert polymer surfaces such as PE through chemical means.

In accordance with an embodiment of the present invention, alternative methods for introducing functionality to surfaces such as plasma, corona discharge, and UV treatment (Ozdemir and others 1999) are provided. Optimization of conjugation chemistries to yield higher activity per unit area at refrigerated temperatures can allow for production of lactose free or lactose-reduced milk on a process line identical to that of regular milk, with the only difference being the packaging material. This can allow for less expensive reduced lactose products, which may help to increase dairy consumption amongst the growing population of lactose maldigesters.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

---

What is claimed is:

1. A method of preparing a covalently-modified polymer support capable of hydrolyzing lactose, said method comprising the steps of:
   functionalizing a water insoluble polymer support;
   covalently linking a water soluble molecule to said functionalized polymer support; and
   covalently linking lactase to said water soluble molecule, wherein said lactase is covalently modified to increase stability and enzymatic activity as compared to non-covalently modified lactase.

2. The method of claim 1, wherein said water insoluble polymer support is food packaging.

3. The method of claim 1, wherein said water insoluble polymer support is poly(ethylene).

4. The method of claim 1, wherein said water insoluble polymer support is poly(ethylene vinyl acetate).

5. The method of claim 1, wherein said water insoluble polymer support is a polystyrene/acrylic acid copolymer.

6. The method of claim 1, wherein said water soluble molecule is polyethyleneimine.

7. The method of claim 1, wherein said water soluble molecule is chitosan.

8. The method of claim 1, wherein water insoluble polymer support comprises carboxyl groups, wherein said carboxyl groups are covalently modified.

9. The method of claim 1, wherein said water soluble molecule comprises amine groups, wherein said amine groups are covalently modified.

10. The method of claim 1, wherein the carboxyl groups of said lactase are covalently modified.

11. The method of claim 1, wherein said lactase comprises amine groups, wherein said amine groups are covalently modified.

12. The method of claim 11, wherein said carboxyl groups of said lactase are covalently modified with 1-ethyl-3-(3-dimethylamino-propyl) carbodiimide.

13. The method of claim 11, wherein said carboxyl groups of said lactase are covalently modified with glucosamine.

14. A covalently-modified polymer support capable of hydrolyzing lactose, said support comprising:
   a functionalized water insoluble polymer support;
   a water soluble molecule covalently linked to said water insoluble polymer support; and
   lactase covalently linked to said water soluble molecule, wherein said lactase is covalently modified to increase stability and enzymatic activity as compared to non-covalently modified lactase.

15. The polymer support of claim 14, wherein said water insoluble polymer support is food packaging.

16. The polymer support of claim 14, wherein said water insoluble polymer support is poly(ethylene).

17. The polymer support of claim 14, wherein said water insoluble polymer support is poly(ethylene vinyl acetate).

18. The polymer support of claim 14, wherein said water insoluble polymer support is a polystyrene/acrylic acid copolymer.

19. The polymer support of claim 14, wherein said water soluble molecule is polyethyleneimine.

20. The polymer support of claim 14, wherein said water soluble molecule is chitosan.

21. The polymer support of claim 14, said water soluble molecule comprises carboxyl groups, wherein said carboxyl groups are covalently modified.

22. The polymer support of claim 14, wherein said water soluble molecule comprises amine groups, wherein said amine groups are covalently modified.

23. The polymer support of claim 14, wherein the carboxyl groups of said lactase are covalently modified.

24. The polymer support of claim 14, wherein the amine groups of said lactase are covalently modified.

25. The polymer support of claim 23, wherein said carboxyl groups of said lactase are covalently modified with glucosamine.

26. A method of preparing a covalently-modified polymer support capable of hydrolyzing lactose, said method comprising the steps of:
   introducing carboxylic groups to a polymer support;
   covalently modifying said carboxylic groups; and
   covalently linking lactase to said modified carboxylic groups, wherein said lactase is covalently modified to increase stability and enzymatic activity as compared to non-covalently modified lactase.

27. The method of claim 26, wherein said carboxylic acid groups are introduced to said polymer support using chromic acid.

28. The method of claim 26, wherein said carboxylic groups are modified with 1-ethyl-3-(3-dimethylamino-propyl) carbodiimide in the presence of N-hydroxysuccinimide.

29. The method of claim 26, wherein said lactase is covalently modified with glucosamine.

30. The method of claim 26, wherein said lactase is covalently modified with 1-ethyl-3-(3-dimethylamino-propyl) carbodiimide.

31. A covalently-modified polymer support capable of hydrolyzing lactose, said support comprising:
   a functionalized water insoluble polymer support with modified carboxylic groups; and
   lactase covalently linked to said modified carboxylic groups, wherein said lactase is covalently modified to increase stability and enzymatic activity as compared to non-covalently modified lactase.

32. The polymer support of claim 31, wherein said carboxylic acid groups are introduced to said water insoluble polymer support using chromic acid.

33. The polymer support of claim 31, wherein said carboxylic groups are modified with 1-ethyl-3-(3-dimethylamino-propyl) carbodiimide in the presence of N-hydroxysuccinimide.

34. The polymer support of claim 31, wherein said lactase is covalently modified with glucosamine.

* * * * *